(12) United States Patent
Chen et al.

(10) Patent No.: US 9,045,483 B2
(45) Date of Patent: Jun. 2, 2015

(54) INHIBITION OF SMALL UBIQUITIN-LIKE MODIFIER ENZYMES WITH SUBSTITUTED PYRROLO[2,3-B]QUINOXALINES

(71) Applicants: City of Hope, Duarte, CA (US); Sanford-Burnham Medical Research Institute at Lake Nona, Orlanda, FL (US)

(72) Inventors: Yuan Chen, Arcadia, CA (US); Yi-Jia Li, Duarte, CA (US); Daniela Divlianska, Orlando, FL (US); Ekaterina Bobkova, Orlando, FL (US); Greg Roth, Orlando, FL (US); Jun Pu, Orlando, FL (US); Pasha Khan, Orlando, FL (US)

(73) Assignees: City of Hope, Duarte, CA (US); Sanford-Burnham Medical Research Institute, La Jolla, CA (US)

( * ) Notice: Subject to any disclaimer, the term of this patent is extended or adjusted under 35 U.S.C. 154(b) by 0 days.

(21) Appl. No.: 13/891,076

(22) Filed: May 9, 2013

(65) Prior Publication Data
US 2013/0245032 A1 Sep. 19, 2013

Related U.S. Application Data

(63) Continuation of application No. PCT/US2011/060063, filed on Nov. 9, 2011.

(60) Provisional application No. 61/411,855, filed on Nov. 9, 2010.

(51) Int. Cl.
| C07D 487/04 | (2006.01) |
| A61K 31/555 | (2006.01) |
| A61K 33/24 | (2006.01) |
| A61K 45/06 | (2006.01) |
| C07D 493/08 | (2006.01) |
| A61K 41/00 | (2006.01) |

(52) U.S. Cl.
CPC .......... *C07D 487/04* (2013.01); *A61K 31/555* (2013.01); *A61K 33/24* (2013.01); *A61K 45/06* (2013.01); *C07D 493/08* (2013.01); *A61K 41/00* (2013.01)

(58) Field of Classification Search
CPC ...................................................... C07D 487/04
USPC ........................................................... 544/344
See application file for complete search history.

(56) References Cited

PUBLICATIONS

Jordan, V. C. Nature Reviews: Drug Discovery, 2, 2003, 205.*
Vippagunta, et al. Advanced Drug Delivery Reviews, 48, 2001, 18.*
PubChem Public Chemical Database, CID 1930124, created Jul. 13, 2005, http://pubchem.ncbi.nlm.nih.gov/summary/summary.cgi?q=all&cid=1930124#ec, accessed Nov. 6, 2013.*

* cited by examiner

*Primary Examiner* — Douglas M Willis
(74) *Attorney, Agent, or Firm* — Mintz, Levin, Cohn, Ferris, Glovsky and Popeo, P.C.

(57) ABSTRACT

According to the embodiments described herein, a methods for inhibiting small ubiquitin-like modifier enzymes in a cell are provided. Such methods may include administering certain substituted pyrrolo[2,3-b]-quinoxalines to the cell. In some aspects, the small ubiquitin-like modifier enzyme is SUMO E1 or SUMO E2. In some aspects, the methods may be used to inhibit a cancer cell in vitro (e.g., grown in culture) or in vivo (e.g., as part of a tumor in a subject). In other embodiments, methods for treating a cancer, degenerative diseases and viral infection are provided. Such methods may include administering an effective amount of a pharmaceutical composition to a subject having cancer. The pharmaceutical composition may include a small ubiquitin-like modifier inhibitor compound. In some embodiments, the method for treating a disease may further comprise administering one or more DNA-damaging therapy in combination with administration of the pharmaceutical composition.

3 Claims, 22 Drawing Sheets

| Scaffold |  | |
|---|---|---|
| Compound # | R₁ | R₂ | Synthesized/purchased |
| 1 |  |  | S/P |
| 2 |  |  | S/P |
| 3 |  |  | S/P |
| 4 |  |  | S/P |
| 5 |  |  | P |
| 6 |  |  | P |
| 7 |  |  | P |
| 8 |  |  | P |
| 9 |  |  | P |

Figure 20B

| Scaffold | | | | |
|---|---|---|---|---|
| Compound # | R₁ | R₂ | R₃ | Synthesized/purchased |
| 10 | pentyl | 2-chlorobenzoyl | phenyl | P |
| 11 | allyl | 5-bromo-2-furoyl | phenyl | P |
| 12 | benzyl | propanoyl | phenyl | P |
| 13 | pentyl | phenylsulfonyl | 4-methylphenyl | P |
| 14 | allyl | phenylsulfonyl | 4-methylphenyl | P |
| 15 | 2-methoxyethyl | 4-chlorobenzoyl | 4-methylphenyl | P |
| 16 | pentyl | 2-furoyl | 4-methylphenyl | P |
| 17 | pentyl | benzoyl | 4-methylphenyl | S/P |
| 18 | pentyl | propanoyl | 4-methylphenyl | P |
| 19 | pentyl | H | 4-methylphenyl | P |
| 20 | pentyl | 4-methoxyphenyl | 4-methylphenyl | S |
| 21 | pentyl | 3-fluorophenyl | 4-methylphenyl | S |

| Scaffold |  | | | |
|---|---|---|---|---|
| Compound # | R₁ | R₂ | R₃ | Synthesized/purchased |
| 22 |  |  |  | P |
| 23 |  | H |  | P |
| 24 |  |  |  | P |
| 25 |  |  |  | P |

INHIBITION OF SMALL UBIQUITIN-LIKE MODIFIER ENZYMES WITH SUBSTITUTED PYRROLO[2,3-B]QUINOXALINES

RELATED APPLICATIONS

This application is a continuation application of PCT Application No. PCT/US2011/60063, filed Nov. 9, 2011, which claims the benefit of U.S. Provisional Application No. 61/411,855, filed Nov. 9, 2010, which are hereby incorporated in their entirety and for all purposes.

GOVERNMENT INTEREST

The invention was made with Government support under Grant Nos. R01 GM086172, F32 CA134180, and R03 DA026556-01 awarded by the National Institutes of Health (NIH). The Government has certain rights in the invention.

BACKGROUND

Post-translational modifications of cellular proteins by the small ubiquitin-like modifier (SUMO) family of proteins are important epigenetic mechanisms for regulating various cellular functions. At least three members of the SUMO family (SUMO-1, -2, and -3) are ubiquitin-like proteins that can conjugate to other cellular proteins by a biochemical mechanism similar to ubiquitination (Hay 2005; Sarge 2009; Yeh 2009).

SUMOylation requires multiple steps that are catalyzed by three types of SUMOylation enzymes: activating enzyme E1 (made up of two subunits, SAE1 and SAE2/Uba2), conjugating enzyme E2 (Ubc9), and one of several E3 ligases. This pathway is illustrated for SUMO 1 in FIG. 1. Briefly, SUMO is activated by the E1 enzyme through ATP hydrolysis and forms a thioester conjugate with E1. SUMO is then transferred to E2, forming a thioester conjugate with E2. Finally, SUMO is transferred to target proteins, a step usually stimulated by an E3 ligase. SUMO modification adds a new docking site to target proteins, and thus enables new protein-protein interactions through the SUMO-interacting motif (SIM) in receptor proteins (Song 2004; Song 2005). The E1 and E2 enzymes do not discriminate among the different SUMO paralogues (Tatham 2003).

SUMOylation is reversible by a process known as deSUMOylation. The removal of SUMO proteins from modified target proteins is accomplished by deSUMOylation enzymes such as isopeptidase and SUMO/sentrin-specific protease (SENP).

Aberrations in post-translational modification of cellular proteins by the small ubiquitin-like modifier (SUMO) family of proteins are associated with the pathogenesis of life-threatening diseases, such as cancer (Luo 2009; Kim 2006; Mo 2005), neurodegenerative disorders (Steffan 2004; Subramaniam 2009), and viral infection (Jaber 2009; Ulrich 2009; Kim 2010). Viral infection often involves hijacking the host post-translational modifications, providing viruses with a fast means for becoming established in host cells before the immune system can respond.

SUMOylation and deSUMOylation enzymes regulate dynamic SUMO modifications in controlling cellular functions. One of the predominant functions of SUMO-mediated modifications is in DNA damage response, such as damage caused by chemo- and radiation therapy (CRT), which kills cancer cells by inducing genotoxic stress (Galanty 2009; Morris 2009; Ouyang 2009; Prudden 2009; Li 2010). DNA double-strand breaks (DSBs) are the most dangerous form of DNA damage, and lead to cell death if left unrepaired (FIG. 2) (Darzynkiewicz 2009). Upon DSB formation, the histone protein H2AX is phosphorylated, resulting in recruitment of several DNA damage signaling proteins to the damage sites, including p53-binding protein 1 (53BP1) and ATM (van Attikum 2009). SUMOylation is required for multiple steps in DNA repair pathways, including recruitment of signaling and repair proteins to damage sites and enablement of repair protein function. For example, recruitment of 53BP1 to DNA damage sites is dependent on its SUMOylation (Galanty 2009). 53BP1 mediates the signaling process to stop cell cycle progression and DNA replication and allows time for repair, in which p53 plays an important role. p53 is also involved in apoptosis if DNA damage is not repaired. SUMOylation also plays a role in regulating p53 transactivating activity (Stehmeier 2009) and trafficking (Carter 2007).

SUMOylation also directly regulates repair of various types of DNA damage. Recent studies have shown that SUMOylation is required for both major DSB repair pathways: homologous recombination (HR), in which a homologous sequence acts as a repair template, and non-homologous end joining (NHEJ), in which DSB ends are ligated together (Jeggo 2009). Proteins involved in HR include the well-known breast cancer-related genes BRCA1 and BRCA2, as well as other proteins with DNA binding and helicase activities (Jeggo 2009). Proteins that carry out NHEJ include Ku70, Ku80, DNA-PKcs, XRCC4, XLF, and Artemis (Jeggo 2009). Many proteins in the DSB repair pathways are substrates of SUMOylation (FIG. 2) (Doksani 2009; Morris 2009; Bartek 2010; Li 2010). SUMOylation is also important for response to single-stranded DNA damage (Pfander 2005) and nucleotide base excision repair (Steinacher 2005; Mohan 2007) by modifying repair enzymes to regulate their activity and life spans. These findings suggest that inhibition of SUMO-dependent processes can inhibit repair of a wide range of DNA damage in cancer cells, thereby sensitizing tumor cells to genotoxic stress induced by CRT.

SUMOylation is required for DNA repair, as evidenced by the observation that cells defective in SUMOylation are sensitive to DNA damage reagents (al-Khodairy et al. 1995; Shayeghi et al. 1997). Recently, two independent studies have identified the yeast protein, Mms21, as the SUMO E3 ligase required for repair of both DNA alkylation damage and double-strand breaks (Andrews et al. 2005; Zhao & Blobel 2005). Elimination of Mms21's SUMO E3 activity leads to DNA damage sensitivity. However, the SUMOylation targets in the DNA damage response are not yet well established, nor is SUMOylation's involvement in DNA repair or other cellular functions. Recent studies have shown that a SUMO-targeted ubiquitin ligase (STUBL) is important in DNA damage response, and the ligase specifically recognizes poly-SUMO-2/3 chains to ubiquitinate poly-SUMO modified proteins for degradation (Burgess et al. 2007; Ii et al. 2007; Prudden et al. 2007; Nagai et al. 2008; Cook et al. 2009; Sun et al. 2007).

The enzymes catalyzing SUMO-modification (E1, E2, E3) are present in higher levels in cancer tissues versus normal tissues and in metastasized tumors versus normal cells, and play an important role in cancer proliferation and metastasis. Recent studies suggest that E1 presents an ideal target for the development of cancer therapeutics with specific genetic backgrounds. For example, a genome-wide siRNA screen identified the genes encoding the SUMO E1 subunits SAE1 and SAE2 among those genes with the strongest synthetic lethal interactions with KRas (Luo 2009).

DeSUMOylation enzymes are also thought to be important in cancer. Increased levels of a deSUMOylation isopeptidase (Senp1) have been observed in prostate cancer, and suppression of Senp1 level by siRNA has been shown to suppress prostate cancer and angiogenesis. Hypoxia also induces high levels of SUMO-1. SUMO-mediated protein-protein interactions appear to be involved in most SUMO-dependent processes.

Given the role of SUMOylation in cancer and other disease states such as viral infection, there is a need in the art for novel SUMOylation enzyme inhibitors. Such inhibitors would be useful both as therapeutics and as research tools for studying the role of SUMOylation in cellular regulation.

SUMMARY

According to the embodiments described herein, a SUMOylation inhibitor compound is provided. In one embodiment, the SUMOylation inhibitor compound has a structure comprising:

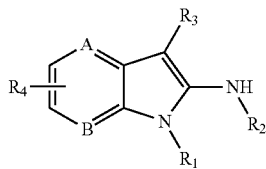

and the pharmaceutically or functionally acceptable derivative, solvates, salts and stereoisomers thereof, including mixtures thereof in all ratios, wherein:

A and B are independently selected from C, N or heteroatoms;

$R_1$ is H, alkyl, haloalkyl, alkyl-$OR_1$, aryl, heterocyclyl, heteroaryl, benzyl, alkyl-aryl wherein $R_1$ is optionally substituted with one to four $R_4$ groups;

$R_2$ is H or L-$R_5$, wherein L is —C(O)— or —S(O2)-, and $R_5$ is alkyl, haloalkyl, cycloalkyl, aryl, heterocyclyl, heteroaryl, benzyl, alkyl-aryl where $R_5$ is optionally substituted with one to four $R_4$ groups;

$R_3$ is CN or —C(O)—$OR_6$, —C(O)—$NHR_6$, —$SO_2R_6$ and $R_6$ is H, alkyl, haloalkyl, aryl, heteroaryl where $R_5$ is optionally substituted with one to four $R_4$ groups; and $R_4$ is halo, —$OR^7$, —$N(R^7)_2$, —$S(R^7)_2$, —$SO_2(R^7)_2$, —$S(O_2)N(R^7)_2$, —$S(O)_2OR^7$, —$N(R^7)S(O)_2R^7$, —$OS(O)_2R^7$, —$C(O)R^7$, —$C(O)OR^7$, —$C(O)N(R^7)_2$, —$OC(O)R^7$, —$OC(O)OR^7$, —$OC(O)N(R^7)_2$, —$N(R^7)C(O)R^7$, —$N(R^7)C(O)OR^7$, —$N(R^7)C(O)N(R^7)_2$, —CN, —$NO_2$, alkyl, haloalkyl, alkyl-$OR^7$, or alkyl-$N(R^7)_2$, where each $R^7$ is independently of H, alkyl, haloalkyl, cycloalkyl, heterocyclyl, aryl or heteroaryl.

In another embodiment, the SUMOylation inhibitor compound has a structure comprising:

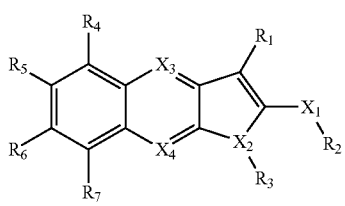

and pharmaceutically acceptable derivatives, solvates, salts and stereoisomers thereof;

wherein $R_1$ and $R_2$ are independently selected from the group consisting of H, —$S(O)_2$—$R_8$, —CN and —C(O)—X—$R_9$;

wherein $R_8$ is an alkyl or aryl;

wherein $R_9$ is an alkyl, aryl, or heteroaryl;

wherein X is selected from the group consisting of C, O, N, S or P;

wherein $R_3$ is selected from the group consisting of an alkyl, an alkenyl, and an alkylaryl;

wherein $R_4$, $R_5$, $R_6$ and $R_7$ are selected from the group consisting of H, a halogen, and an alkyl;

wherein $X_1$ is selected from the group consisting of C, N, O, S, and P; and wherein $X_2$, $X_3$ and $X_4$ are selected from the group consisting of N and O.

In another embodiment, the SUMOylation inhibitor compound has a structure comprising:

Structure B

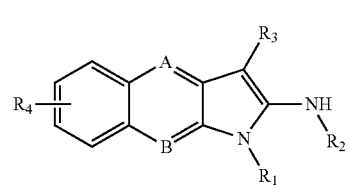

and the pharmaceutically or functionally acceptable derivative, solvates, salts and stereoisomers thereof, including mixtures thereof in all ratios, wherein:

A and B are independently selected from the group consisting of C, N or heteroatoms;

$R_1$ is H, alkyl, haloalkyl, alkyl-$OR_1$, aryl, heterocyclyl, heteroaryl, benzyl, alkyl-aryl where $R_1$ is optionally substituted with one to four $R_4$ groups;

$R_2$ is H or L-$R_5$, wherein L is —C(O)— or —S(O$_2$)—, and $R_5$ is alkyl, haloalkyl, cycloalkyl, aryl, heterocyclyl, heteroaryl, benzyl, alkyl-aryl where $R_5$ is optionally substituted with one to four $R_4$ groups;

$R_3$: is CN or —C(O)—$OR_6$, —C(O)—$NHR_6$, —$SO_2R_6$ and $R_6$ is H, alkyl, haloalkyl, aryl, heteroaryl where $R_5$ is optionally substituted with one to four $R_4$ groups; and $R_4$: is halo, —$OR^7$, —$N(R^7)_2$, —$S(R^7)_2$, —$SO_2(R^7)_2$, —$S(O_2)N(R^7)_2$, —$S(O)_2OR^7$, —$N(R^7)S(O)_2R^7$, —$OS(O)_2R^7$, —$C(O)R^7$, —$C(O)OR^7$, —$C(O)N(R^7)_2$, —$OC(O)R^7$, —$OC(O)OR^7$, —$OC(O)N(R^7)_2$, —$N(R^7)C(O)R^7$, —$N(R^7)C(O)OR^7$, —$N(R^7)C(O)N(R^7)_2$, —CN, —$NO_2$, alkyl, haloalkyl, alkyl-$OR^7$, or alkyl-$N(R^7)_2$, where each $R^7$ is independently of H, alkyl, haloalkyl, cycloalkyl, heterocyclyl, aryl or heteroaryl.

In another embodiment, the SUMOylation inhibitor compound has a structure comprising:

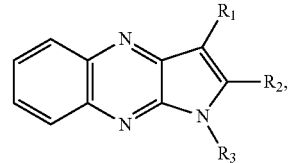

wherein $R_1$ is selected from CN, $SO_2$Tol or CONHBu; $R_2$ is selected from COAr or $SO_2$Ph; and $R_3$ is selected from Bu, Bn or allyl. In certain embodiments, the SUMOylation inhibitor compound may be selected from the group having the structure of:
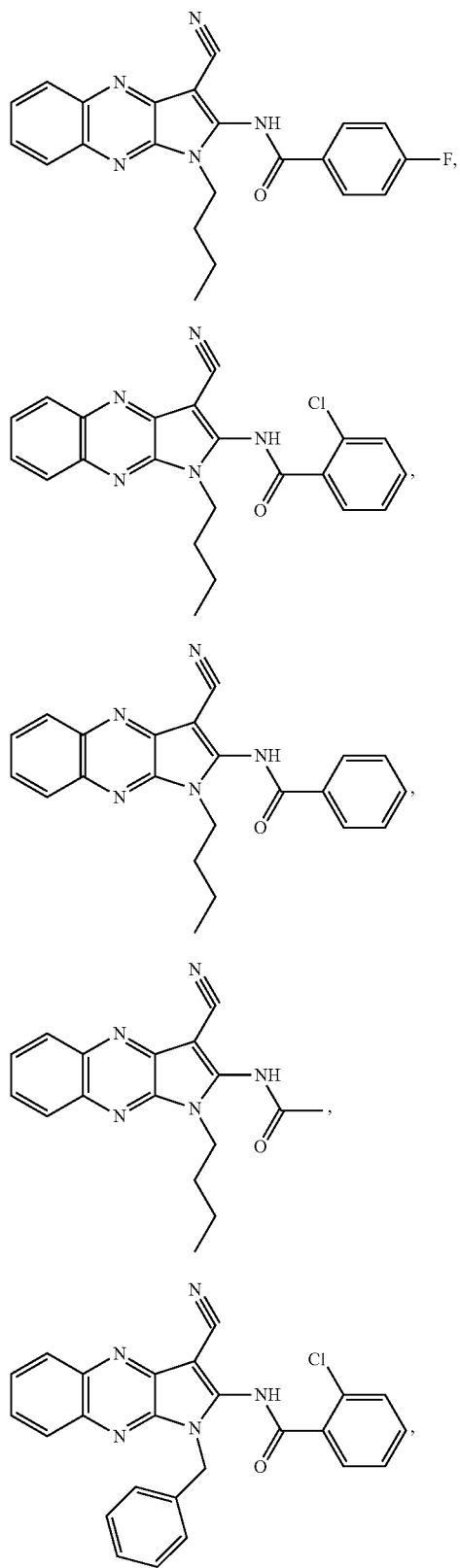
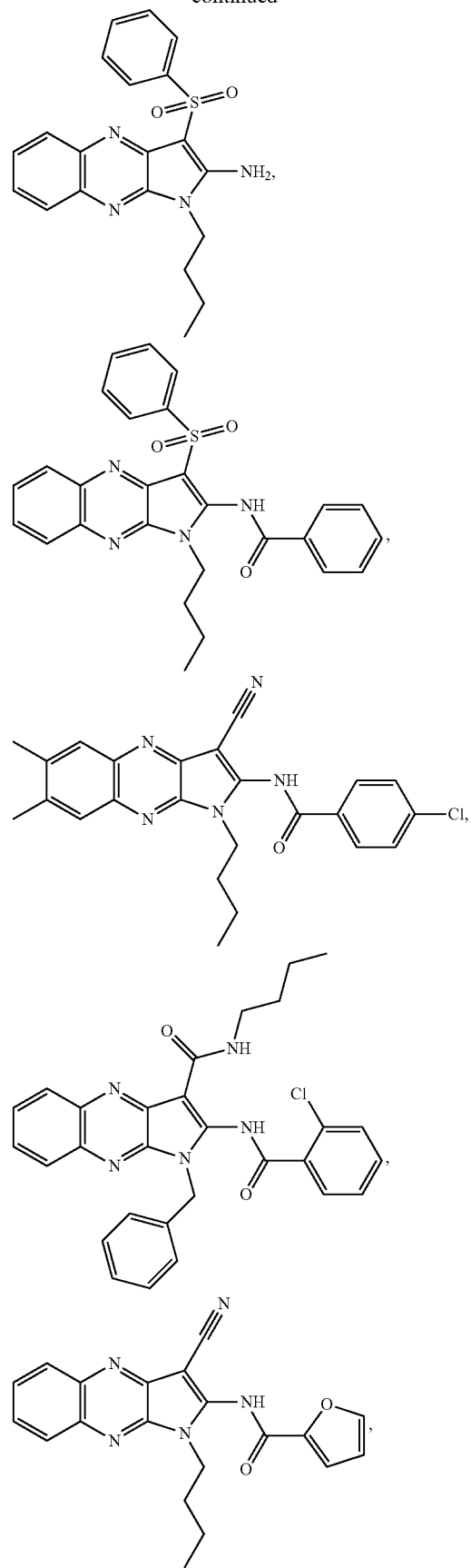

-continued

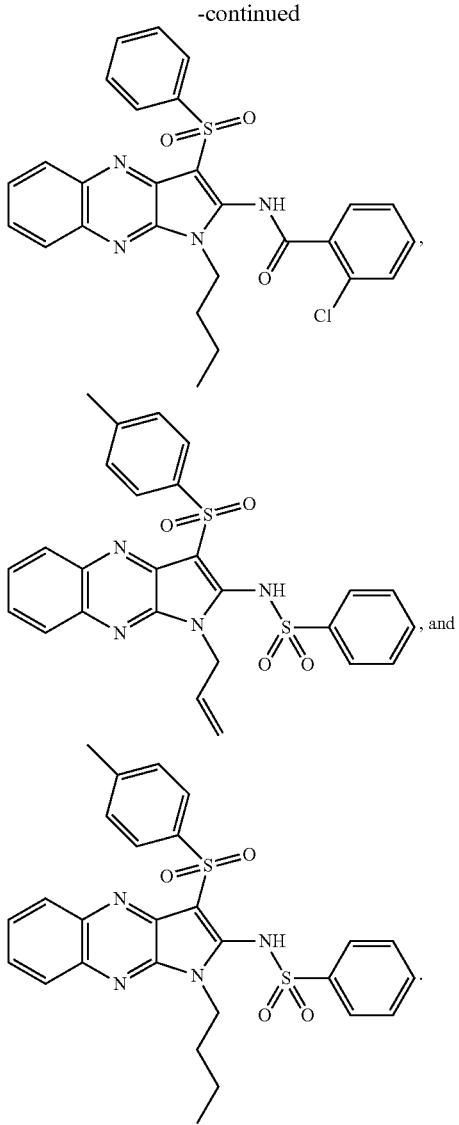

In some embodiments, a method for inhibiting a SUMOylation enzyme in a cell is provided. Such a method may include administering a SUMOylation inhibitor compound, such as those described above, to the cell. In some aspects, the SUMOylation enzyme is SUMO E1 or SUMO E2.

In other embodiments, a method for treating a disease is provided. Such a method may include administering an effective amount of a pharmaceutical composition to a subject having the cancer. The pharmaceutical composition may include a SUMOylation inhibitor compound, such as those described above. In some aspects of this embodiment, the cancer may be any cancer associated with an overexpression or underexpression of a SUMO or SUMOylation enzyme or is associated with SUMOylation of a specific protein. Examples of diseases that may be treated in accordance to the embodiments described herein may include, but are not limited to, cancer and other neoplastic conditions (e.g., colorectal cancer, pancreatic cancer, bone cancer or breast cancer), viral infections (e.g., HIV), hereditary diseases and degenerative diseases.

In some embodiments, the method for treating a cancer may further comprise administering one or more DNA-damaging therapy in combination with administration of the pharmaceutical composition. Examples of DNA damaging therapies that may be administered in accordance with the embodiments of the disclosure include, but are not limited to, an ionizing radiation source or a chemotherapeutic agent selected from an alkylating agent, platinum analogue or other alkylating-like or nonclassical alkylating agent; an intercalating agent; a topoisomerase inhibitor; or a cytotoxic antibiotic.

BRIEF DESCRIPTION OF THE DRAWINGS

FIGS. 20A-C are a series of tables illustrating SUMO inhibitors that were developed in accordance with some embodiments of the tricyclic scaffolds described herein.

DETAILED DESCRIPTION

Figure 1:
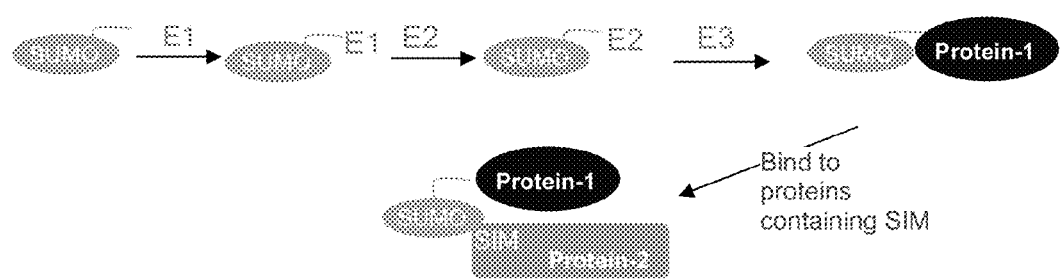
FIG. 1 illustrates the three aspects of the SUMO-mediated processes as they relate to human health. The enzymatic pathway of SUMOylation and a diagram of SUMO-dependent protein complex formation.

Provided herein are small molecule inhibitors of SUMOylation enzymes or pharmaceutically acceptable derivatives thereof, as well as various methods of identifying, making and using these inhibitors. Uses for the SUMOylation enzyme inhibitors described herein include, but are not limited to, methods for modulating radiation sensitivity of cancer cells, killing cancer cells and treating diseases and conditions such as cancer and other neoplastic conditions, viral infections, hereditary diseases and degenerative diseases.

The term "SUMOylation inhibitor" or "SUMO inhibitor" as used herein refers to any small molecule inhibitor that binds one or more subunit of a SUMOylation enzyme, thereby inhibiting the addition of a SUMO protein to a target protein. Such small molecule inhibitors may also inhibit one or more SUMOylation enzymes. The SUMOylation inhibitors, as further described in the studies described herein, have a high level of specificity to SUMO enzymes, thereby affecting SUMOylation, but do not bind or have very low level or negligible binding to proteins found in the ubiquitination pathway. The term "SUMOylation enzyme" or "SUMO enzyme" as used herein refers to SUMO activation enzyme E1, SUMO conjugating enzyme E2 or any one or more of approximately ten SUMO E3 ligases.

In some embodiments, the SUMO inhibitors described herein are SUMO E1 inhibitors. The term "SUMO E1" as used herein refers to SUMO activating enzyme E1, which is made up of subunits SAE1 and SAE2/Uba2. In certain embodiments, the small molecule SUMO E1 inhibitors disclosed herein inhibit the SAE2 subunit of E1, by interfering with the active site or by acting allosterically. The SUMO E1 inhibitors may inhibit SUMO E2. The term "SUMO E2" as used herein refers to SUMO conjugating enzyme E2, which is made up of a single subunit, Ubc9. In certain embodiments, the small molecule SUMO inhibitors described herein inhibit Ubc9 only, or the inhibitors may inhibit Ubc9 and one or more E1 subunits. In these embodiments, the inhibitors may inhibit Ubc9 to a greater degree than the one or more E1 subunits, or they may inhibit two or more of the subunits equally.

Increased expression of SUMO enzymes may contribute to cancer, tumors, or other neoplastic conditions, viral infection, degenerative diseases, genetic or hereditary diseases, or other pathological conditions or diseases. Many cancers have been shown to be associated with increased levels of SUMO enzymes. For example, as discussed in detail in the Examples below, SUMO E1 was found to be the most elevated SUMO enzyme in colorectal cancer tissue, and these high levels of SUMO E1 were associated with radioresistance in colorectal cancer as well as several other types of cancer (Wiatrek et al. Differential expression of small ubiquitin-like modifier family of proteins in patients with colorectal adenocarcinoma; ASCO Abstract, 2011, which is hereby incorporated by reference, as if fully set forth herein; see http://www.asco.org/ascov2/Meetings/Abstracts?&vmview=abst_detail_view&confide=103&abstractID=71189). Overexpression of SUMO enzymes have also been observed in other cancer types (Zhu et al. 2010; Kim et al. 2006; Comerford et al 2003; Cheng et al. 2007; Bergink & Jentsch 2009; Galanty et al. 2009; Morris et al. 2009; Ouyang et al. 2009; Subramaniam et al. 2009; Steffan et al. 2004; Jaber et al. 2009)

Colorectal cancer is the second leading cause of cancer death in the United States (Burt 2009), and CRT is frequently used against colorectal cancer as a preoperative treatment to facilitate surgical intervention (Watanabe 2008) and improve long-term survival (Garcia-Aguilar 2003). However, only a small percentage (<15%) of patients have a complete response to CRT. Therefore, novel SUMO E1 inhibitors that enhance CRT effects and/or impair tumor viability are needed to improve treatment outcomes, preserve quality of life, and reduce healthcare costs. Such SUMO E1 inhibitors may be similarly useful in other cancers, diseases and conditions associated with overexpression of SUMO E1 (Zhu et al. 2010; Kim et al. 2006; Comerford et at 2003; Cheng et al. 2007; Bergink & Jentsch 2009; Galanty et al. 2009; Morris et al. 2009; Ouyang et al. 2009; Subramaniam et al. 2009; Steffan et al. 2004; Jaber et al. 2009).

Therefore, as disclosed herein, a set of small molecule SUMO E1 inhibitors (or "SUMO inhibitor compounds") have been identified and characterized. These inhibitors, which bind to SUMO E1 with high affinity and specificity, represent the first highly specific small molecule inhibitors of SUMO E1. In some embodiments, the SUMO inhibitors do not bind or have negligible binding affinity and specificy for proteins in the ubiquitination pathway. Based on this disclosure, provided herein in certain embodiments are small molecule inhibitors of SUMO E1.

Bicylic Scaffolds

In certain embodiments, the small molecule SUMO inhibitors of pharmaceutically acceptable derivatives thereof provided herein comprise a bicyclic scaffold. The bicyclic scaffold may comprise a structure of Structure A as set forth below:

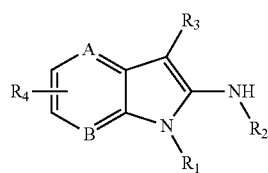

Structure A and the pharmaceutically or functionally acceptable derivative, solvates, salts and stereoisomers thereof, including mixtures thereof in all ratios, wherein:
  A and B are independently selected from C, N or heteroatoms;
  $R_1$ is H, alkyl, haloalkyl, alkyl-$OR_1$, aryl, heterocyclyl, heteroaryl, benzyl, alkyl-aryl wherein $R_1$ is optionally substituted with one to four $R_4$ groups;
  $R_2$ is H or L-$R_5$, wherein L is —C(O)— or —S(O$_2$)—, and $R_5$ is alkyl, haloalkyl, cycloalkyl, aryl, heterocyclyl, heteroaryl, benzyl, alkyl-aryl where $R_5$ is optionally substituted with one to four $R_4$ groups;
  $R_3$ is CN or —C(O)—$OR_6$, —C(O)—$NHR_6$, —$SO_2R_6$ and $R_6$ is H, alkyl, haloalkyl, aryl, heteroaryl where $R_5$ is optionally substituted with one to four $R_4$ groups; and
  $R_4$ is halo, —$OR^7$, —$N(R^7)_2$, —$S(R^7)_2$, —$SO_2(R^7)_2$, —$S(O_2)N(R^7)_2$, —$S(O)_2OR^7$, —$N(R^7)S(O)_2R^7$, —OS(O)$_2R^7$, —$C(O)R^7$, —$C(O)OR^7$, —$C(O)N(R^7)_2$, —OC(O)$R^7$, —OC(O)$OR^7$, —OC(O)$N(R^7)_2$, —$N(R^7)C(O)R^7$, —$N(R^7)C(O)OR^7$, —$N(R^7)C(O)N(R^7)_2$, —CN, —$NO_2$, alkyl, haloalkyl, alkyl-$OR^7$, or alkyl-$N(R^7)_2$, where each $R^7$ is independently of H, alkyl, haloalkyl, cycloalkyl, heterocyclyl, aryl or heteroaryl.

Tricyclic Scaffolds

In certain embodiments, the small molecule SUMO inhibitors or pharmaceutically acceptable derivatives thereof provided herein comprise a tricyclic scaffold. The tricyclic scaffold may comprise a structure of Structure B as set forth below:

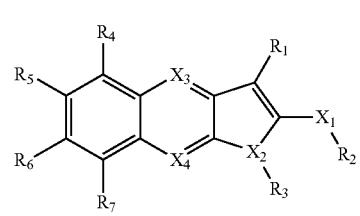

Structure B and the pharmaceutically or functionally acceptable derivative, solvates, salts and stereoisomers thereof, including mixtures thereof in all ratios, wherein:
  $R_1$ and $R_2$ are independently selected from the group consisting of H, —S(O)$_2$—$R_8$, —CN and —C(O)—X—$R_9$;
  $R_8$ is alkyl or aryl;
  $R_9$ is alkyl, aryl, or heteroaryl;
  X is selected from the group consisting of nothing, O, N, S or P;
  $R_3$ is selected from the group consisting of alkyl, alkenyl, and alkylaryl;
  $R_4$, $R_5$, $R_6$ and $R_7$ are independently selected from the group consisting of H, halogen, and alkyl;
  $X_1$ is selected from the group consisting of C, N, O, S, and P; and
  $X_2$, $X_3$ and $X_4$ are independently selected from the group consisting of N, C, O.

In one embodiment, the compound comprising a structure of Structure B, and the pharmaceutically acceptable derivative, solvates, salts and stereoisomers thereof, including mixtures thereof in all ratios, wherein:
  $R_1$ and $R_2$ are independently selected from the group consisting of —S(O)$_2$—$R_8$, —CN and —C(O)—X—$R_9$;
  $R_8$ is unsubstituted phenyl or phenyl substituted with alkyl, alkenyl, alkynel, halo, or alkoxyl;
  $R_9$ is methyl, furanyl, substituted or unsubstituted phenyl;
  X is N for $R_1$, and nothing for $R_2$;
  $R_3$ is butyl, 1- or 2-propenyl, benzyl, or phenyl;
  $R_4$ and $R_7$ are H;
  $R_5$ and $R_6$ are methyl;
  $X_1$ is C or N; and
  $X_2$, $X_3$ and $X_4$ are N.

In a more preferred embodiment, the compound comprising a structure of Structure B, and the pharmaceutically acceptable derivative, solvates, salts and stereoisomers thereof, including mixtures thereof in all ratios, wherein:
  $R_1$ and $R_2$ are independently selected from the group of —S(O)$_2$—$R_8$, —CN and —C(O)—X—$R_8$;
  $R_8$ is phenyl or phenyl substituted with methyl, fluoro, chloride or iodide;
  $R_9$ is methyl, furanyl, phenyl or phenyl substituted with methyl, fluoro, or chloride;
  X is O;

R₃ is butyl or phenyl;
R₄ and R₅ are H;
R₆ and R₇ are methyl;
X₁ is N; and
X₂, X₃ and X₄ are N.

In another embodiment, the tricyclic scaffold may comprise a structure of Structure C as set forth below:

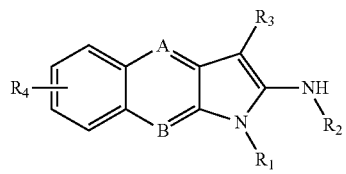

Structure C and the pharmaceutically or functionally acceptable derivative, solvates, salts and stereoisomers thereof, including mixtures thereof in all ratios, wherein:
- A and B are independently selected from the group consisting of C, N or heteroatoms;
- R₁ is H, alkyl, haloalkyl, alkyl-OR₁, aryl, heterocyclyl, heteroaryl, benzyl, alkyl-aryl where R₁ is optionally substituted with one to four R₄ groups;
- R₂ is H or L-R₅, wherein L is —C(O)— or —S(O₂)—, and R₅ is alkyl, haloalkyl, cycloalkyl, aryl, heterocyclyl, heteroaryl, benzyl, alkyl-aryl where R₅ is optionally substituted with one to four R₄ groups;
- R₃: is CN or —C(O)—OR₆, —C(O)—NHR₆, —SO₂R₆ and R₆ is H, alkyl, haloalkyl, aryl, heteroaryl where R₆ is optionally substituted with one to four R₄ groups; and
- R₄: is halo, —OR⁷, —N(R⁷)₂, —S(R⁷)₂, —SO₂(R⁷)₂, —S(O₂)N(R⁷)₂, —S(O)₂OR⁷, —N(R⁷)S(O)₂R⁷, —OS(O)₂R⁷, —C(O)R⁷, —C(O)OR⁷, —C(O)N(R⁷)₂, —OC(O)R⁷, —OC(O)OR⁷, —OC(O)N(R⁷)₂, —N(R⁷)C(O)R⁷, —N(R⁷)C(O)OR⁷, —N(R⁷)C(O)N(R⁷)₂, —CN, —NO₂, alkyl, haloalkyl, alkyl-OR⁷, or alkyl-N(R⁷)₂, where each R⁷ is independently of H, alkyl, haloalkyl, cycloalkyl, heterocyclyl, aryl or heteroaryl.

In certain of these embodiments the inhibitors comprise a quinoxaline scaffold having a structure as set forth below, and the pharmaceutically acceptable derivative, solvates, salts and stereoisomers thereof, including mixtures thereof in all ratios:

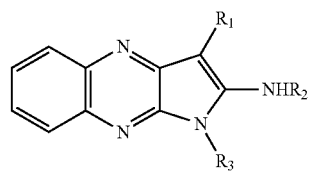

Tricyclic Quinoxaline Scaffold

According to some embodiments, the functional groups of the Tricyclic Quinoxaline scaffold, R₁, R₂ and R₃, are selected according their ability to increase the inhibitory activity of the scaffold. In some embodiments, R₁ is selected from CN, CO2R, CONHR, Tosyl (Ts), SO₂Tol or CONHBu. In other embodiments, R₂ is selected from H, COAr or SO₂Ph. In other embodiments, R₃ is selected from n-Bu, n-Pent, CH₂CH₂OMe, Cy, or Bn. Moreover, the R₁, R₂ and R₃ groups may be modified based on identification of a functional group that exhibits the same, similar or enhanced binding affinity toward a SUMO enzyme binding site as compared to the SUMO inhibitors described herein. In certain of these embodiments the SUMO inhibitors comprise a structure selected from one or more of the following structures and the pharmaceutically acceptable derivative, solvates, salts and stereoisomers thereof, including mixtures thereof in all ratios, set forth in Table 1 below:

TABLE 1

Tricyclic SUMO E1 inhibitors

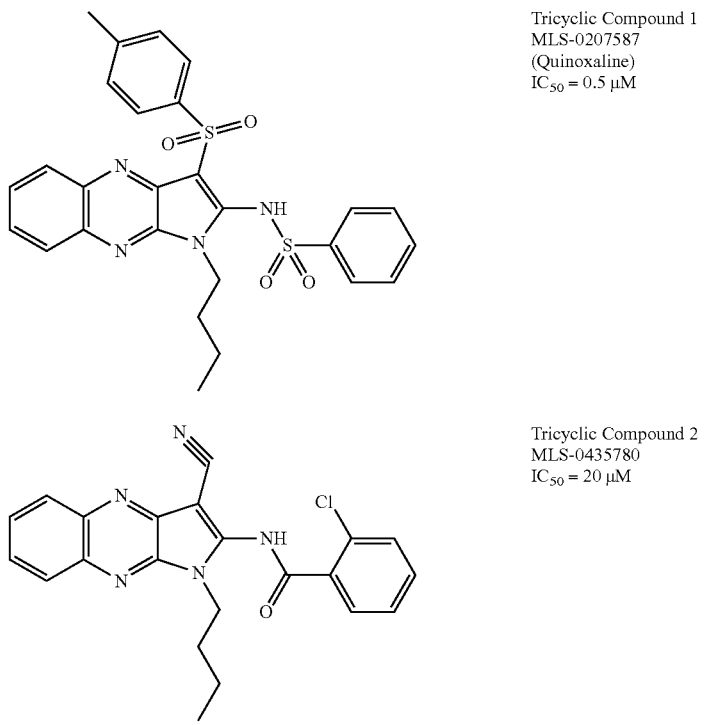

Tricyclic Compound 1
MLS-0207587
(Quinoxaline)
IC₅₀ = 0.5 μM

Tricyclic Compound 2
MLS-0435780
IC₅₀ = 20 μM

TABLE 1-continued
Tricyclic SUMO E1 inhibitors
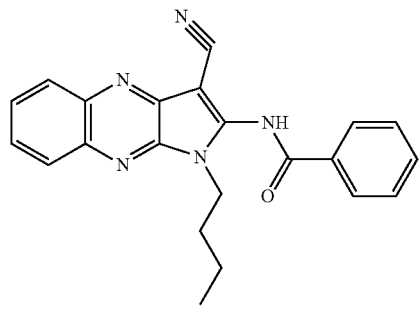 [SMILES: CCCCn1c(NC(=O)c2ccccc2)c(C#N)c2nc3ccccc3nc21]
Tricyclic Compound 3
MLS-0033005
$IC_{50}$ = 3.6 μM
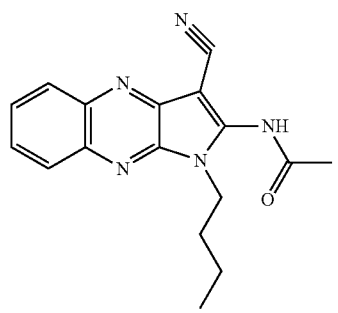 [SMILES: CCCCn1c(NC(C)=O)c(C#N)c2nc3ccccc3nc21]
Tricyclic Compound 4
$IC_{50}$ = 8.3 μM
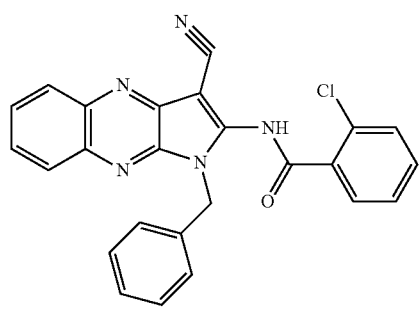 [SMILES: N#Cc1c(NC(=O)c2ccccc2Cl)n(Cc2ccccc2)c2nc3ccccc3nc12]
Tricyclic Compound 5
$IC_{50}$ = 25 μM
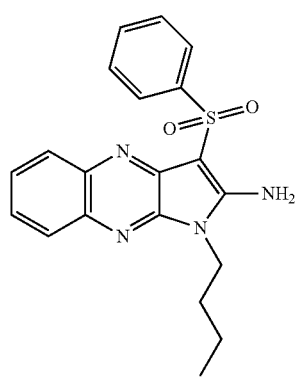 [SMILES: CCCCn1c(N)c(S(=O)(=O)c2ccccc2)c2nc3ccccc3nc21]
Tricyclic Compound 6
$IC_{50}$ = 64 μM TABLE 1-continued
Tricyclic SUMO E1 inhibitors
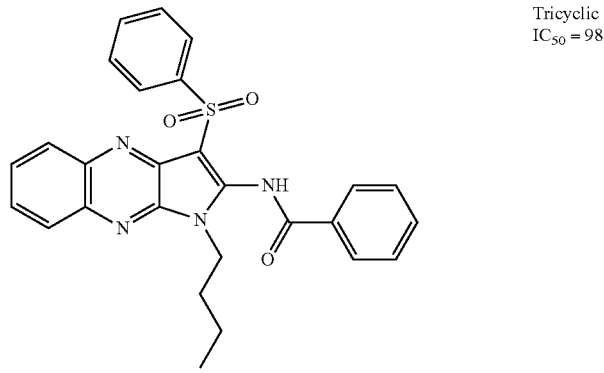
Tricyclic Compound 7
$IC_{50}$ = 98 μM
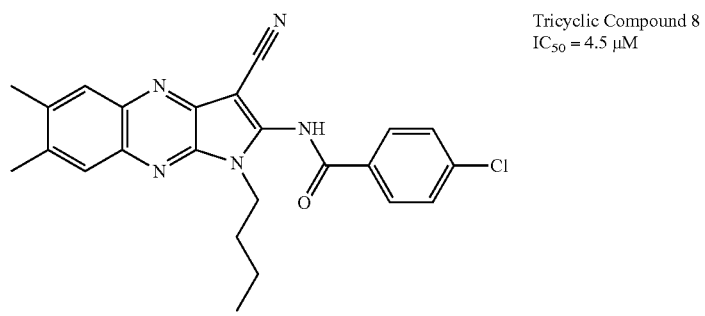
Tricyclic Compound 8
$IC_{50}$ = 4.5 μM
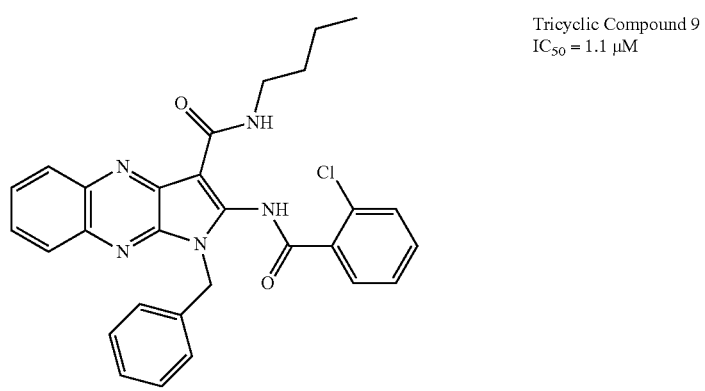
Tricyclic Compound 9
$IC_{50}$ = 1.1 μM
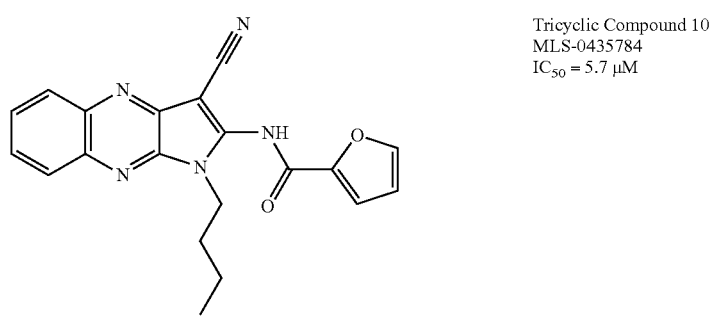
Tricyclic Compound 10
MLS-0435784
$IC_{50}$ = 5.7 μM

TABLE 1-continued

Tricyclic SUMO E1 inhibitors

Tricyclic Compound 11
IC$_{50}$ > 100 μM

Tricyclic Compound 12
IC$_{50}$ = 0.5 μM

Tricyclic Compound 13
MLS-0048297
IC$_{50}$(-BSA) = 0.76 ± 0.07 μM

As used herein, the term "alkyl" refers to a straight or branched chain hydrocarbon having from one to twelve carbon atoms, optionally substituted with substituents selected from the group consisting of C1-C6 alkyl, C1-C6 alkoxy, C1-C6 alkylsulfenyl, C1-C6 alkylsulfenyl, C1-C6 alkylsulfonyl, oxo, hydroxy, mercapto, amino optionally substituted by alkyl, carboxy, carbamoyl optionally substituted by alkyl, aminosulfonyl optionally substituted by alkyl, nitro, cyano, halogen, C1-C6 perfluoroalkyl or C1-C6 perfluoroalkoxy, multiple degrees of substitution being allowed. Examples of "alkyl" as used herein include, but are not limited to, methyl, ethyl, n-propyl, isopropyl, n-butyl, isobutyl, t-butyl, n-pentyl, isopentyl, and the like.

As used herein, when the term "C1-C6" is used to describe a group, it refers to the group containing at least 1, and at most 6, carbon atoms. For example, the term "C1-C6 alkyl" include, but are not limited to, methyl, ethyl, n-propyl, isopropyl, isobutyl, n-butyl, t-butyl, n-pentyl and isopentyl.

As used herein, the term "alkenyl" refers to a straight or branched chain hydrocarbon having from two to twelve carbon atoms and at least one carbon-carbon double bond, optionally substituted with substituents selected from the group consisting of C1-C6 alkyl, C1-C6 alkoxy, C1-C6 alkylsulfanyl, C1-C6 alkylsulfenyl, C1-C6 alkylsulfonyl, oxo, hydroxy, mercapto, amino optionally substituted by alkyl, carboxy, carbamoyl optionally substituted by alkyl, aminosulfonyl optionally substituted by alkyl, nitro, cyano, halogen, C1-C6 perfluoroalkyl or C1-C6 perfluoroalkoxy, multiple degrees of substitution being allowed. Examples of "alkenyl" as used herein include, but are not limited to, ethenyl, n-propenyl, isopropenyl, n-butenyl, isobutenyl, t-butenyl, n-pentenyl, isopentenyl, and the like.

As used herein, the term "alkynyl" refers to a straight or branched chain hydrocarbon having from two to twelve carbon atoms and at least one carbon-carbon triple bond, optionally substituted with substituents selected from the group consisting of C1-C6 alkyl, C1-C6 alkoxy, C1-C6 alkylsulfanyl, C1-C6 alkylsulfenyl, C1-C6 alkylsulfonyl, oxo, hydroxy, mercapto, amino optionally substituted by alkyl, carboxy, carbamoyl optionally substituted by alkyl, aminosulfonyl optionally substituted by alkyl, nitro, cyano, halogen, C1-C6 perfluoroalkyl or C1-C6 perfluoroalkoxy, multiple degrees of substitution being allowed. Examples of "alkyl" as used herein include, but are not limited to, ethynyl, n-propynyl, n-butynyl, isobutynyl, t-butynyl, n-pentynyl, isopentynyl, and the like.

As used herein, the term "halogen" or "hal" refers to fluorine (F), chlorine (Cl), bromine (Br) or iodine (I).

As used herein, the term "aryl" refers to an optionally substituted benzene ring or to an optionally substituted benzene ring system fused to one or more optionally substituted benzene rings to form, for example, anthracene, phenanthrene, or napthalene ring systems. Exemplary optional substituents include C1-C6 alkyl, C1-C6 alkoxy, C1-C6 alkylsulfanyl, C1-C6 alkylsulfenyl, C1-C6 alkylsulfonyl, oxo, hydroxy, mercapto, amino optionally substituted by alkyl, carboxy, tetrazolyl, carbamoyl optionally substituted by alkyl, aminosulfonyl optionally substituted by alkyl, acyl, aroyl, heteroaroyl, acyloxy, aroyloxy, heteroaroyloxy, alkoxycarbonyl, nitro, cyano, halogen, C1-C6 perfluoroalkyl or C1-C6 perfluoroalkoxy, heteroaryl, or aryl, multiple degrees of substitution being allowed. Examples of "aryl" groups include, but are not limited to phenyl, 2-naphthyl, 1-naphthyl, biphenyl, as well as substituted derivatives thereof.

As used herein, the term "heteroaryl" refers to a monocyclic five to seven-membered aromatic ring, or to a fused bicyclic aromatic ring system comprising two of such monocyclic five to seven-membered aromatic rings. These hetroaryl rings contain one or more nitrogen, sulfur and/or oxygen heteroatoms, where N-oxides and sulfur oxides and dioxides are permissible heteroatom substitutions and may be optionally substituted with up to three members selected from a group consisting of C1-C6 alkyl, C1-C6 haloalkyl, C1-C6 haloalkoxy, C1-C6 alkoxy, C1-C6 alkylsulfanyl, C1-C6 haloalkylsulfanyl, C1-C6 alkylsulfenyl, C1-C6 alkylsulfonyl, oxo, hydroxy, mercapto, amino optionally substituted by alkyl, carboxy, tetrazolyl, carbamoyl optionally substituted by alkyl, aminosulfonyl optionally substituted by alkyl, acyl, aroyl, heteroaroyl, acyloxy, aroyloxy, heteroaroyloxy, alkoxycarbonyl, nitro, cyano, halogen, C1-C6 perfluoroalkyl or C1-C6 perfluoroalkoxy, heteroaryl or aryl, multiple degrees of substitution being allowed. Examples of "heteroaryl" groups used herein include furanyl, thiophenyl, pyrrolyl, imidazolyl, pyrazolyl, triazolyl, tetrazolyl, thiazolyl, oxazolyl, isoxazolyl, oxadiazolyl, oxo-pyridyl, thiadiazolyl, isothiazolyl, pyridyl, pyridazyl, pyrazinyl, pyrimidyl, quinolinyl, isoquinolinyl, benzofuranyl, benzothiophenyl, indolyl, indazolyl, and substituted versions thereof.

As used herein, the term "haloalkyl" refers to an alkyl group as defined above containing carbon atoms substituted with at least one halogen, halogen being as defined herein. Examples of branched or straight chained "C1-C6 haloalkyl" groups useful in the present invention include, but are not limited to, methyl, ethyl, propyl, isopropyl, isobutyl and n-butyl substituted independently with one or more halogens, e.g., fluoro, chloro, bromo and iodo.

As used herein, the term "alkoxy" refers to the group RaO—, where Ra is alkyl as defined above. Exemplary C1-C6 alkoxy groups useful in the invention include, but are not limited to methoxy, ethoxy, n-propoxy, isopropoxy, n-butoxy and t-butoxy.

As used herein, the term "haloalkoxy" refers to the group RbO—, wherein Rb is haloalkyl as defined above.

As used herein, the term "alkylsulfanyl" refers to the group $R_A S$—, where $R_A$ is alkyl as defined above.

As used herein, the term "haloalkylsulfanyl" refers to the group $R_D S$—, where $R_D$ is haloalkyl as defined above.

As used herein, the term "alkylsulfenyl" refers to the group $R_A S(O)$—, where $R_A$ is alkyl as defined above.

As used herein, the term "alkylsulfonyl" refers to the group $R_A SO_2$—, where $R_A$ is alkyl as defined above.

As used herein, the term "oxo" refers to the group =O.

As used herein, the term "mercapto" refers to the group SH.

As used herein, the term "carboxy" refers to the group COOH.

As used herein, the term "cyano" refers to the group CN.

As used herein, the term "cyanoalkyl" refers to the group $R_B CN$, wherein $R_B$ is alkylen as defined above. Exemplary "cyanoalkyl" groups useful in the invention include, but are not limited to, cyanomethyl, cyanoethyl and cyanoisopropyl.

As used herein, the term "aminosulfonyl" refers to the group $SO_2 NH_2$.

As used herein, the term "carbamoyl" refers to the group $C(O)NH_2$.

As used herein, the term "sulfanyl" shall refer to the group S—.

As used herein, the term "sulfenyl" shall refer to the group S(O)—.

As used herein, the term "sulfonyl" shall refer to the group $S(O)_2$— or $SO_2$.

As used herein, the term "acyl" refers to the group $R_F C(O)$—, where $R_F$ is alkyl, cycloalkyl or heterocyclyl as defined herein.

As used herein, the term "C3-C7 cycloalkyl" refers to a non-aromatic cyclic hydrocarbon ring having from three to seven carbon atoms and which optionally includes a C1-C6 alkyl linker through which it may be attached. The C1-C6 alkyl group is as defined above. Exemplary "C3-C7 cycloalkyl" groups include, but are not limited to, cyclopropyl, cyclobutyl, cyclopentyl, cyclohexyl and cycloheptyl.

As used herein, the term "heterocyclic" or the term "heterocyclyl" refers to a three to twelve-membered heterocyclic ring having one or more degrees of unsaturation containing one or more heteroatomic substitutions selected from S, SO, $SO_2$, O or N, optionally substituted with substituents selected from the group consisting of C1-C6 alkyl, C1-C6 haloalkyl, C1-C6 haloalkoxy, C1-C6 alkoxy, C1-C6 alkylsulfanyl, C1-C6 haloalkylsulfanyl, C1-C6 alkylsulfenyl, C1-C6 alkylsulfonyl, oxo, hydroxy, mercapto, amino optionally substituted by alkyl, carboxy, carbamoyl optionally substituted by alkyl, aminosulfonyl optionally substituted by alkyl, nitro, cyano, halogen, C1-C6 perfluoroalkyl or C1-C6 perfluoroalkoxy, multiple degrees of substitution being allowed. Such a ring may be optionally fused to one or more other "heterocyclic" ring(s) or cycloalkyl ring(s). Examples of "heterocyclic" moieties include, but are not limited to, tetrahydrofuran, pyran, 1,4-dioxane, 1,3-dioxane, pyrrolidine, piperidine, morpholine, tetrahydrothiopyran, tetrahydrothiophene, and the like.

As used herein, the term "aroyl" refers to the group $R_C C(O)$—, where $R_C$ is aryl as defined herein.

As used herein, the term "heteroaroyl" refers to the group $R_E C(O)$—, where $R_E$ is heteroaryl as defined herein.

As used herein, the term "alkoxycarbonyl" refers to the group $R_A OC(O)$—, where RA is alkyl as defined herein.

As used herein, the term "acyloxy" refers to the group $R_F C(O)O$, where $R_F$ is alkyl, cycloalkyl, or heterocyclyl as defined herein.

As used herein, the term "aroyloxy" refers to the group $R_c C(O)O$—, where $R_c$ is aryl as defined herein.

As used herein, the term "heteroaroyloxy" refers to the group $R_E C(O)O$—, where $R_E$ is heteroaryl as defined herein.

As used herein, the term "carbonyl" or "carbonyl moiety" refers to the group C=O.

As used herein, the term "thiocarbonyl" or "thiocarbonyl moiety" refers to the group C=S.

As used herein, the term "amino," "amino group" or "amino moiety" refers to the group $NR_GR_G'$, wherein $R_G$ and $R_G'$, are preferably selected, independently from one another, from the group consisting of hydrogen, alkyl, haloalkyl, haloalkoxy, alkenyl, cycloalkyl, alkylenecycloalkyl, cyanoalkyl, aryl, aralkyl, heteroaryl, acyl and aroyl. If both $R_G$ and $R_G'$ are hydrogen, $NR_GR_G'$ is also referred to as "unsubstituted amino moiety" or "unsubstituted amino group." If $R_G$ and/or $R_G'$ are other than hydrogen, $NR_GR_G'$ is also referred to as "substituted amino moiety" or "substituted amino group."

As used herein, the term "imino" or "imino moiety" refers to the group $C=NR_G$, wherein $R_G$ is preferably selected from the group consisting of hydrogen, alkyl, haloalkyl, haloalkoxy, alkenyl, cycloalkyl, alkylenecycloalkyl, cyanoalkyl, aryl, aralkyl, heteroaryl, acyl and aroyl. If $R_G$ is hydrogen, $C=NR_G$ is also referred to as "unsubstituted imino moiety." If $R_G$ is a residue other than hydrogen, C=NRG is also referred to as "substituted imino moiety."

As used herein, the term "perfluoroalkyl" refers to an alkyl group with all hydrogens replaced by fluorine, e.g. without limitation, —$CF_3$.

As used herein, the term "perfluoroalkoxy" refers to an alkoxyl group with all hydrogens replaced by fluorine, e.g. without limitation, —$OCF_3$.

As used herein,

refers to a single bond or double bond.

As used herein, the terms "group," "residue" and "radical" or "groups," "residues" and "radicals" are usually used as synonyms, respectively, as it is common practice in the art.

Method for Inhibiting a SUMOylation Enzyme

In some embodiments, the small molecule SUMO inhibitors described herein may be used in methods for inhibiting a SUMOylation enzyme in a cell. Such methods may include a step of administering an effective amount of a SUMO inhibitor compound to the cell.

According to the embodiments described herein, the SUMO inhibitor compound is one or more of the SUMO inhibitors described herein. The SUMO inhibitors may therefore be used in methods for inhibiting a SUMOylation enzyme (e.g., SUMO E1, SUMO E2 or any one or more of the SUMO E3 ligases) in a cell, as provided herein. In some embodiments, such methods for inhibiting a SUMOylation enzyme may include a step of contacting the cell with or administering to the cell, one or more SUMO inhibitors or a pharmaceutically acceptable derivative thereof, described herein.

The cell may be of any cell type that is associated with SUMOylation (e.g., a cell that overexpresses a SUMOylation enzyme, underexpresses a SUMOylation enzyme, or a cell that expresses a specific cellular protein that is SUMOylated in a disease or other physiological or pathological condition). In certain embodiments, the cell type used in the methods for inhibiting a SUMOylation enzyme described herein may be a cell that is part of a population of cells or a biological tissue that is present, in vivo, in a subject having the disease or other physiological or pathological condition. This may include a human or animal patient that develops the disease or other physiological or pathological condition or, alternatively, may include an animal or invertebrate model wherein the disease, or physiological or pathological condition may be induced. In other embodiments, the cell type used in the methods for inhibiting a SUMOylation enzyme described herein may be a primary, secondary or immortal cell line that is grown in culture. In certain aspects of this embodiment, the method may be used in an in vitro or research setting to investigate the role of SUMOylation in the particular cell, disease, or condition.

The term "effective amount" as used herein refers to an amount of a compound that produces a desired effect. For example, a population of cells may be contacted with an effective amount of a compound to study its effect in vitro (e.g., cell culture) or to produce a desired therapeutic effect ex vivo or in vitro. An effective amount of a compound may be used to produce a therapeutic effect in a subject, such as preventing or treating a target condition, alleviating symptoms associated with the condition, or producing a desired physiological effect. In such a case, the effective amount of a compound is a "therapeutically effective amount," "therapeutically effective concentration" or "therapeutically effective dose." The precise effective amount or therapeutically effective amount is an amount of the composition that will yield the most effective results in terms of efficacy of treatment in a given subject or population of cells. This amount will vary depending upon a variety of factors, including but not limited to the characteristics of the compound (including activity, pharmacokinetics, pharmacodynamics, and bioavailability), the physiological condition of the subject (including age, sex, disease type and stage, general physical condition, responsiveness to a given dosage, and type of medication) or cells, the nature of the pharmaceutically acceptable carrier or carriers in the formulation, and the route of administration. Further an effective or therapeutically effective amount may vary depending on whether the compound is administered alone or in combination with another compound, drug, therapy or other therapeutic method or modality. One skilled in the clinical and pharmacological arts will be able to determine an effective amount or therapeutically effective amount through routine experimentation, namely by monitoring a cell's or subject's response to administration of a compound and adjusting the dosage accordingly. For additional guidance, see Remington: The Science and Practice of Pharmacy, 21$^{st}$ Edition, Univ. of Sciences in Philadelphia (USIP), Lippincott Williams & Wilkins, Philadelphia, Pa., 2005, which is hereby incorporated by reference as if fully set forth herein.

E1 contains several substrate-binding sites, including the ATP-binding pocket (Lois & Lima 2005), two SUMO-binding surfaces (Lois & Lima 2005, Wang & Chen) and three Ubc9-binding surfaces (Wang et al. 2007; Wang & Chen; Huang et al. 2007). As discussed in the Examples below, the tricyclic SUMO inhibitors disclosed herein were found to competitively inhibit ATP binding. Since cellular concentrations of ATP are generally high, this ATP inhibition by certain of the inhibitors described herein does not necessarily result in cell toxicity when administered to a cell or to a subject in an effective dose. However, inhibition of ATP binding does sensitize cells to genotoxic stress and inhibit HIV infection as discussed further in the Examples below. Therefore, provided herein in certain embodiments described below are methods of using the tricyclic SUMO inhibitors disclosed herein to sensitize cells to genotoxic stress and/or to treat HIV and other viral infections (see FIG. 14).

In another embodiment, inhibition of ATP binding by the tricyclic SUMO E1 inhibitors disclosed herein makes the inhibitors useful as research probes for identifying and/or monitoring SUMOylation activity in vitro. In such embodiments, the tricyclic inhibitors may be conjugated to or otherwise associated with a label for use in various cellular assays. Labels that may be used in accordance with these embodiments may include, but are not limited to, radiolabels such as the radionuclides described below and fluorophores, thiol-reactive labels, biotin and hapten derivatives, crosslinking and photoactivatable reagents, avidins and lectins for use with antibodies, enzyme substrates and other suitable fluorescent labels. For additional guidance, see Molecular Probes Handbook, A Guide to Fluorescent Probes and Labeling Technologies, 11$^{th}$ Edition, Invitrogen, 2010. (Iain Johnson and Michelle T. Z. Spence, Eds.), which is hereby incorporated by reference as if fully set forth herein.

In such embodiments, the SUMO inhibitors may be used as probes in cell culture assays to determine the effect of SUMOylation activity in a particular cell line. To test whether SUMOylation of a protein of interest in involved in a particular function, a labeled SUMO inhibitor (MLS-0207587) may be added to determine whether the output of the assay changes. For example, a SUMO inhibitor probe was used to demonstrate that the inhibitor specifically inhibits recruitment of 53BP1 and BRCA to DNA damage sites (both of which are SUMO-dependent processes in the DNA damage response), thereby validating the role of SUMO inhibitors for sensitizing cancer cells to radiation (see FIGS. 15-19).

Methods for Treating Cancer

Provided herein in certain embodiments are methods for treating a condition or disease with one or more of the SUMO inhibitors (or "SUMOylation inhibitors" or "SUMOylation inhibitor compounds") and the pharmaceutically acceptable derivative, solvates, salts and stereoisomers thereof, including mixtures thereof in all ratios, described herein These methods may include, but are not limited to, administering a therapeutically effective amount of the one or more SUMO inhibitors or pharmaceutically acceptable derivative, solvates, salts and stereoisomers thereof, including mixtures thereof in all ratios to a subject having the condition or disease. In one embodiment, the SUMO inhibitor is a SUMO E1 inhibitor. In certain embodiments, the or one or more SUMO inhibitors may be identified by methods described herein, for example, using a high throughput screening method to identify a SUMO inhibitor followed by biochemical assays to confirm activities and cellular assays to validate the effects of such inhibitors in cells).

As used herein, the term "functionally effective derivative" or "pharmaceutically acceptable derivative" refers to any physiologically functional derivative of a novel SUMO inhibitor disclosed herein. Such derivatives may include pharmaceutically acceptable salts or so-called pro-drug-compounds, for example compounds according to the invention that are derivatized with alkyl groups, acyl groups, sugars or peptides, such as oligopeptides, that are easily degraded or metabolized to the active compounds according to the invention. Such derivatives may include biodegradable polymer derivatives of the compounds according to the embodiments described herein. Suitable polymers and methods for producing biodegradable polymeric derivatives are known in the art. Further, such derivatives include analogs that have substitutions or modifications that one skilled in the art would recognize as having the same, similar or improved function as the SUMO inhibitors described herein. Upon administration to a subject, a functional derivative of a SUMO inhibitor is capable of providing, directly or indirectly, a SUMO inhibitor disclosed herein, an analog of a SUMO inhibitor disclosed herein or an active metabolite thereof. Such derivatives are clear to those skilled in the art, without undue experimentation. For additional guidance, see Burger's Medicinal Chemistry, Drug Discovery and Development, 7th Edition, Wiley-Interscience, 2010, which is incorporated herein by reference as if fully set forth herein to the extent that it teaches physiologically functional derivatives.

As used herein, the term "solvate" refers to a complex of variable stoichiometry formed by a solute (in this invention, a SUMO inhibitor derivative comprising a structure described herein or a salt or physiologically functional derivative thereof) and a solvent. Such solvents for the purpose of the invention may not interfere with the biological activity of the solute. Examples of suitable solvents include, but are not limited to, water, aqueous solution (e.g. buffer), methanol, ethanol and acetic acid. Preferably, the solvent used is a pharmaceutically acceptable solvent. Examples of suitable pharmaceutically acceptable solvents include, without limitation, water, aqueous solution (e.g. buffer), ethanol and acetic acid. Most preferably, the solvent used is water or aqueous solution (e.g. buffer). Examples for suitable solvates are the mono- or dihydrates or alcoholates of the compounds according to the invention.

Certain of the compounds described herein may contain one or more chiral atoms, or may otherwise be capable of existing as two or more stereoisomers, which are usually enantiomers and/or diastereomers. Accordingly, the compounds of this invention include mixtures of stereoisomers, mixtures of enantiomers, as well as purified stereoisomers, purified enantiomers, or stereoisomerically enriched mixtures, enantiomerically enriched mixtures. Also included within the scope of the invention are the individual isomers of the compounds represented by the structures described herein as well as any wholly or partially equilibrated mixtures thereof. The invention also covers the individual isomers of the compounds represented by the structures above as mixtures with isomers thereof in which one or more chiral centers are inverted. Also, it is understood that all tautomers and mixtures of tautomers of the SUMO inhibitor compounds described herein are included within the scope of the SUMO inhibitor compounds and preferably the structures and scaffolds corresponding thereto.

Racemates obtained can be resolved into the isomers mechanically or chemically by methods known in the art. Diastereomers are preferably formed from the racemic mixture by reaction with an optically active resolving agent. Examples of suitable resolving agents are optically active acids, such as the D and L forms of tartaric acid, diacetyltartaric acid, dibenzoyltartaric acid, mandelic acid, malic acid, lactic acid or the various optically active camphorsulfonic acids, such as camphorsulfonic acid. Also advantageous is enantiomer resolution with the aid of a column filled with an optically active resolving agent (for example dinitrobenzoyl phenylglycine); an example of a suitable eluent is a hexane/isopropanol/acetonitrile mixture. The diastereomer resolution mat also be carried out by standard purification processes, such as, for example, chromatography or fractional crystallization. It also possible to obtain optically active SUMO inhibitor compounds by the methods described above by using starting materials which are already optically active.

SUMOylation inhibitors, when used for a short period of time, are unlikely to be toxic to normal (noncancerous) cells that divide slowly. Recent studies have shown that expression of a peptide inhibitor of the down-stream effects of SUMOylation did not induce cytotoxicity in MCF-7 (WT KRas status) cells in the absence of genotoxic stress (Li et al. 2010).

The small molecule SUMO inhibitors and the pharmaceutically or functionally acceptable derivatives, solvates, salts and steroisomers thereof, including mixture thereof in all ratios provided herein may be used to treat any condition or disease that is associated with altered levels of SUMOylation including, but not limited to, cancer, tumors, neoplastic conditions or syndromes, viral infections (e.g., HIV), cardiovascular disease, degenerative disease and genetic or hereditary diseases. Such diseases may be associated with, for example, an overexpression or underexpression of one or more SUMOylation enzymes or one or more specific proteins that are SUMOylated in the disease or condition. Examples of specific proteins that may be SUMOylated in a disease or condition include, but are not limited to, p53, HDAC, cyclins and other proteins in cancer; SOD1 in amyotrophic lateral sclerosis; ataxin-1 in spinocerebellar ataxia; huntingtin in Huntington's disease; tau, α-synuclein, DJ-1 or other proteins in Parkinson's disease; tau, APP or other proteins in Alzheimer's disease, lamin A in familial dilated cardiomyopathy; 1E1 and 1E2 in human CMV; and P6-Gag in HIV.

In one embodiment, the small molecule SUMO E1 inhibitors provided herein are used to treat any cancer associated with increased or decreased expression of SUMO enzymes.

Cancers, tumors or other neoplastic conditions or syndromes that may be treated according to the embodiments described herein include, but are not limited to adenoid cystic carcinoma, adrenal gland tumor, amyloidosis, anal cancer, appendix cancer, ataxia-telangiectasia, attenuated familial adenomatous polyposis, Beckwith-Wiedemann syndrome, bile duct cancer, Birt-Hogg-Dube syndrome, bladder cancer, bone cancer, brain tumor, breast cancer, carcinoid tumor, Carney Complex, cervical cancer, childhood cancer (e.g., brain stem glioma, astrocytoma, central nervous system, craniopharyngioma, Desmoplastic Infantile ganglioglioma, ependymoma, Ewings family of tumors, germ cell tumor, acute lymphoblastic leukemia (ALL), acute myeloid leukemia (AML), Hodgkin's lymphoma, Non-Hodgkin's lymphoma, medulloblastoma, neuroblastoma, osteosarcoma, pleuropulmonary blastoma, retinoblastoma, rhabdomyosarcoma, Wilms tumor), colorectal cancer, Cowden syndrome, endocrine tumor, endometrial cancer, esophageal cancer, eye cancer, eyelid cancer, fallopian tube cancer, familial adenomatous polyposis, familial malignant melanoma, gallbladder cancer, Gardner syndrome, gastrointestinal stromal tumor (GIST), gestational trophoblastic tumor, head and neck cancer, hereditary cancer (e.g., breast, ovarian, diffuse gastric, leiomyomatosis, renal cell, mixed polyposis syndrome, non-VHL clear cell renal cell carcinoma, pancreatitis and papillary renal cell carcinoma), HIV and AIDS-related cancer, islet cell tumor, juvenile polyposis syndrome, kidney cancer, lacrimal gland tumor, laryngeal and hypopharyngeal cancer, leukemias (e.g., acute lymphocytic leukemia (ALL), acute myeloid leukemia (AML), B-cell leukemia, chronic lymphocytic leukemia (CLL), chronic myeloid leukemia (CML), eosinophilic leukemia, T-cell leukemia), Li-Fraumeni syndrome, liver cancer, lung cancer, Hodgkin's lymphoma, Non-Hodgkin's lymphoma, Lynch syndrome, mastocytosis, melanoma, meningioma, mesothelioma, Muir-Torre syndrome, multiple endocrine neoplasia types 1 and 2, multiple myeloma, myelodysplastic syndromes (MDS), MYH-associated polyposis, nasal cavity and paranasal sinus cancer, nasopharyngeal cancer, neuroendocrine tumor, neurofibromatosis types 1 and 2, nevoid basal cell carcinoma syndrome, oral and oropharyngeal cancer, ovarian cancer, pancreatic cancer, parathyroid cancer, penile cancer, Peutz-Jeghers syndrome, pituitary gland tumor, prostate cancer salivary gland cancer, rhabdomyosarcoma, sarcoma, skin cancer (non-melanoma), small bowel cancer, stomach cancer, testicular cancer, thymoma, thyroid cancer, tuberous sclerosis syndrome, Turcot syndrome, unknown primary cancer, uterine cancer, vaginal cancer, Von Hippel-Lindau syndrome, vulvar cancer, Waldenstrom's macroglobulinemia, Werner syndrome, and xeroderma pigmentosa.

In some embodiments, cancers, tumors or other neoplastic conditions or syndromes that may be treated according to the embodiments described herein include, but are not limited to those that are considered to be responsive to radiation therapy (alone or in combination with one or more other treatments), including, but not limited to, brain cancer, breast cancer, cervical cancer, colorectal cancer, endometrial cancer, head and neck cancer, Hodgkin's disease and local extranodal lymphoma, melanoma, ovarian cancer, prostate cancer, rhabdomyosarcoma, retinoplastoma, skin and lip cancer, soft tissue carcinoma, testicular cancer, thyroid cancer, and Wilms tumor.

In some embodiments, the SUMO inhibitor is part of a pharmaceutical composition. The pharmaceutical composition may include one or more SUMO inhibitor and a pharmaceutically acceptable carrier. In some embodiments, the pharmaceutical composition/SUMO inhibitor may be administered in combination with one or more DNA-damaging therapies. In this case, the SUMO inhibitor may sensitize the target cells/cancer cells to the DNA-damaging therapy. Thus, the DNA-damaging therapy is more effective, and allows the use of lower doses, thereby minimizing or eliminating harm to healthy cells.

The term "treat," "treating" or "treatment" as used herein with regard to a condition or disease may refer to preventing a condition or disease, slowing the onset or rate of development of the condition or disease, reducing the risk of developing the condition or disease, preventing or delaying the development of symptoms associated with the condition or disease, reducing or ending symptoms associated with the condition or disease, generating a complete or partial regression of the condition or disease, or some combination thereof.

A "pharmaceutically acceptable carrier" may refer to a pharmaceutically acceptable material, composition, or vehicle that is involved in carrying or transporting a compound of interest from one tissue, organ, or portion of the body to another tissue, organ, or portion of the body. For example, the carrier may be a liquid or solid filler, diluent, excipient, solvent, or encapsulating material, or some combination thereof, described in further detail below. Each component of the carrier must be "pharmaceutically acceptable" in that it must be compatible with the other ingredients of the formulation. It also must be suitable for contact with any tissue, organ, or portion of the body that it may encounter, meaning that it must not carry a risk of toxicity, irritation, allergic response, immunogenicity, or any other complication that excessively outweighs its therapeutic benefits.

Pharmaceutically acceptable carriers are well known in the art and include, for example, aqueous solutions such as water or physiologically buffered saline or other solvents or vehicles such as glycols, glycerol, oils such as olive oil or injectable organic esters, or emulsions such as oil/water emulsions or a triglyceride emulsion, various types of wetting agents, tablets, coated tablets and capsules. A suitable pharmaceutically acceptable carrier may be selected taking into account the chosen mode of administration.

A pharmaceutically acceptable carrier can also contain physiologically acceptable compounds that act, for example, to stabilize or to increase the absorption of the conjugate. Such physiologically acceptable compounds include, for example, carbohydrates, such as glucose, sucrose or dextrans, antioxidants, such as ascorbic acid or glutathione, chelating agents, low molecular weight proteins or other stabilizers or excipients. One skilled in the art will know that the choice of a pharmaceutically acceptable carrier, including a physiologically acceptable compound, depends, for example, on the route of administration of the composition.

In one preferred embodiment, the pharmaceutical carrier may be a liquid and the pharmaceutical composition would be in the form of a solution. In another equally preferred embodiment, the pharmaceutically acceptable carrier is a solid and the pharmaceutical composition is in the form of a powder or tablet.

A solid carrier can include one or more substances which may also act as flavoring agents, lubricants, solubilizers, suspending agents, fillers, glidants, compression aids, binders or table-disintegrating agents, it can also be an encapsulating material. In powders, the carrier is a finely divided solid that is in admixture with the finely divided active ingredient. In tablets, the active-ingredient is mixed with a carrier having the necessary compression properties in suitable proportions and compacted in the shape and size desired. The powders and tablets may contain up to 99% of the active ingredient. Suitable solid carriers include, for example, calcium phosphate, magnesium stearate, talc, sugars, lactose, dextrin, starch, gelatin, cellulose, polyvinylpyrrolidine, low melting waxes and ion exchange resins.

Besides containing an effective amount of the SUMO inhibitors described herein the pharmaceutical compositions may also include suitable diluents, preservatives, solubilizers, emulsifiers, adjuvant and/or carriers.

The compound can be administered in the form of a sterile solution or suspension containing other solutes or suspending agents, for example, enough saline or glucose to make the solution isotonic, bile salts, acacia, gelatin, sorbitan monoleate, polysorbate 80 (oleate esters of sorbitol and its anhydrides copolymerized with ethylene oxide) and the like.

Optimal dosages to be administered may be determined by those skilled in the art, and will vary with the particular compound in use, the severity of the disease state, drug combination(s), reaction sensitivities, and response to therapy. Additional factors depending on the particular subject being treated, including the general health of the subject, the age, weight, gender and diet of the subject, and time and frequency of administration, will result in a need to adjust dosages. Administration of the SUMO inhibitors or pharmaceutical composition thereof may be effected continuously or intermittently. In any treatment regimen, the SUMO inhibitors or pharmaceutical composition may be administered to a patient either singly or in a cocktail containing other therapeutic agents, compositions, or the like, including, but not limited to, tolerance-inducing agents, potentiators and side-effect relieving agents. Preferred potentiators include monensin, ammonium chloride, perhexyline, verapamil, amantadine, and chloroquine. All of these agents are administered in generally-accepted efficacious dose ranges such as those disclosed in the Physician's Desk Reference, 41st Ed., Publisher Edward R. Barnhart, N.J. (1987), which is incorporated herein by reference.

The term "subject" may refer to a human or any other animal, animal model or invertebrate model having a condition, a disease, a cell, or a population of cells that may be treated or used accordance with the methods or with the compounds or compositions described herein. In one embodiment, the subject is a human subject having a disease or condition, such as those described herein. In other embodiments, the subject is any other animal having such a disease or condition, including an animal model used as a research tool that is developed to have the disease or condition or has one or more aspects, attributes, symptoms, or other variables associated with the disease or condition. As such, the SUMO inhibitors described herein may be used as research tools. Such animals or animal models may include, but are not limited to, mice, rats, rabbits, monkeys, pigs, dogs, cats, and birds. In another embodiment the subject may be any other vertebrate or invertebrate model that can be used as a research tool including, but not limited to, a fish (e.g., zebrafish), an insect (e.g., *drosophila*), nematode (e.g., *c. elegans*), mollusk (e.g., *aplesia californicus*).

In some embodiments, a cell or population of cells grown in culture may be used in accordance with the methods or with the compounds or compositions described herein. The cell or population of cells may be derived from or cultured from one or more subjects described above, and may used as a research tool in accordance with the embodiments described herein.

Administering one or more compounds or compositions described herein to the subject, cell or population of cells to investigate one or more mechanisms or other aspects of a condition or disease described herein; or for investigating the effect of one or more compounds or compositions described herein when administered to the cell, population of cells or subject.

The term "route of administration" or "administering" may refer to any administration pathway known in the art, including but not limited to aerosol, enteral, nasal, ophthalmic, oral, parenteral, rectal, transdermal (e.g., topical cream or ointment, patch), or vaginal. "Transdermal" administration may be accomplished using a topical cream or ointment or by means of a transdermal patch. "Parenteral" refers to a route of administration that is generally associated with injection, including infraorbital, infusion, intraarterial, intracapsular, intracardiac, intradermal, intramuscular, intraperitoneal, intrapulmonary, intraspinal, intrasternal, intrathecal, intrauterine, intravenous, subarachnoid, subcapsular, subcutaneous, transmucosal, or transtracheal.

Figure 8:
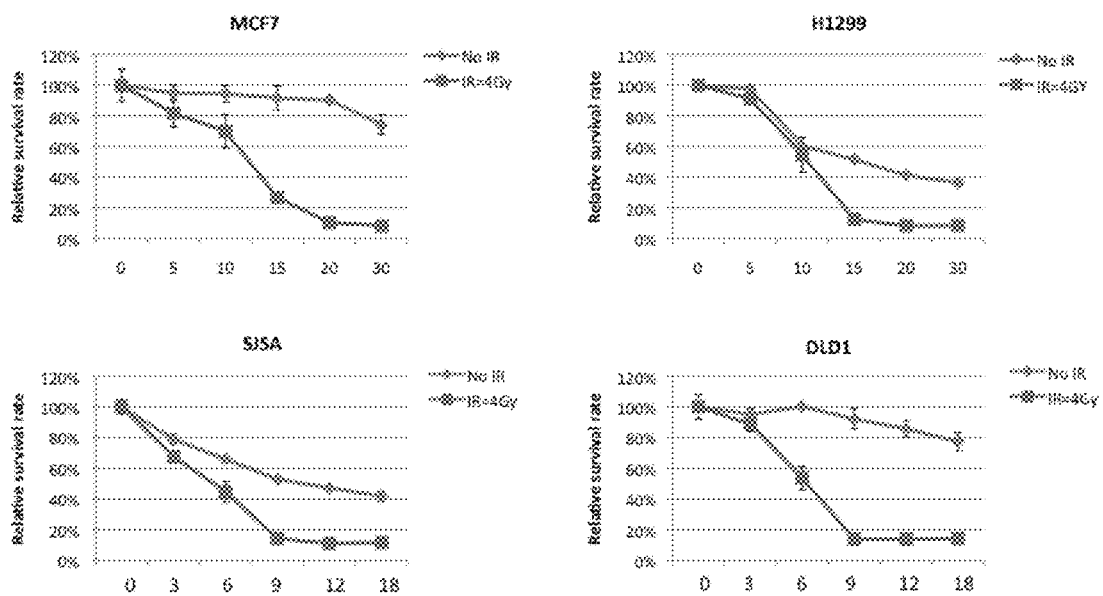
FIG. 8 shows sensitization of breast cancer (MCF7), non-small cell lung cancer (H1299), colorectal cancer (DLD1) and bone cancer (SJSA) cell lines treated with tricyclic SUMOylation inhibitor MLS-0207587 in response to irradiation. The cells were treated with different doses of the drug for 4 hours, followed by irradiation with 4 Gy and incubation for an additional 68 hours. Compared with cells treated only with the drug, the cells treated with both the drug and radiation had a significantly lower survival rate, validating the sensitization effect of the SUMO inhibitor. Cell survival was assessed by MTS assays

The tricyclic SUMO E1 inhibitors characterized herein were not toxic to human hepatocytes at concentrations up to 50 µM (FIG. 9), but induced significant sensitivity to radiation in various cancer cell lines with an $LC_{50}$ of approximately 10 µM or less (see FIG. 8). These findings are particularly important in developing treatment strategies and regimens for increasing the efficacy of radiation therapy, because radiation therapy is delivered locally to tumors, but systemically delivered SUMOylation inhibitors should not cause significant damage to non-irradiated normal cells. Additionally, such inhibitors may be directly applied to rectal cancers locally, an established strategy. Taken together, the studies described herein are significant in that they should lead to development of new paradigms of more effective CRT that are applicable to a wide range of cancers, as well as the first small molecular probes of SUMOylation to elucidate its role in cellular regulation.

Therefore, according to some embodiments, a SUMO inhibitor, alone or as part of a pharmaceutical composition, may be administered in combination with one or more additional therapeutic agents to treat a condition or disease that is associated with altered levels of SUMOylation. In some embodiments, the one or more additional therapeutic agents include one or more DNA-damaging (or "genotoxic") therapy. Administration of the SUMO inhibitor in combination with the one or more genotoxic therapy may increase the efficacy of the one or more additional therapeutic agents, produce a synergistic effect between the inhibitor and the one or more additional therapeutic agents, sensitize cells affected by the condition or disease associated with altered levels of SUMOylation, or a combination thereof.

The term "in combination" or "in combination with" as used herein, means in the course of treating the same disease or condition in a subject using two or more therapies (e.g., agents, drugs, treatment regimens, treatment modalities or a combination thereof) in any order. This includes simultaneous administration (or "co-administration"), administration of a first therapy prior to or after administration of a second therapy, as well as in a temporally spaced order of up to several days apart. Such combination treatment may also include more than a single administration of any one or more therapies. Further, the administration of the two or more therapies may be by the same or different routes of administration.

According to the embodiments described herein, genotoxic therapies that may be administered in combination with the SUMO inhibitors to treat a disease or condition associated with SUMOylation may include, but are not limited to, administration of one or more radiation therapy regimens, administration of one or more DNA-damaging or genotoxic chemotherapeutic agents, or a combination thereof.

Administration of one or more radiation therapy regimens may include any source of ionizing radiation, including x-rays, gamma-rays, alpha particles, beta particles or a combination thereof. These radiation sources may be administered using any sealed source (e.g., external beam radiation therapy, brachytherapy, stereotactic radiation, virtual simulation, 3-dimensional conformal radiation therapy (3DCRT), and intensity modulated radiation therapy (IMRT), image guided radiation therapy (IGRT), particle therapy) or unsealed source (e.g., systemic radioisotope therapy). Examples of radiation sources or imaging methods that may be used according to the embodiments described herein may include, but are not limited to, radiographs, computed tomography (CT), fluoroscopy, positron emission tomography (PET), single photon emission computed tomography (SPECT), radionuclides used alone or with an imaging method such as CT, PET or SPECT (e.g., Barium-133, Cadmium-109, Cobalt-57, Cobalt-60, Iodine-131, Iodine-131-methaiodobenzylguanidine (MIBG), Europium-152, Manganese-54, Sodium-22, Zinc-65, Technetium-99m, Polonium-210, Strontium-90, Thallium-204, Carbon-14, Lutetium-177, Yttrium-90, Phosphorus-32, Strontium-89, Samarium-153, Radium-223, Bismuth-213), radioimmunotherapy (e.g., Yttrium ($^{90}$Y) ibritumomab tiuxetan, Iodine ($^{131}$I) tositumomab)

In some embodiments, the one or more genotoxic chemotherapeutic agents that may be administered in combination with the SUMO inhibitors described herein include, but are not limited to, (i) alkylating agents, platinum analogues or other alkylating-like or nonclassical alkylating agents (e.g., carmustine, streptozocin, busulfan, chlorambucil, ifosfamide, cyclophosphamide, thiotepa, lomustine, cisplatin, carboplatin, mechlorethamine, chloambucil, oxaliplatin, uramustine, melphalan, nedaplatin, satraplatin, triplatin tetranitrate, procarbazine, altretamine and temozolomide); (ii) intercalating agents (e.g., doxorubicin, epirubicin, danorubicin, daunomycin, proflavine, ethidium bromide, berberine, thalidomide and dactinomysin); (iii) topoisomerase inhibitors (etopocide, topotecan, irinotecan, amsacrine. camptothecin, lamellarin D, teniposide, aurintricarboxylic acid and HU-331); and (iv) cytotoxic antibiotics (e.g., actinomycin. valrubicin, idarubicin, bleomycin, plicamycin and mitomysin).

Having described the invention with reference to the embodiments and illustrative examples, those in the art may appreciate modifications to the invention as described and illustrated that do not depart from the spirit and scope of the invention as disclosed in the specification. The examples are set forth to aid in understanding the invention but are not intended to, and should not be construed to limit its scope in any way. The examples do not include detailed descriptions of conventional methods. Such methods are well known to those of ordinary skill in the art and are described in numerous publications. Further, all references cited above and in the examples below are hereby incorporated by reference in their entirety, as if fully set forth herein.

Example 1

SUMO-1, -2, and -3 Expression in Colorectal Cell Lines

SUMO1, -2, and -3 mRNA levels were measured in the colorectal cancer cell lines HCT116 and HT29, which represent the majority of colorectal cancer types (e.g., they have chromosome instability or are mismatch repair deficient). Specifically, gene expression levels were measured for both SUMO E1 subunits (SAE1 and SAE2); SUMO E2 (Ubc9); the SUMO E3 ligases PIAS1, PIAS2, PIAS3, PIAS4, RanBP2, MMS21; and de-SUMOylation enzymes SENP1, 2, 3, 4, 5, 6, and 7. Expression levels in HCT116 and HT29 were compared to those in normal colon mucosa. GAPDH expression levels were used as a control.

Significantly higher mRNA levels were observed for most SUMOylation-related genes (Table 2). The two E1 subunits (SAE1 and SAE2) were the most elevated, with significantly greater increases in expression than Ubc9 (E2) and PIAS3 (E3). This is significant because Ubc9 and PIAS3 were both previously found to be elevated in many cancer types (Wang 2004; Mo 2005).

TABLE 2

SUMO-1, -2, and -3 expression in colorectal cell lines

| Gene | HCT116 (RPKM*) | HT29 (RPKM*) | Avg. control (RPKM*) | Fold-change in HCT116 vs. control | Fold-change in HT29 vs. control |
|---|---|---|---|---|---|
| E1 (SAE1) | 103.75 | 108.24 | 17.34 | 5.98 | 6.24 |
| E2 (SAE2) | 60.09 | 91.02 | 6.13 | 9.80 | 14.85 |
| E3 (PIAS3) | 6.64 | 7.95 | 1.53 | 4.34 | 5.20 |
| E2 (Ubc9) | 113.94 | 101.28 | 29.31 | 3.89 | 3.46 |
| GAPDH | 2100.40 | 2313.06 | 1094.17 | 1.92 | 2.11 |

RPKM: reads per kilobase per million mapped

Immunohistochemistry studies were performed on stage II and III colorectal tumor specimens and matched normal tissues. Consistent with the mRNA expression results, SAE1 and SAE2 were the most significantly overexpressed SUMOylation-related proteins in tumor specimens relative to the matched normal tissues (Wiatrek et al. Differential expression of small ubiquitin-like modifier family of proteins in patients with colorectal adenocarcinoma; ASCO Abstract, 2011, which is hereby incorporated by reference, as if fully set forth herein; see http://www.asco.org/ascov2/Meetings/Abstracts?&vmview=abst_detail_view&confide=103&abstra ctl D=71189).

SAE1 and SAE2 levels were found to be the only SUMO proteins with increased expression in resistant tumors after CRT in comparison to pretreatment biopsy samples. To validate this clinical observation, a radioresistant HCT116 line was developed by irradiating (2Gy/day) a mouse xenograft tumor for one week, cutting out the xenograft and using it to start a primary culture, then irradiating the culture (2Gy/day) for another week. Comparison of the radioresistant HCT116 line with the parental line showed that the SAE2 level was approximately 3-fold greater in the radioresistant line. The level of other SUMO enzymes did not change significantly. The results of these studies indicate that upregulated SUMO E1 levels are correlated with a patient's response to CRT, and that the E1 level increases after CRT in resistant tumors.

Example 2

Development of Tricyclic SUMO E1 Inhibitors

Through the Molecular Library Probe Production Center Network (MLPCN), at least 300,000 compounds were screened using a TR-FRET method, an ALPHASCREEN™ method or both, and tested for their ability to inhibit SUMOylation of a target protein via SUMO E1 or SUMO E2. The assays were based on SUMOylation of the target protein RanGAP1, which is a protein that is efficiently SUMOylated with only the SUMO E1 and E2 enzymes, and does not use E3 ligases. A fluorescence resonance energy transfer (FRET) assay was the primary assay followed by a chemoluminescence-based secondary assay using ALPHA screen to eliminate false positive hits. Then, the hits were screened by a poly-ubiquitination assay using ubiquitin, ubiquitin E1, Ubc5 and Apc11 to eliminate inhibitors not specific to SUMOylation. The screening identified a potent family of SUMOylation inhibitors based on a tricyclic scaffold.

Figure 20A:
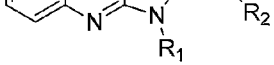
Figure 20A:
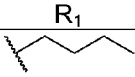
Figure 20A:
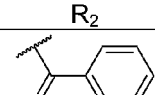
Figure 20A:
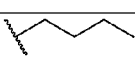
Figure 20A:
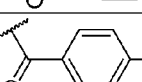
Figure 20A:
Figure 20A:
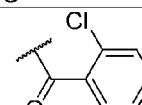
Figure 20A:
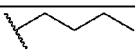
Figure 20A:
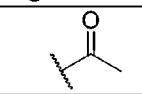
Figure 20A:
Figure 20A:
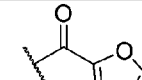
Figure 20A:
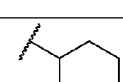
Figure 20A:
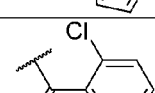
Figure 20A:
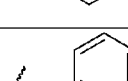
Figure 20A:
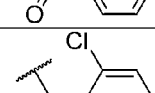
Figure 20A:
Figure 20A:
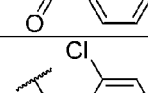
Figure 20A:
Figure 20A:
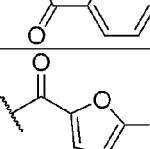
Figure 20C:
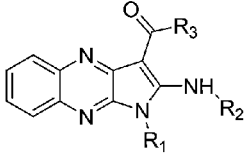
Figure 20C:
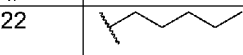
Figure 20C:
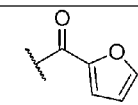
Figure 20C:
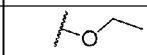
Figure 20C:
Figure 20C:
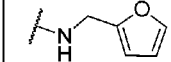
Figure 20C:
Figure 20C:
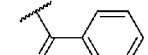
Figure 20C:
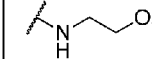
Figure 20C:
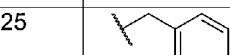
Figure 20C:
Figure 20C:
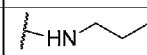

Approximately 200 small molecule inhibitors of SUMO E1 were identified according to these methods. These inhibitors can be classified into ten compound scaffolds, three of which were selected for further characterization based on having a higher potency as compared to other molecule inhibitors that were identified. Exemplar studies to determine the efficacy and potency of the inhibitors are illustrated in FIGS. 10-13. Several SUMO E1 inhibitors based on these scaffolds were synthesized, purchased, or both for further characterization (FIGS. 20A-C)

Figure 3:
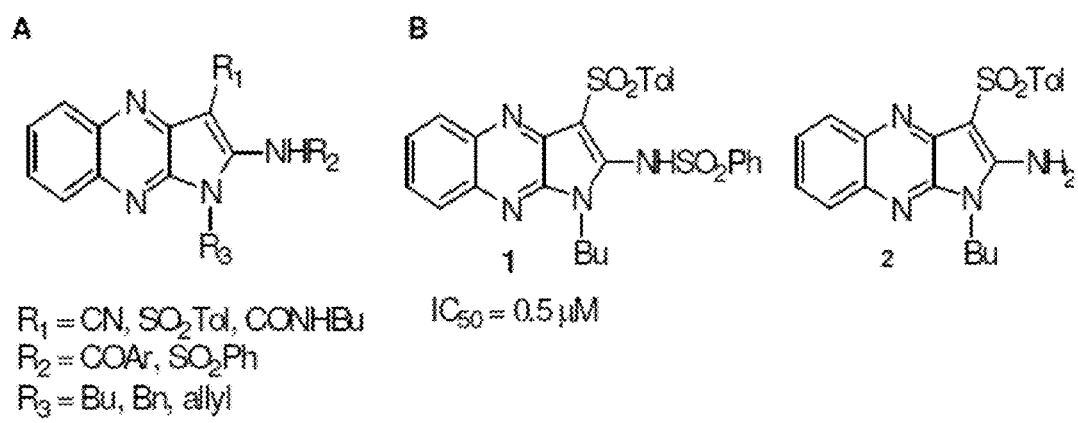
FIG. 3 illustrates the characterization of the tricyclic probe used to generate SUMO enzyme inhibitors. (A) Quinoxaline analogs synthesized and tested. (B) Compound 1 is one of the most potent analogues from this series. Compound 2 is a similar compound, but lacks the Ph-group and is not inhibitory to the SUMO E1. Therefore, it is used as a control.
Figure 4:
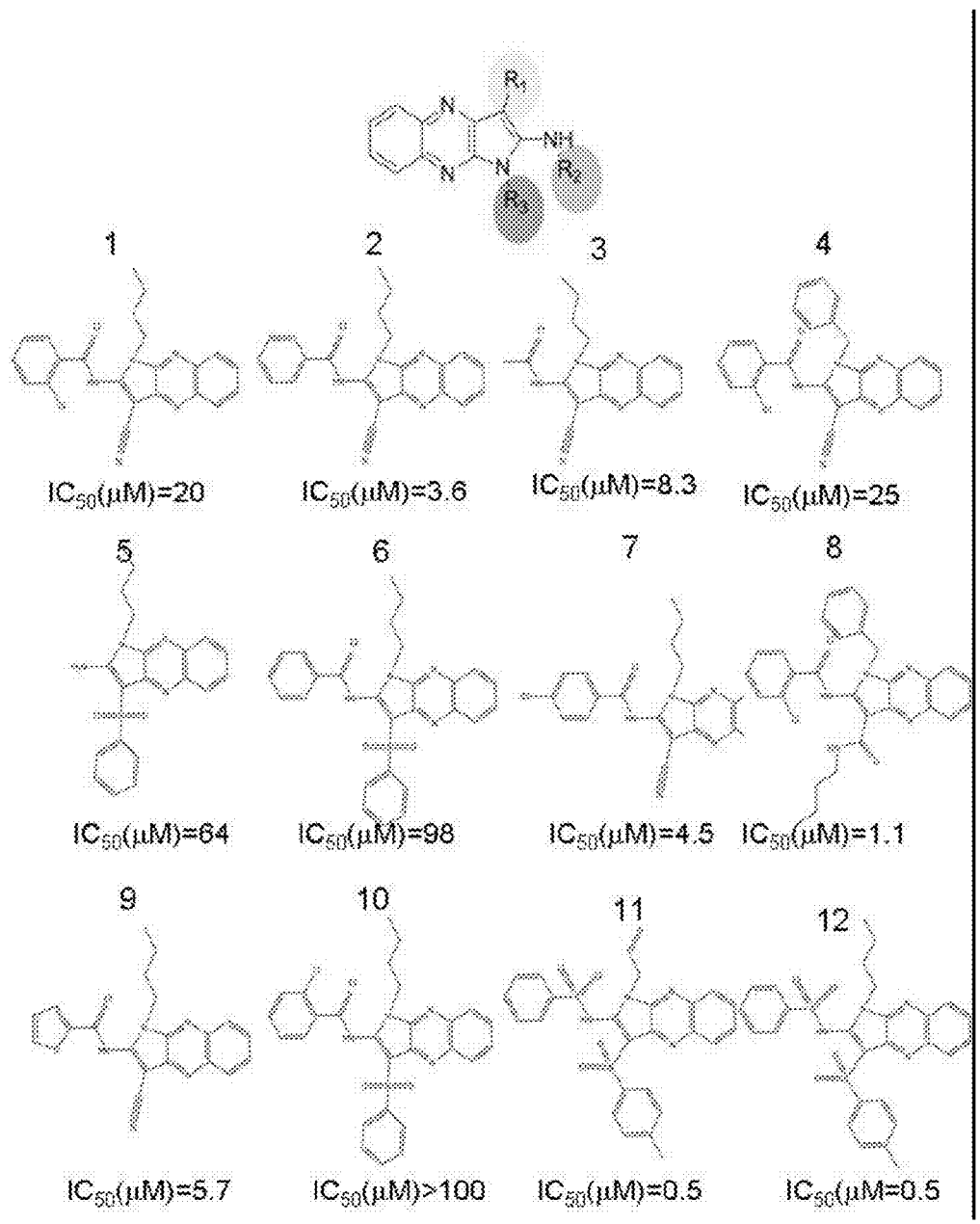
FIG. 4 shows analogues of the first class of SUMO E1 inhibitor to explore the three R-groups. The analogues and their IC50 values in inhibiting the SUMO E1 in biochemical assays are indicated below each analogue.
Figure 5:
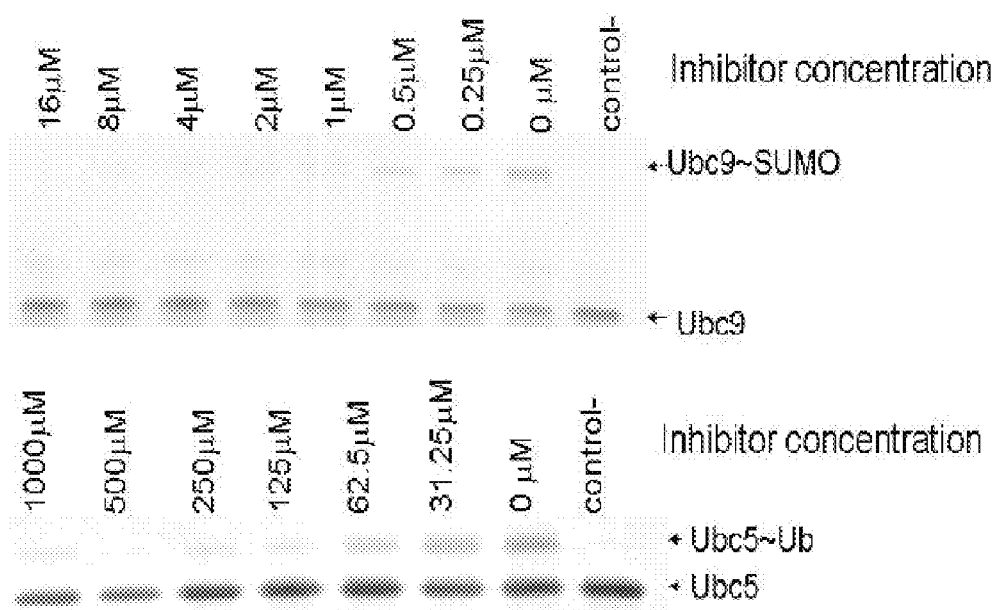
FIG. 5 shows that compound 1 has a highly selective inhibitory effect on SUMOylation and on a SUMO E1 enzyme, while showing that the ubiquitination pathway is not inhibited. The upper panel shows formation of the Ubc9-SUMO thioester, which is catalyzed by the SUMO E1, at the indicated concentrations of inhibitor. The $IC_{50}$ is approximately 0.5 µM. In contrast, the inhibitor has an $IC_{50}$ value >100-fold higher for inhibiting the ubiquitin E1 during formation of Ubc5-ubiquitin thioester (lower panel). All protein levels were calibrated using amino acid analysis and that the visual difference of Ubc9 versus Ubc5 level is due to Coomassie staining differences.
Figure 6:
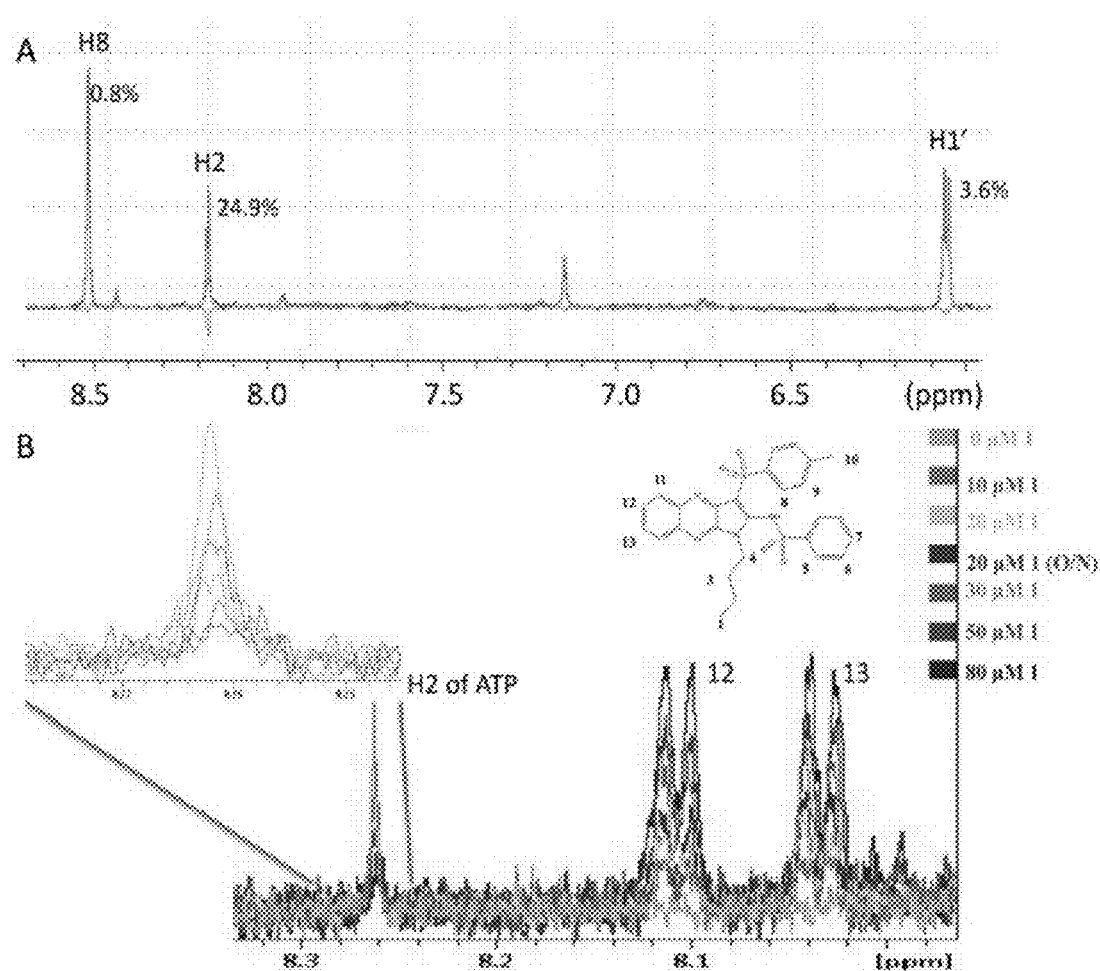
FIG. 6 shows STD NMR experiments of ATP and compound 1 in the presence of the SUMO E1. In (A), ATP spectra with assignments indicated, and the percentage of STD effects indicated for each resonance. Red spectrum indicates 2 s saturation at −30 ppm (control), blue spectrum (underneath red) indicates 2 s saturation of protein signals at 0 ppm, and green spectrum (bottom) indicates the difference between the red and blue spectra. H2 experiences the largest STD effect followed by H1', consistent with the X-ray structure (Lois & Lima 2005). In (B), STD of 60 µM ATP upon titration of compound 1 at the concentrations indicated to the right. The corresponding STD spectra are color-coded as indicated to the right. A region of the spectrum covering H2 of ATP and H12 and H13 from the compound are shown, with the H2 signal of ATP expanded in the inset. The compound has strong STD effects, and titration of 1 reduced ATP STD effect in a concentration dependent manner, indicating strong competition with ATP binding. The titration data was used to estimate $K_d$ of the compound.

One of the selected scaffolds is a tricyclic scaffold containing the 1H-pyrrolo-[2,3-b]quinoxalines (FIG. 3A). Approximately 30 compounds with this scaffold were screened for their ability to inhibit SUMO E1. The structures of twelve of these compounds are set forth in FIG. 4 and Table 1 above, along with the in vitro $IC_{50}$ of each compound for SUMO E1. Table 1 shows representative compounds of the SUMOylation inhibitors derived from the singleton scaffold. Of the screened compounds, quinoxaline 1 (FIG. 3B) was identified as one of the most potent SUMO E1 inhibitor identified and selected as a lead compound (identified herein as MLS0437113), with an in vitro $IC_{50}$ of approximately 0.25-0.5 µM and a Kd of approximately 180 nM (FIG. 5, upper panel and FIG. 6). In addition, quinoxaline 1 is more than 100-fold more selective for SUMOylation than for the homologous ubiquitin E1, suggesting that it does not inhibit SUMO E1 through non-specific mechanisms (FIG. 5). Another compound from this scaffold group, quinoxaline 2 (FIG. 3B), does not inhibit SUMO E1. Quinoxaline 2 is structurally very similar to quinoxaline 1, but lacks a phenyl group. This suggests that this phenyl group is important to SUMO E1 inhibition. Since quinoxaline 2 did not exhibit SUMO E1 inhibition, it was used as a control for further studies.

Example 3

Synthesis of Tricyclic SUMO E1 Inhibitors

The tricyclic SUMOylation inhibitor compounds described herein may be synthesized using any suitable method known in the art, including according to the representative protocols shown below.

Protocol 1: Generation of Compound D According to Scheme 1.

2-tosylacetonitrile B (0.108 g, 0.5 mmol) was transferred to a 250 ml round-bottom flask and dissolved in 10 ml DMSO. Cesium carbonate (0.245 g, 0.75 mmol) was added to the reaction mixture followed by addition of 2,3-dichloroquinoxaline (0.1 g, 0.5 mmol). The reaction mixture was stirred at room temperature overnight. The crude reaction mixture was diluted with 50 ml ethyl acetate and washed with 1N HCl (2×50 mL) and brine solution (2×50 mL). The organic layer was collected and the solvent was removed under reduced pressure to yield the crude product C (2-(3-chloroquinoxalin-2-yl)-2-tosylacetonitrile) which was taken to the next step without further purification. Compound C (0.150 g, 0.42 mmol) was transferred to a microwave vessel containing 1 ml butyl amine. The reaction mixture was subjected to microwave irradiation at 70° C. for 30 min. The resultant crude reaction mixture was purified using column chromatography to yield compound D as shown in Scheme 1 (0.105 g, 64% yield). $^1$H NMR (500 MHz, Chloroform-d) δ 8.24-8.15 (m, 3H), 7.93 (dd, J=8.2, 1.5 Hz, 1H), 7.58 (dddd, J=25.1, 8.3, 6.9, 1.6 Hz, 2H), 7.29 (d, J=8.1 Hz, 2H), 6.57 (bs, 2H), 4.19 (t, J=7.4 Hz, 2H), 2.38 (s, 3H), 1.86-1.73 (m, 2H), 1.48-1.38 (m, 2H), 0.99 (t, J=7.3 Hz, 3H). ESI (m/z): 395 (M+H$^+$).

Scheme 1:

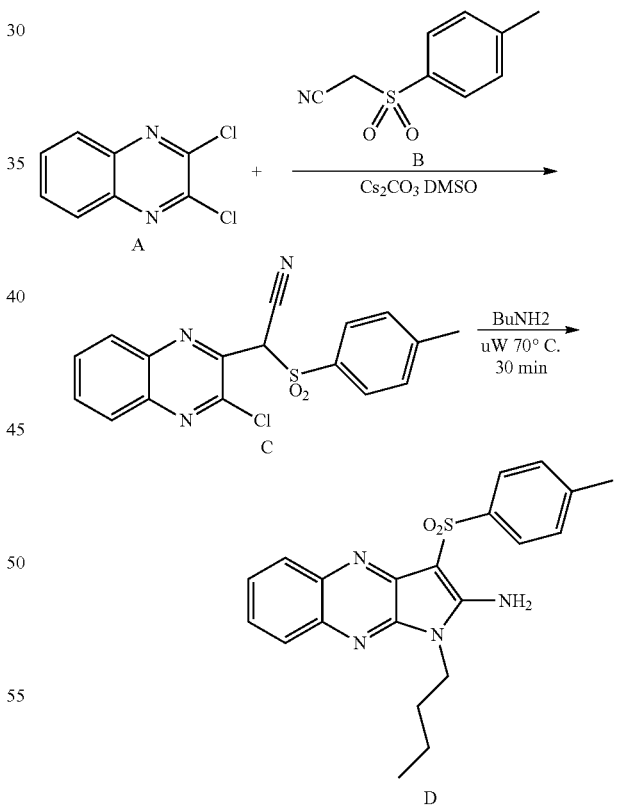

Protocol 1: Generation of Compound E According to Scheme 2.

Compound D (250.0 mg, 0.633 mmol) generated in Scheme 1 was dissolved in 5 ml dry THF at 0° C. followed by addition of NaH (22.0 mg, 0.951 mmol). The resulting reaction mixture was stirred for 5 minutes followed by addition of benzoyl chloride (89.0 mg, 0.633 mmol). The progress of the reaction was monitored using TLC and after completion of reaction (~30 min) the reaction mixture was quenched by addition of NH$_4$Cl solution. The crude reaction mixture was diluted with 50 ml ethyl acetate and washed with 1N HCL (2×50 mL) and brine solution (2×50 mL). The organic layer was collected and concentrated under reduced pressure to yield the crude product which was purified using column chromatography to furnish compound E as shown in Scheme 2 (145.0 mg, 46.0% yield). $^1$H NMR (500 MHz, Chloroform-d) δ 10.48 (s, 1H), 8.40-8.28 (m, 1H), 8.23-8.14 (m, 2H), 8.15-8.07 (m, 3H), 7.79-7.70 (m, 3H), 7.66 (t, J=7.6 Hz, 2H), 7.25 (d, J=8.2 Hz, 2H), 4.59 (t, J=7.4 Hz, 2H), 2.35 (s, 3H), 1.95-1.79 (m, 2H), 1.34-1.23 (m, 2H), 0.91 (t, J=7.4 Hz, 3H). ESI (m/z): 500 (M+H$^+$).

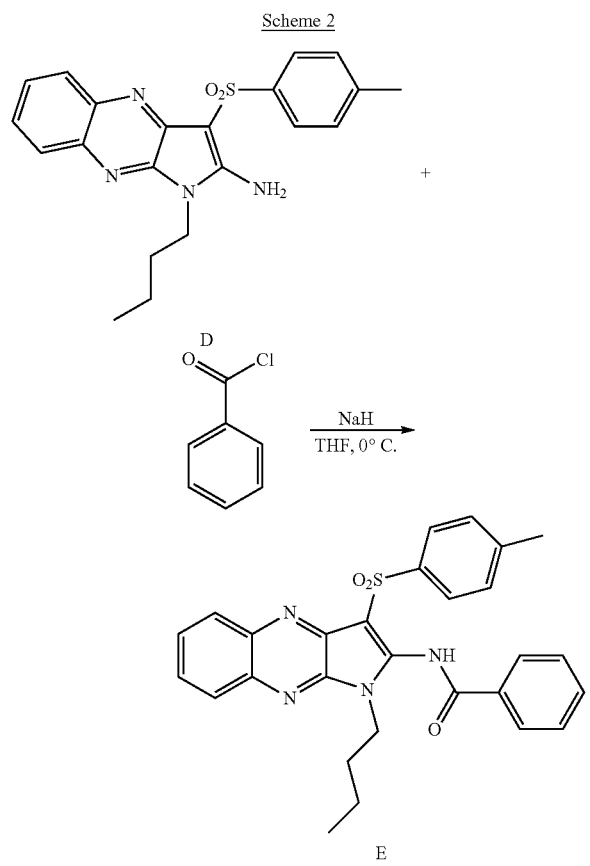

Protocol 2: Generation of Compound D According to Scheme 3.

Malononitrile B (0.66 g, 10 mmol) was dissolved in 20 ml DMSO. Cesium carbonate (4.87 g, 15 mmol) was added to the reaction mixture followed by addition of 2,3-dichloroquinoxaline (2.0 g, 10 mmol). The reaction mixture was stirred at room temperature overnight. The crude reaction mixture was diluted with 50 ml ethyl acetate and washed with 1N HCl (2×50 mL). the mixture was extracted with ethyl acetate (2×80 mL). The combined organic layer was washed with brine solution (2×50 mL). The organic layer was collected and the solvent was removed under reduced pressure to yield the crude product C 2-(3-chloroquinoxalin-2-yl)malononitrile (2.0 g) which was used in the next step without further purification. Compound C (0.22 g, 1 mmol) was transferred to a microwave vessel containing 1 ml butyl amine. The reaction mixture was subjected to microwave irradiation at 70° C. for 30 min. The resultant crude reaction mixture was purified using column chromatography to yield compound D as shown in Scheme 3 (0.20 g, 86% yield). ESI (m/z): 266 (M+H$^+$).

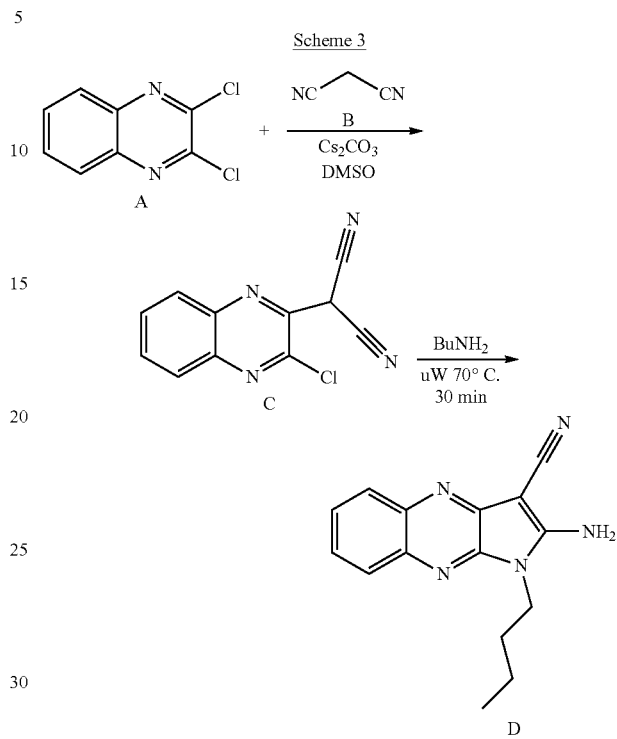

Protocol 2: Generation of Compound E According to Scheme 4.

Compound D (200.0 mg, 0.76 mmol) was dissolved in 9 ml dry THF at 0° C. under nitrogen atmosphere followed by addition of NaH (27.0 mg, 1.13 mmol). The resulting reaction mixture was stirred for 5 minutes followed by addition of acetyl chloride (107.0 mg, 0.76 mmol). The progress of the reaction was carefully monitored using TLC and after completion of reaction (~30 min) the reaction mixture was quenched by addition of NH$_4$Cl solution (30 mL). The crude reaction mixture was extracted with ethyl acetate (3×30 mL). The combined organic layer was washed with brine solution (50 mL). The organic layer was dried over anhydrous sodium sulfate, filtered and concentrated under reduced pressure to yield the crude product which was purified using column chromatography to furnish compound E as shown in Scheme 4 (170.0 mg, 61% yield) as yellow solid. ESI (m/z): 370 (M+H$^+$).

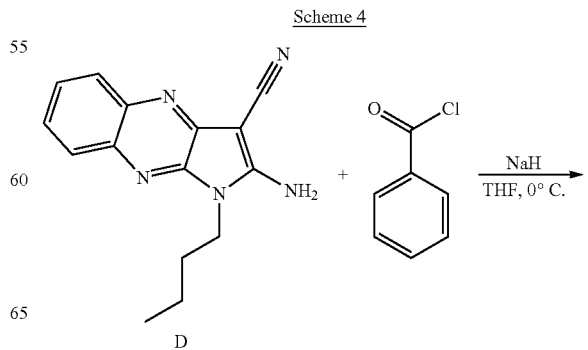

-continued

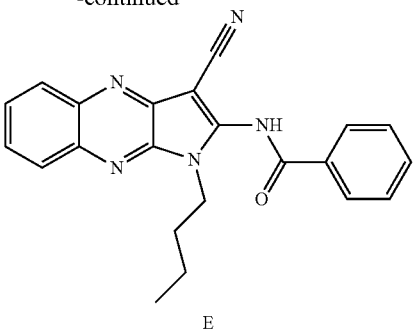

E

An additional synthesis strategy was developed for generating tricyclic scaffold derivatives, including quinoxaline. The synthesis route for quinoxaline 1 is set forth in Scheme 5.

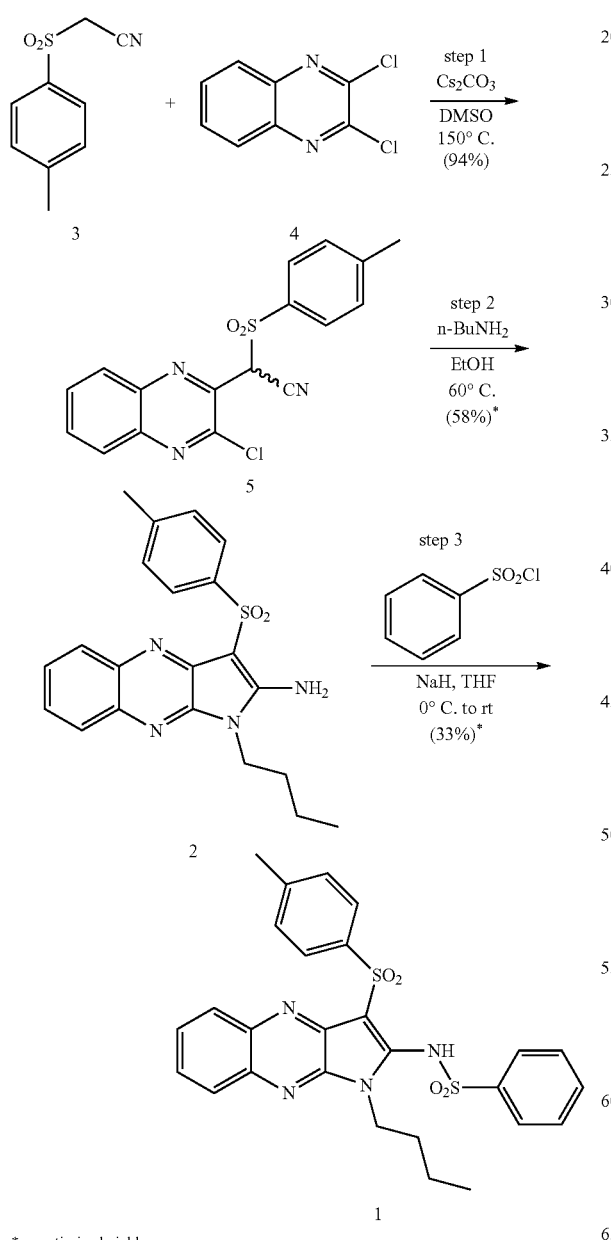

* unoptimized yields

Briefly, upon heating commercially available nitrile 3 and 2,3-dichloroquinoxaline (4) an excellent yield of monosubstituted quinoxaline derivative 5 was obtained. This reaction can be carried out on a multigram scale. Treatment of 5 with n-butylamine for 3 days led to displacement of chloride and cyclization, which afforded quinoxaline 2 in moderate yields. Sulfonylation of quinoxaline 2 gave quinoxaline 1.

The roles of $R_1$, $R_2$, and $R_3$ on the quinoxaline core may also be evaluated by introducing different substituents. This can be readily done at different points in the synthesis. Potential substitutions include various stabilized carbonanions in step 1, different alkyl and aryl amines in step 2, and different acylating groups (including sulfonyl and phosphoryl) in step 3.

Alternatively, to evaluate the importance of the large quinoxaline template, smaller analogs such as 2,3-dichloro-2,3-pyrazinedicarbonitrile (7) in place of quinoxaline 4 may be prepared and evaluated. Following the chemistry outlined in Scheme 6, this may lead to pyrrolo[2,3-b]pyrazine analog 8 for direct comparison with quinoxaline analog 1. The use of dichloropyrazine 7 has recently been shown to undergo monosubstitution with carbanionic nucleophiles (Chekmarev 2006). Scheme 6:

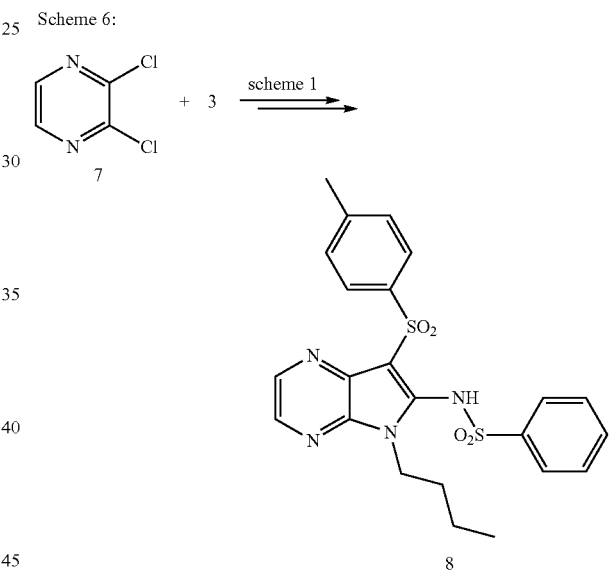

It is likely that the benzene moiety of the quinoxaline ring system is important for binding and specificity. To investigate the role of this structural unit, the benzene ring may be derivatized with various hydrophobic and hydrogen bond donor/acceptor groups as represented by $R_4$ (Scheme 7). This synthetic route is amenable for the proposed modifications. Modifications may be introduced at the front end of the synthetic scheme, since many mono-, di- and tri-substituted o-phenylenediamines 9 are readily available either through commercial sources or known procedures (Ohmori 1997).

Scheme 7:

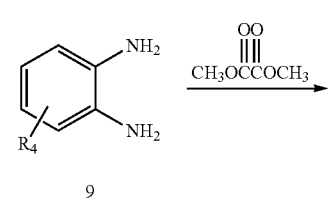

-continued

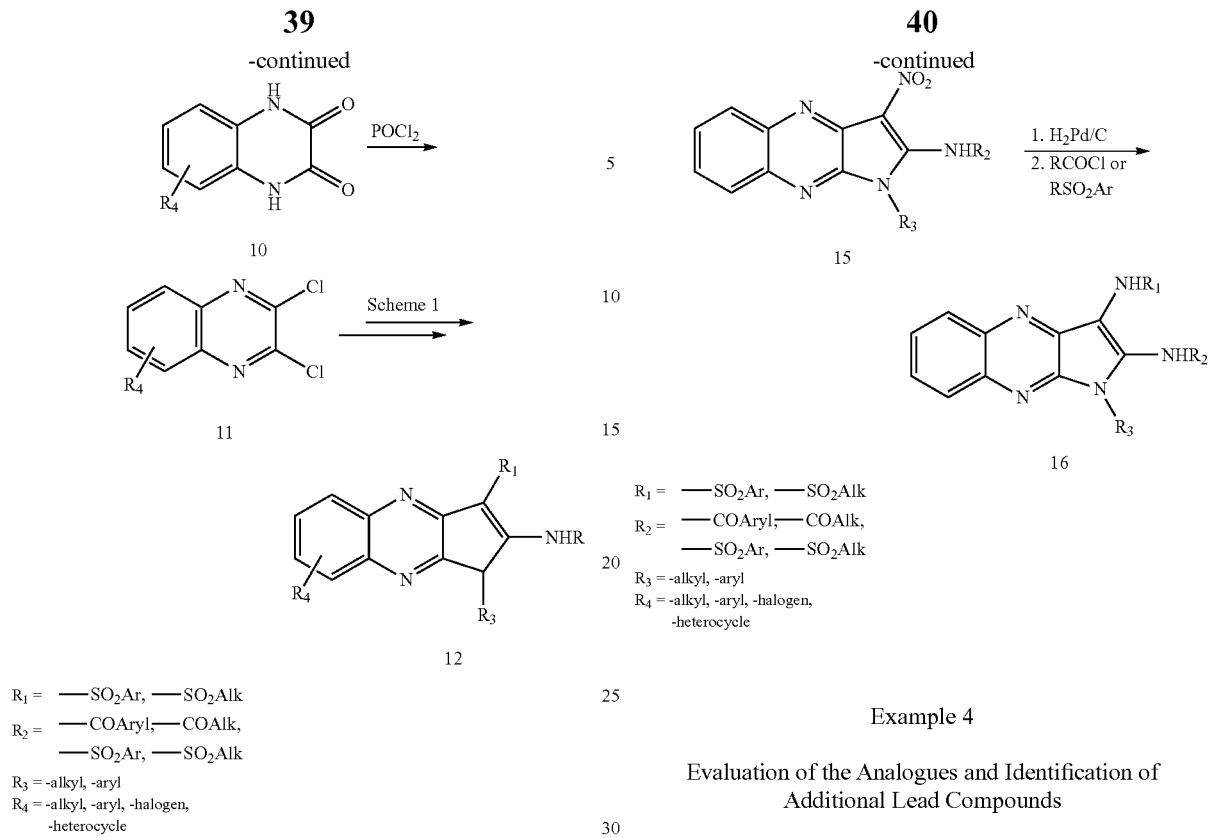

R₁ = —SO₂Ar, —SO₂Alk
R₂ = —COAryl,—COAlk,
    —SO₂Ar, —SO₂Alk
R₃ = -alkyl, -aryl
R₄ = -alkyl, -aryl, -halogen,
    -heterocycle The effects of substituting the sulfone moiety can be evaluated by introducing an amide group during the initial aryl substitution reaction by converting dichlororquinoxaline 4 to intermediate 12 using cyanoacetonitrile (Scheme 8). Cyclization with amine and acylation or sulfonylation would produce a nitro derivative 15. Reduction of the nitro group followed by acylation or sulfonylation would give functionally substituted quinoxaline 16.

Scheme 8:

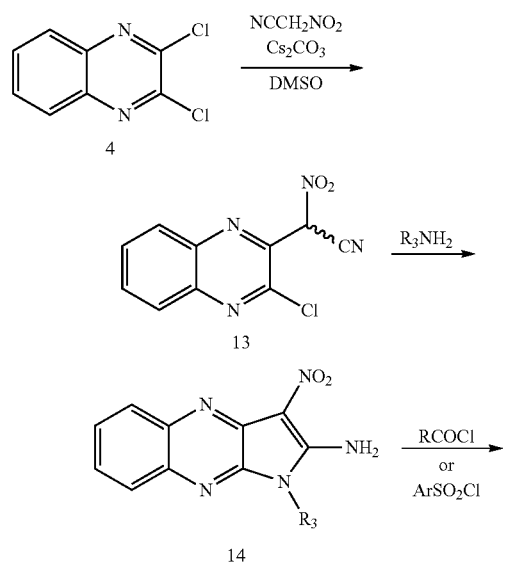

R₁ = —SO₂Ar, —SO₂Alk
R₂ = —COAryl,—COAlk,
    —SO₂Ar, —SO₂Alk
R₃ = -alkyl, -aryl
R₄ = -alkyl, -aryl, -halogen,
    -heterocycle

Example 4

Evaluation of the Analogues and Identification of Additional Lead Compounds

SUMOylation inhibitor analogues described herein may be tested using various biochemical assays, as described in the Examples herein, to examine their efficacy and selectivity for SUMOylation. In addition, NMR studies described in FIG. 6 and elsewhere herein, may be carried out in conjunction to investigate changes of the binding mode on the E1. SUMO E1 specific inhibitors with more potent enzymatic inhibitory effect than compound 1 or improved stability may be selected based on potency (e.g., $K_d$ or $IC_{50}$ values) for further in vivo testing. in vivo testing will start with Tricyclic compound 1 described herein.

Investigation of the structural mechanism of inhibition. As discussed above, tricyclic compounds described herein bind and compete for the ATP-binding pocket. Using the binding epitope of the inhibitor derived from NMR saturation transfer difference (STD) studies (FIG. 6), the program HADDOCK (de Vries et al. 2010; van Dijk et al. 2005; Dominguez et al. 2003) may be used to determine whether said inhibitor can fit into the ATP-binding pocket based on guided docking calculations of the protein-inhibitor complex. Further, previously described methods (Tatham et al. 2003; Wang & Chen 2010; Wang et al. 2010; Want et al. 2009; Wang et al. 2007; Thatham et al. 2005; Tatham et al.2003a; Liu et al. 2002; Liu et al. 1999) may be used to determine whether the inhibitor binds to an allosteric site instead of or in addition to directly competing with ATP. A structural allosteric effect would likely affect the binding of other substrates (SUMO and Ubc9) in addition to or instead of ATP.

Various forms of the E1 have been crystallized, including the free enzyme, E1-ATP complex, E1-ATP-SUMO complex, E1 in complex with an ATP analogue, and E1 in complex with a SUMO-adenylate mimic (Lois & Lima 2005, Olsen et al. 2010), therefore, existing crystallization conditions may be used initially to obtain crystals. Then, the inhibitors may be soaked into the crystals. Additionally, the E1-inhibitor complex may be co-crystallized using one or more conditions identified by a crystallization robot that can screen for conditions that allow crystallization of a protein. Alternatively, Nuclear Overhauser Effects (NOEs) between an inhibitor and SUMO E1 may be used to obtain the intermolecular distances between the protein and the inhibitor in solution, as previously described (Pellecchia et al. 2002). In addition to Met-methyl groups, the methyl groups of Ile, Leu and Val as may be labeled as previously described (Religa & Kay 2010). The intermolecular distance constraints may then be used to determine structural calculations of the protein-inhibitor complexes, as described previously (Wang et al. 2007). NMR linewidths of the bound ligands and protein sidechains at the binding interface also provide information on the dynamics at the binding pocket.

Accurate estimation of binding affinities of protein-ligand complexes is still a challenge in the computational field. Therefore, medicinal chemistry efforts may be used in parallel with structural studies and rational design. The structural insights on the ligand-binding pocket of E1 may be incorporated into the lead compound design. For example, identification of hydrogen-bonding donors or acceptors in the pocket are matched by incorporating complimentary hydrogen-bond acceptor or donor groups in the ligand. The side of the ligand that does not form direct contacts with the enzyme is then derivatized to improve pharmacokinetic and pharmacodynamic properties.

The medicinal chemistry methods described herein in combination with binding mode and inhibition analysis provides structure-activity relationship (SAR) information and an understanding of how the SUMO E1 enzyme is inhibited by small molecules. In addition, the medicinal chemistry effort may identify additional inhibitors with higher potency and/or higher in vivo stability than those already described. Given the important roles of SUMOylation in cancer, development of neurodegenerative diseases and viral infection (Sarge et al. 2009), as well as the lack of any inhibitors targeting SUMOylation enzymes, the small molecular inhibitors of SUMO E1 described herein should have a significant impact on the treatment of these diseases as well as in biomedical research for determining the pathogenic pathways involved in the development of these life-threatening diseases. Lead compounds may be used for preclinical and early phase clinical studies to examine how SUMOylation can be targeted for the development of innovative therapies for these life-threatening diseases.

In some aspects, an inhibitor may bind to more than one surface of the SUMO E1, as evidenced by NMR line-width changes of the inhibitors with addition of the SUMO E1 (Reibarkh et al. 2006). In such cases, structure determination may be carried out under the appropriate inhibitor: E1 stoichiometry.

Example 5

NMR Characterization of Tricyclic SUMO E1 Inhibitors

NMR saturation transfer difference (STD) experiments showed that quinoxaline 1 bound E1 in a reversible manner and competed with the binding of ATP. Using 80 µM ATP and 2 µM E1 in the presence of 0.4 mM $Mg^{2+}$, the STD of ATP was observed (FIG. 6A). Addition of 30 µM quinoxaline 1 to the above sample resulted in a reduction in the STD of ATP by more than 60% and observation of a significant STD effect of the inhibitor, indicating that the inhibitor competes efficiently with ATP with less than half the concentration of ATP. Following these results, a more detailed competitive STD experiment was conducted (FIG. 6B). Previous studies indicate that the $K_d$ of ATP binding to E1 in the presence of $Mg^{2+}$ is approximately 0.2 µM (Tokgoz 2006), and thus based on the competitive STD data (FIG. 6B) the inhibitor-enzyme dissociation constant ($K_d$) was estimated to be approximately 180 nM using the established method (Mayer 2001).

Example 6

Inhibition of SUMOylation by Tricyclic Inhibitors

Figure 7:
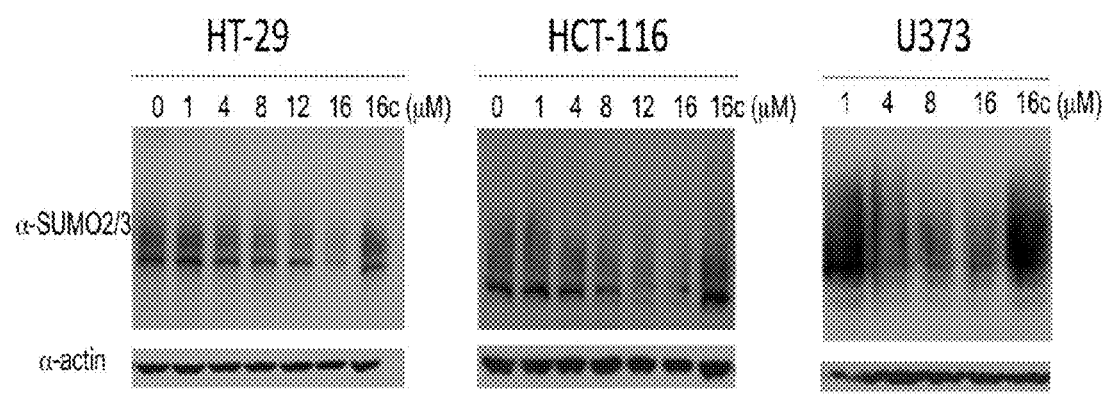
FIG. 7 illustrates that compound 1 inhibits global SUMOylation in a dose-dependent manner. Western blots (probed with anti-SUMO2/3 antibodies) of cell lysates from HT29, HCT116 and U373 cells treated with compound 1. SUMO2/3 modifies many proteins as poly-SUMO chains, and is detected as high molecular weight smears. 16c indicates the control compound 2 used at concentrations of 16 µM.

To investigate whether quinoxaline 1 specifically inhibits SUMO E1 in cells, the structurally similar inactive analog (quinoxaline 2) was used as a control. Quinoxaline 1 or 2 was added to cell culture media at various concentrations for 18 hours, after which SUMOylated proteins were detected using anti-SUMO antibodies. Quinoxaline 1 inhibited SUMOylation in a dose-dependent manner in colorectal cell lines (HCT116 and HT29) as well as other cancer cell lines (glioblastoma U373) (FIG. 7). Importantly, quinoxaline 2 did not exhibit any inhibitory effects even at 16 µM, a concentration at which quinoxaline 1 inhibited global SUMOylation by more than 80 percent. Thus, quinoxaline 1 has potent and specific inhibitory effects in various cancer cell lines.

Example 7

Sensitization of Cancer Cells to Genotoxic Stress

Figure 9:
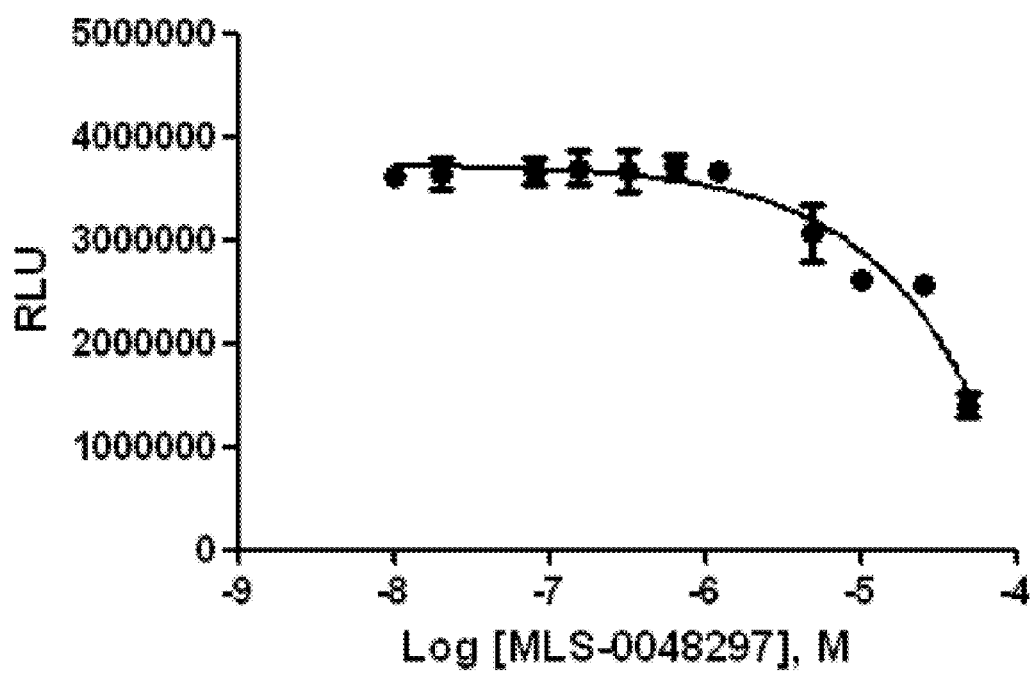
FIG. 9 illustrates the toxicity of the SUMO inhibitor on normal human liver cells. Immortalized human hepatocytes, Fa2N-4 cells (XenoTech) were seeded at ~50-60K cells/well, and incubated with a range of concentrations (0.01-50 µM) 1, in duplicate, for 24 hrs at 37° C., 5% $CO_2$. Cell viability was determined by cellular ATP levels using the Luminescence ATP Detection Assay System (Tecan).
Figure 10:
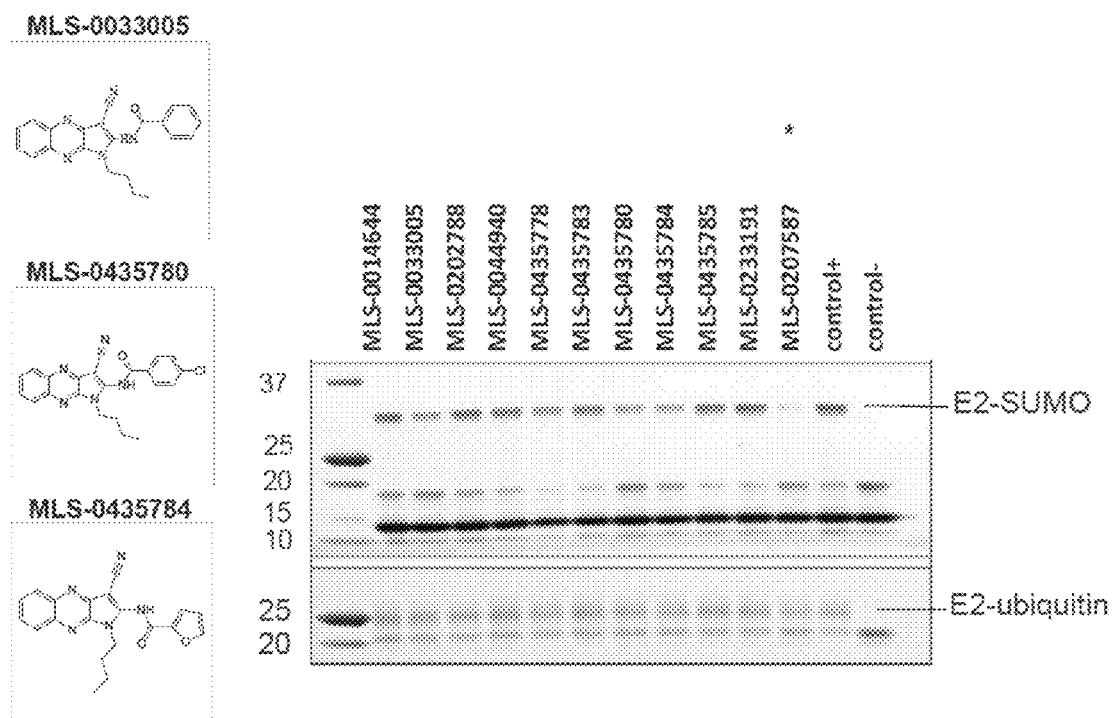
FIG. 10 illustrates a representative assay to determine the efficacy of SUMO inhibitors generated from the tricyclic probe shown in FIG. 5.
Figure 11:
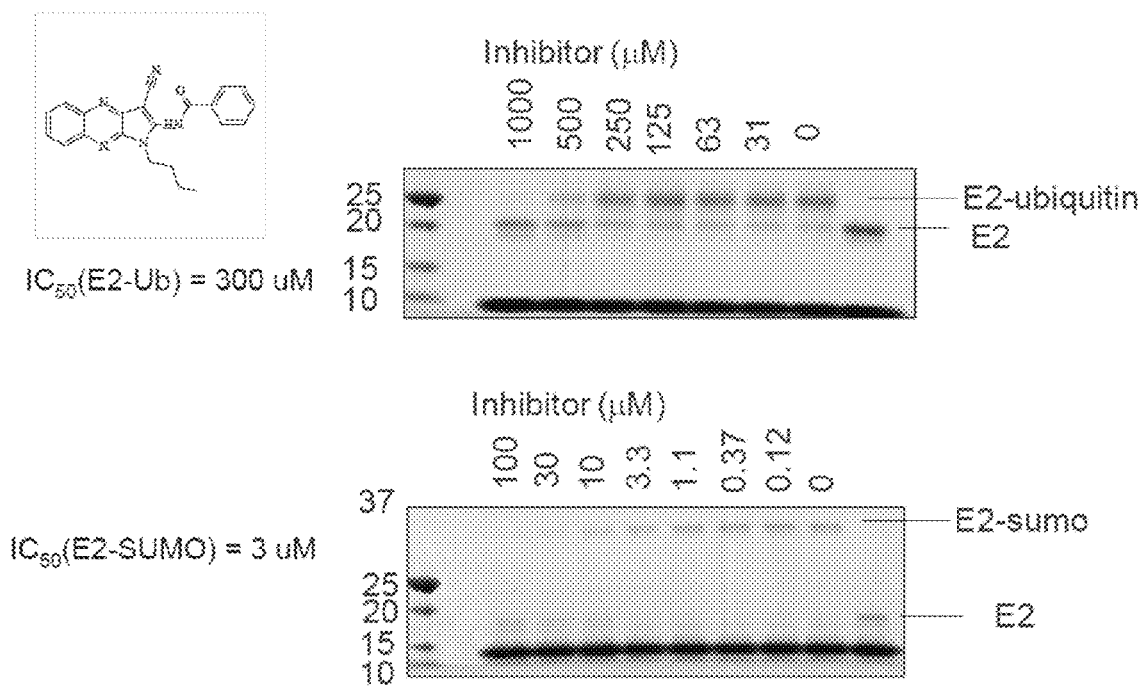
FIG. 11 illustrates a dose-response in thioester formation assays to determine the effective dose of a candidate tricyclic SUMO inhibitor (MLS-0033005).
Figure 12:
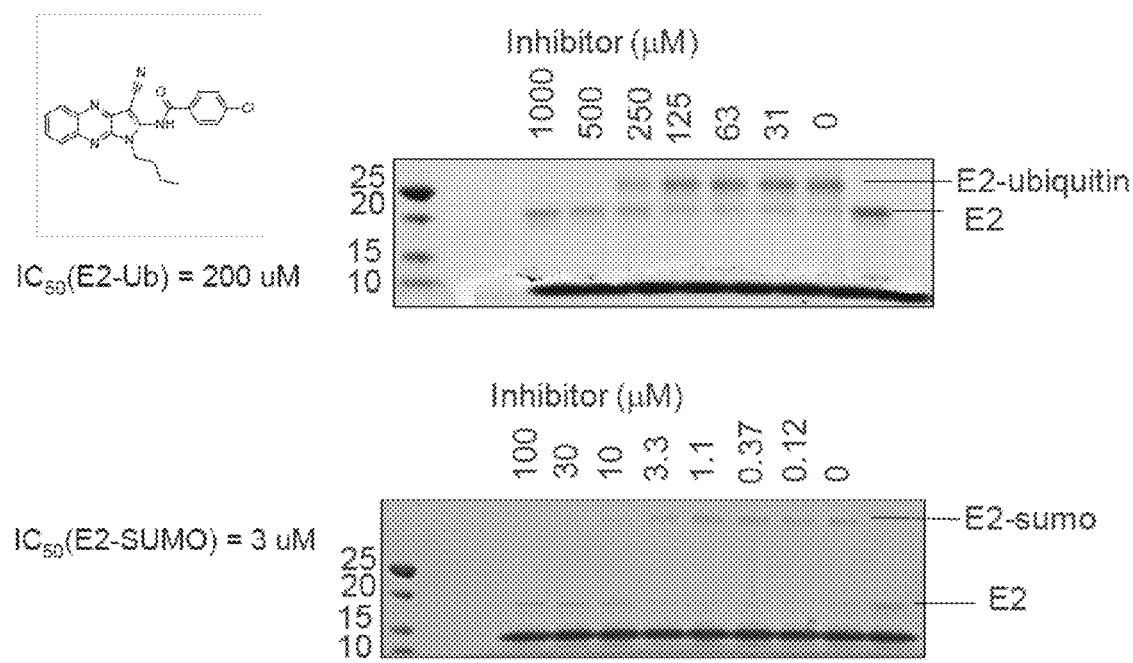
FIG. 12 illustrates a dose-response in thioester formation assays to determine the effective dose of a candidate tricyclic SUMO inhibitor (MLS-0435780).
Figure 13:
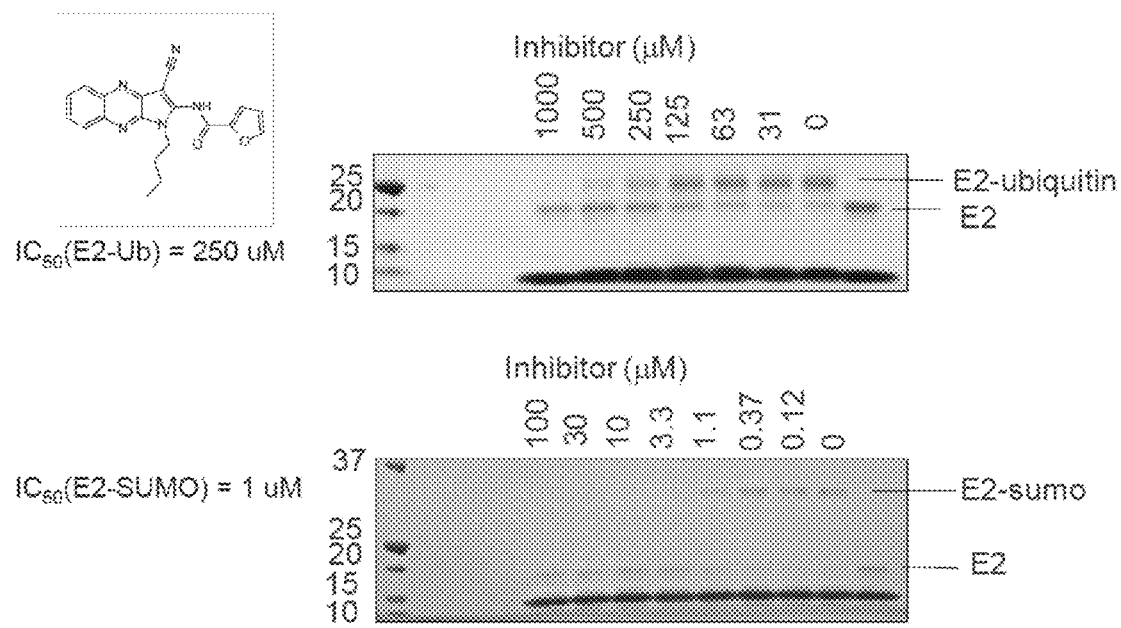
FIG. 13 illustrates a dose-response in thioester formation assays to determine the effective dose of a candidate tricyclic SUMO inhibitor (MLS-0435784).

Quinoxaline 1 was added to cultures of various cancer cell lines for 4 hours, after which cells were irradiated at 4 Gy. Forty-eight hours after irradiation, cell viability was measured by MTS assay. Addition of the inhibitor significantly enhanced the sensitivity of tested cancer cell lines to radiation (FIG. 8). The inhibitor also induced some toxicity in selected cancer cell lines at a lower $IC_{50}$ than that which caused toxicity in immortalized human hepatocytes Fa2N-4 (no toxicity was detected with concentrations up to 50 µM; FIG. 9). Quinoxaline 2 did not cause toxicity or demonstrated sensitization effects in any of the tested cell lines, consistent with its lack of inhibitory effect to SUMOylation.

Evaluate SUMOylation inhibitors in cancer cell lines. Because the SUMO E1 enzyme is more crucial to survival of cells with certain genetic backgrounds (Luo et al. 2009), lead compound 1 may be submitted for screening of a panel of 60 cancer cell lines at NIH to identify other genetic backgrounds in which the SUMO E1 is more critical to viability. The results may be further validated by siRNA knockdown and molecular biological studies.

The extent to which the SUMOylation inhibitors can enhance cancer cell sensitivity to DNA-damaging chemotherapeutic drugs, including doxorubicin, 5-fluorouracil, camptosar and eloxatin, may be determined and is compared to that of chemotherapeutic drugs that do not induce DNA damage in colorectal cancer cell lines HT-29, HCT-116 and DLD1. Compounds with in vitro efficacy similar to or greater than that of compound 1 may be assessed for their effects on sensitizing colorectal cancer cells to radiation, as described in FIG. 8 (MTS assay). Additional studies may be carried out with different combination of chemotherapeutic agents with radiation and with and without SUMO E1 inhibitor. In addition, using compound 1, and inhibitors developed using the methods described in the Examples above, more sensitive cytotoxicity assays may be carried out using DIMSCAN, a semiautomatic fluorescence-based digital image microscopy system that quantifies relative total viable cell numbers in tissue culture with high sensitivity and linearity over a range >4 logs of cytotoxicity assessment (Keshelava et al. 2005).

Clonogenic assays may be performed to examine long-term survival, as previously described (Li et al. 2010). The toxicity of the lead inhibitors identified in the Examples above to normal cells may be tested using immortalized human hepatocytes (Fa2N-4 cells) to ensure that the lead compounds do not have high toxicity to normal cells.

Evaluation of the Molecular Mechanism of the Inhibitors.

Figure 2:
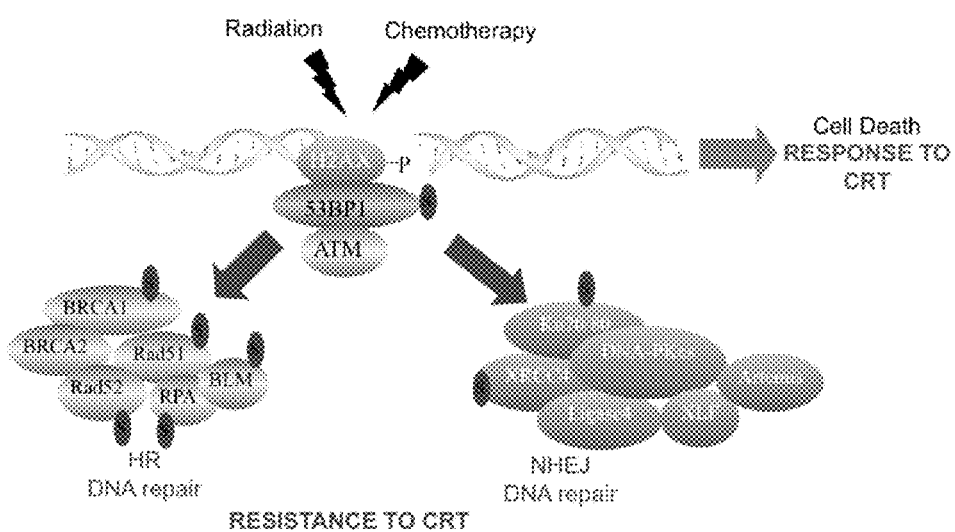
FIG. 2 illustrates the role of SUMOylation in response to a DNA double-strand break in response to chemo- and radiation therapy (CRT). A schematic of current knowledge of the DNA damage signaling and repair pathways for DSBs is shown. Red ovals mark proteins known to be modified by SUMO-1, SUMO-2 or SUMO-3. SUMOylation not only controls events upstream of the repair pathways, but is important for both HR and NHEJ repair pathways. Although not depicted here, SUMOylation is also important for single-stranded DNA repair, regulating nuclease stability, inhibition of the formation of cruciform DNA upon damage, and nucleotide base excision repair.

To further elucidate the role of the SUMOylation inhibitors in sensitizing cancer cells to ionizing radiation, compound 1 (FIG. 3) and additional lead compounds identified according to the methods described above may be analyzed to determine how they affect early events in the DNA damage response, such as phosphorylation of histone H2AX and the kinases ATM, ATR and DNA-PKcs, and recruitment of 53BP1 and BRCA1 to DNA damage sites that are critical for DNA DSB repair. Further, the mechanism of how SUMOylation inhibitors inhibit the various pathways used for repair of DNA DSBs (FIG. 2), as described in the Examples above and in previous studies (Li et al. 2010). Whether the inhibitors induce apoptosis or inhibit cell cycle progression by fluorescence-activated flow cytometry analyses (FACS) and annexin V staining, which is an indicator of an early apoptotic stage, and propidium iodide staining, an indicator of plasma membrane permeability that develops at a later apoptotic stage may also be investigated. These studies may be used to elucidate the mechanism by which the inhibitors inhibit growth of cancer cells and enhance cancer cell sensitivity to CRT.

Investigation of the Effects of SUMOylation Inhibitors in Genotoxic Stress in Xenograph Models.

Compound 1 and the effective derivatives generated according to the methods described in the Examples above will be tested in cellular assays using colorectal cancer-bearing xenograft models or primary cancer tissues from clinical cancer tissue samples. Mice are administered drugs by oral gavage, intraperitoneal injection, intravenous injection, or osmotic pump methods. Tumor growth is monitored by animal body mass scoring and direct measurement of the size of tumors. To examine the effect of the inhibitors on enhancing sensitivity of xenograft tumors to radiation, multiple-fraction radiation may be delivered at ~2.0 Gy per day for 5 consecutive days, and the radiation beam will be focused only on the tumor. To examine the effect of the inhibitors on sensitization to chemotherapeutic drugs, the drugs (i.e. doxorubicin, 5-fluorouracil, camptosar or eloxatin) that show a synergistic effect with SUMO E1 inhibitor in cellular studies should be given together with the SUMO E1 inhibitor. Mice injected with vehicle control (or compound 2) or one of the candidate SUMOylation inhibitors will be compared. Along with these studies, the concentration of the inhibitors in tumors can be determined over the same period of time to obtain pharmacokinetic data. SUMOylation levels in the tumor lysates will be analyzed at the same time to establish the direct link between inhibitor treatment and SUMOylation.

SUMO E1 inhibitors should sensitize CRT in these preclinical studies using animal models. Such results will establish a new paradigm in targeting SUMO E1 as a new cancer therapeutic strategy. In addition, screening the panel of 60 cancer cell lines using the inhibitor may elucidate new genetic interactions of SUMO E1 with genes whose mutations cause cancer. It is not expected that these inhibitors would have significant toxicity to normal tissues, because lead compound 1 did not cause significant toxicity to human hepatocytes, even when used at concentrations up to 50 μM (FIG. 9).

Despite the $K_d$ of 1 being approximately 180 nM, global SUMOylation was inhibited with μM concentrations of the inhibitor. This discrepancy is likely due to 1) the long life spans of some SUMOylated proteins and 2) the high enzymatic activity of E1 and reversible inhibition by the compound, so that a small fraction of active E1 can catalyze significant SUMOylation. This scenario also explains the low toxicity of the inhibitor to normal cells that is not as dependent on SUMOylation as some cancer cells (Luo et al. 2009).

Example 8

Derivative 1 Also Possess Anti-HIV Activities

Figure 14:
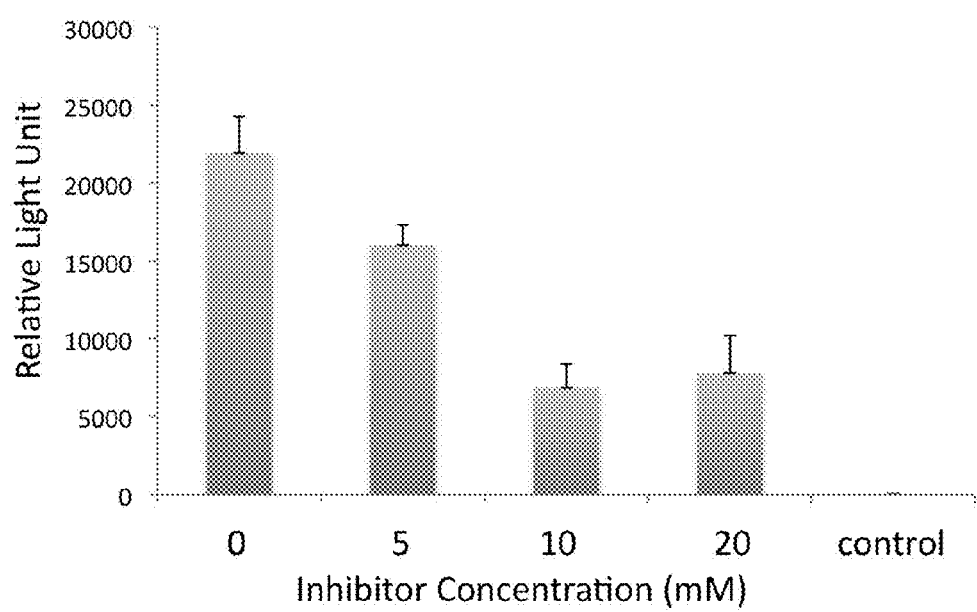
FIG. 14 shows that tricyclic SUMO inhibitor compound 1 (quinoxaline) inhibits HIV infection in a dose-dependent manner.
Figure 15:
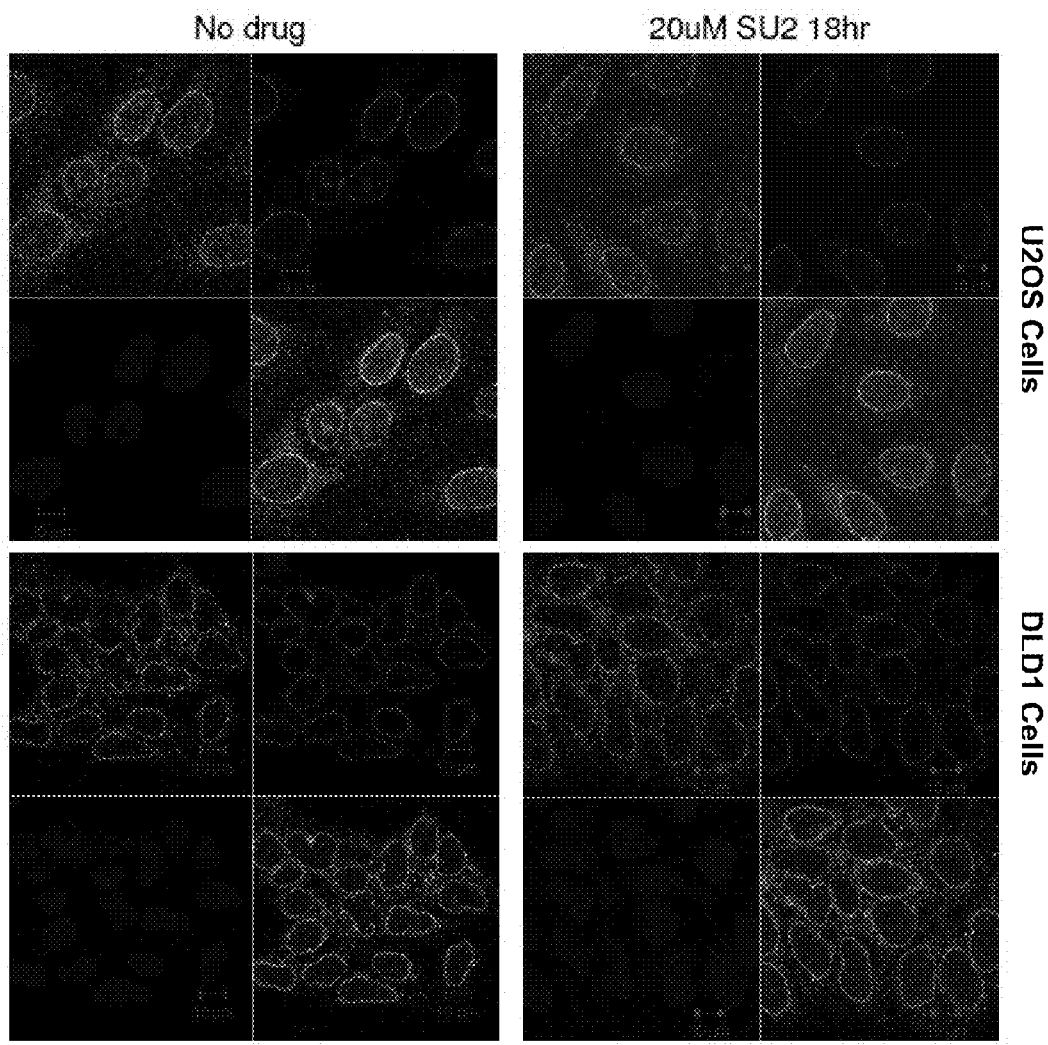
FIG. 15 illustrates that MLS-0207587 (shown as SU2) does not disrupt stable SUMOylation in U20S cells and DLD1 cells (Green: RanGAP1; Red:RanBP2). Cells were treated with the compound at indicated concentration for 18 hours, and then localization of RanGAP1 and RanBP2 was detected by immunohistochemistry. Nuclei are stained with DAPI.
Figure 16:
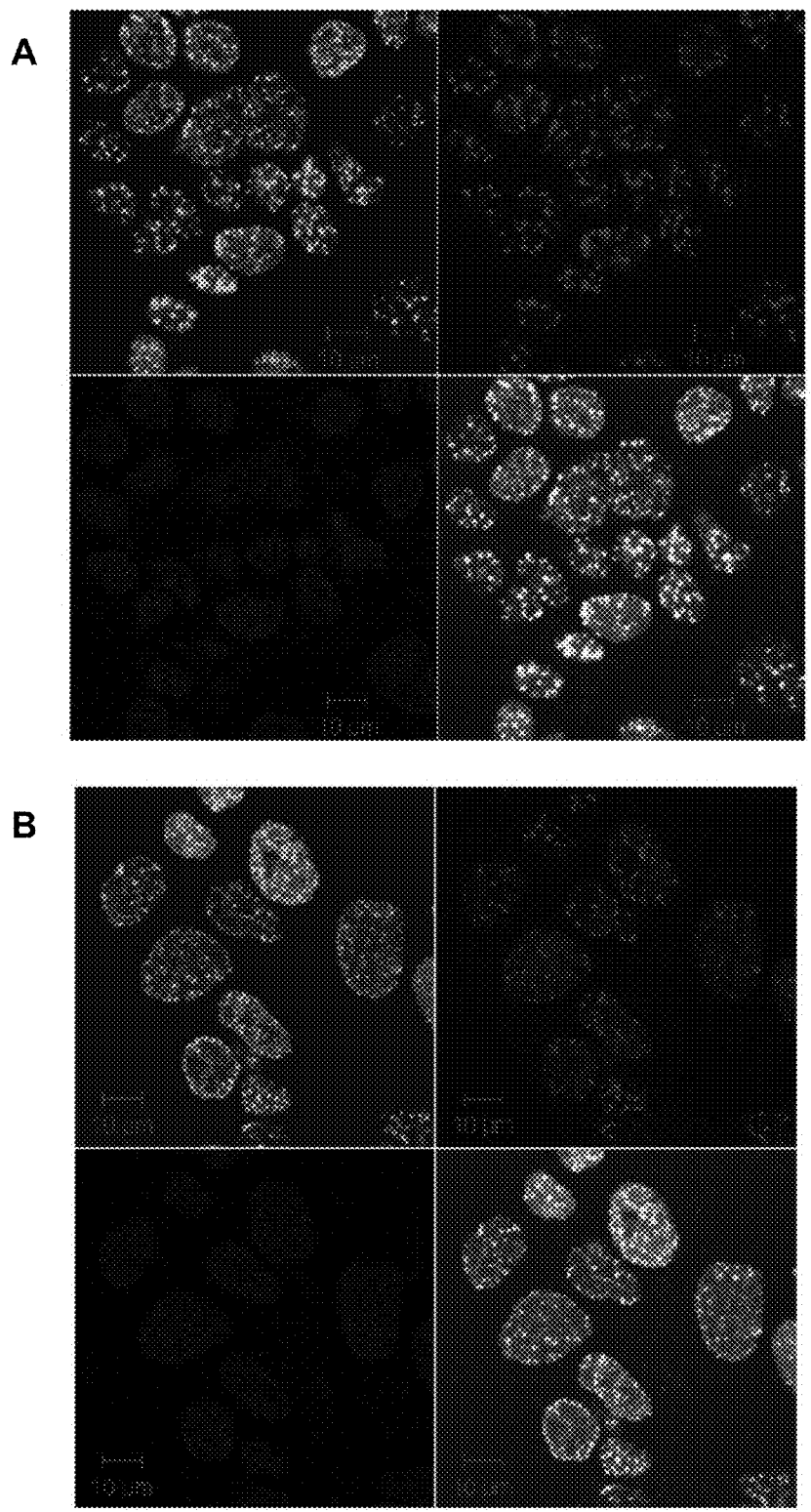
FIG. 16 illustrates that MLS-0207587 inhibits 53BP1 colocalization with γH2AX at DSB sites in IR-treated DLD1 cells. (A) shows colocalization of 53BP1 and γH2AX (lower left panel) in untreated irradiated DLD1 cells, while (B) shows a lack of colocalization as illustrated by a lack of foci when the DLD1 cells are treated with 20 µM MLX-0207587 for 18 hours followed by irradiation at 1 Gy followed by 1 hour recovery period. (Green: γH2AX; Red: 53BP1).
Figure 17:
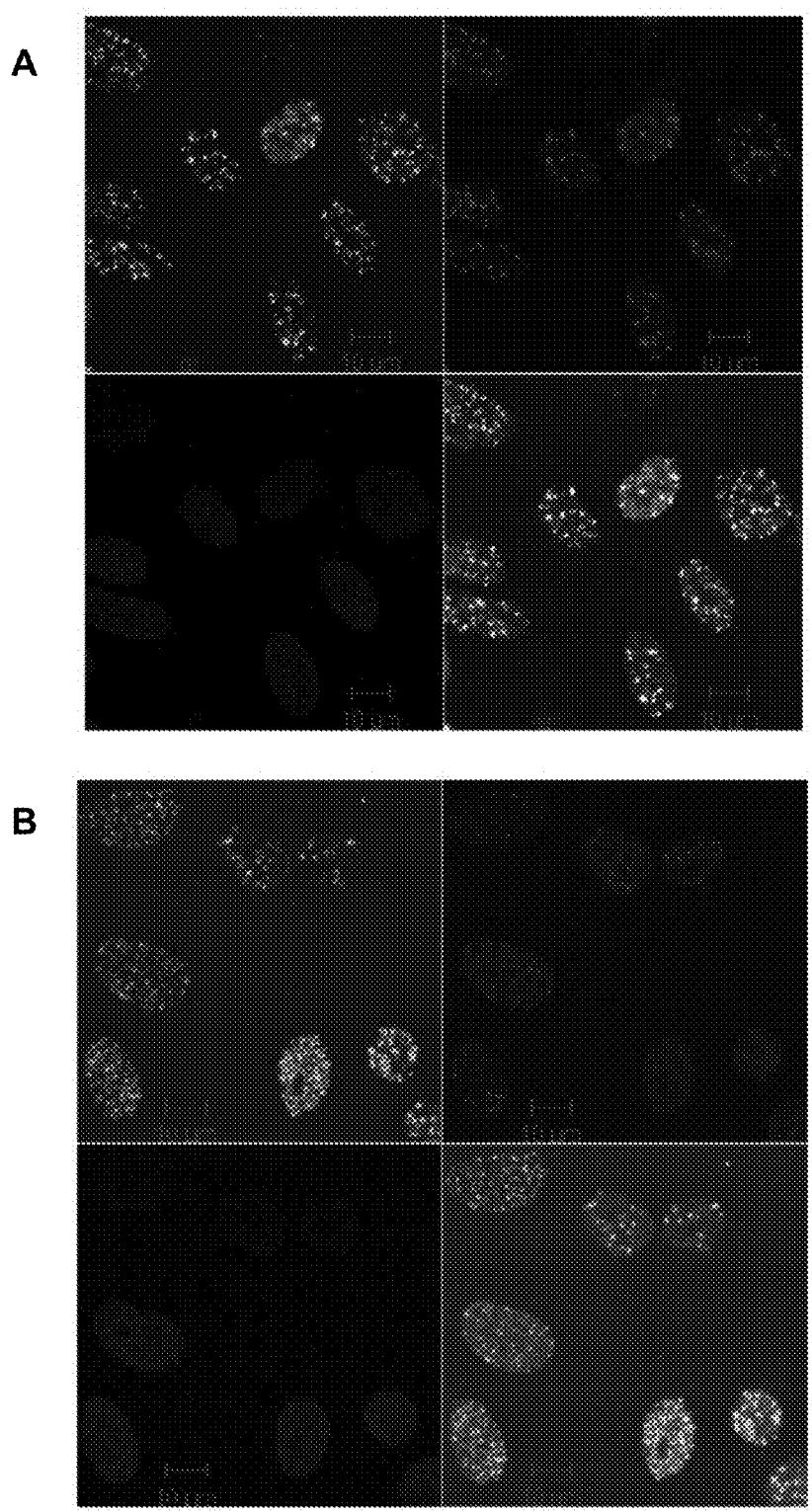
FIG. 17 illustrates that MLS-0207587 inhibits 53BP1 colocalization with γH2AX at DSB sites in IR-treated U20S cells. (A) shows colocalization of 53BP1 and γH2AX (lower left panel) in untreated irradiated U20S cells, while (B) shows a lack of colocalization as illustrated by a lack of foci when the U20S cells are treated with 20 µM MLS-0207587 for 18 hours followed by irradiation using 1 Gy, followed by 1 hour recovery. (Green: γH2AX; Red: 53BP1).
Figure 18:
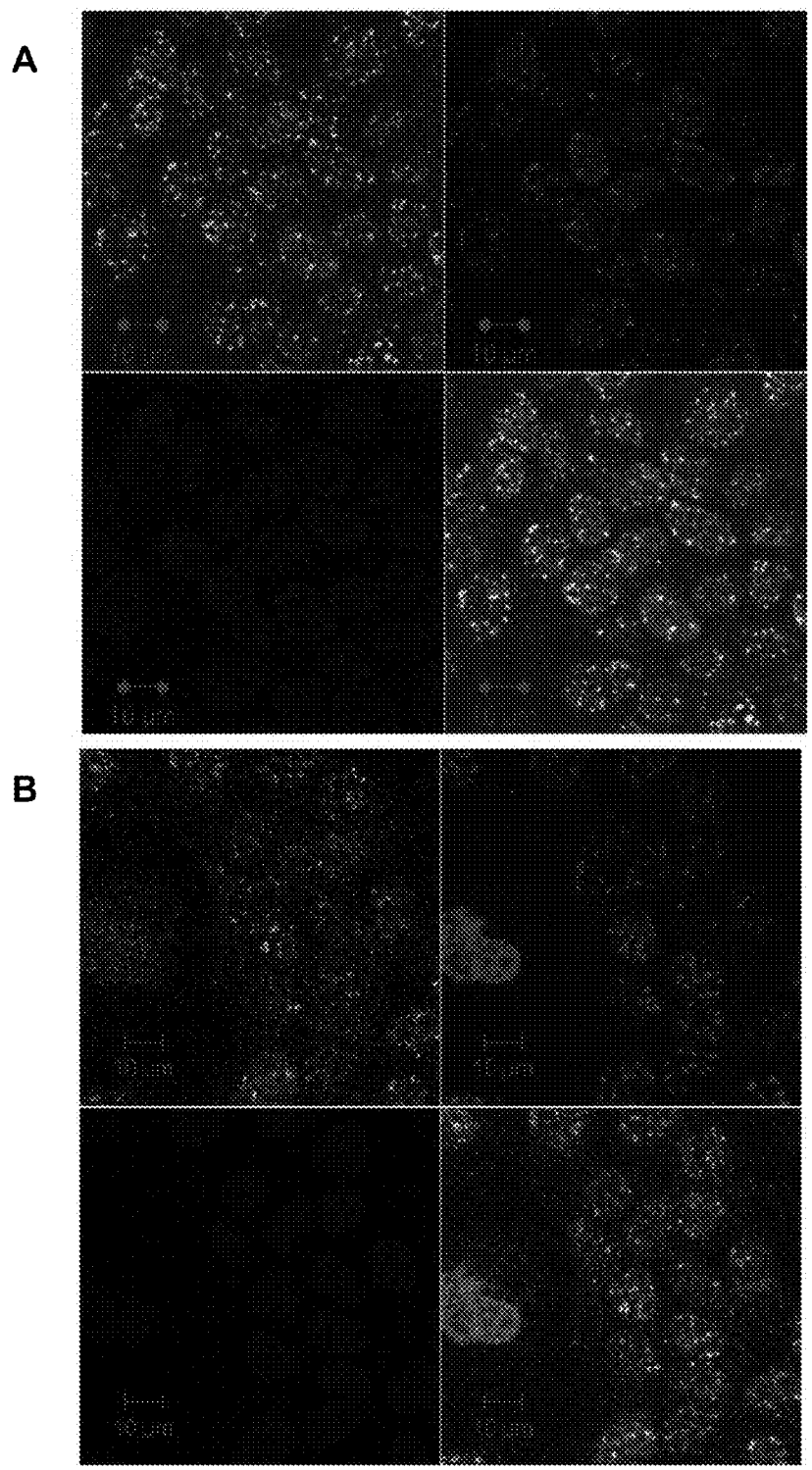
FIG. 18 illustrates that MLS-0207587 inhibits BRCA1 colocalization with γH2AX in IR-treated DLD1 cells. (A) shows colocalization of BRCA1 and γH2AX (lower left panel) in untreated irradiated DLD1 cells, while (B) shows a lack of colocalization as illustrated by a lack of foci when the DLD1 cells are treated with 20 µM MLS-0207587 for 18 hours followed by irradiation at 1 Gy followed by 1 hour recovery. (Green: BRCA1; Red: γH2AX).
Figure 19:
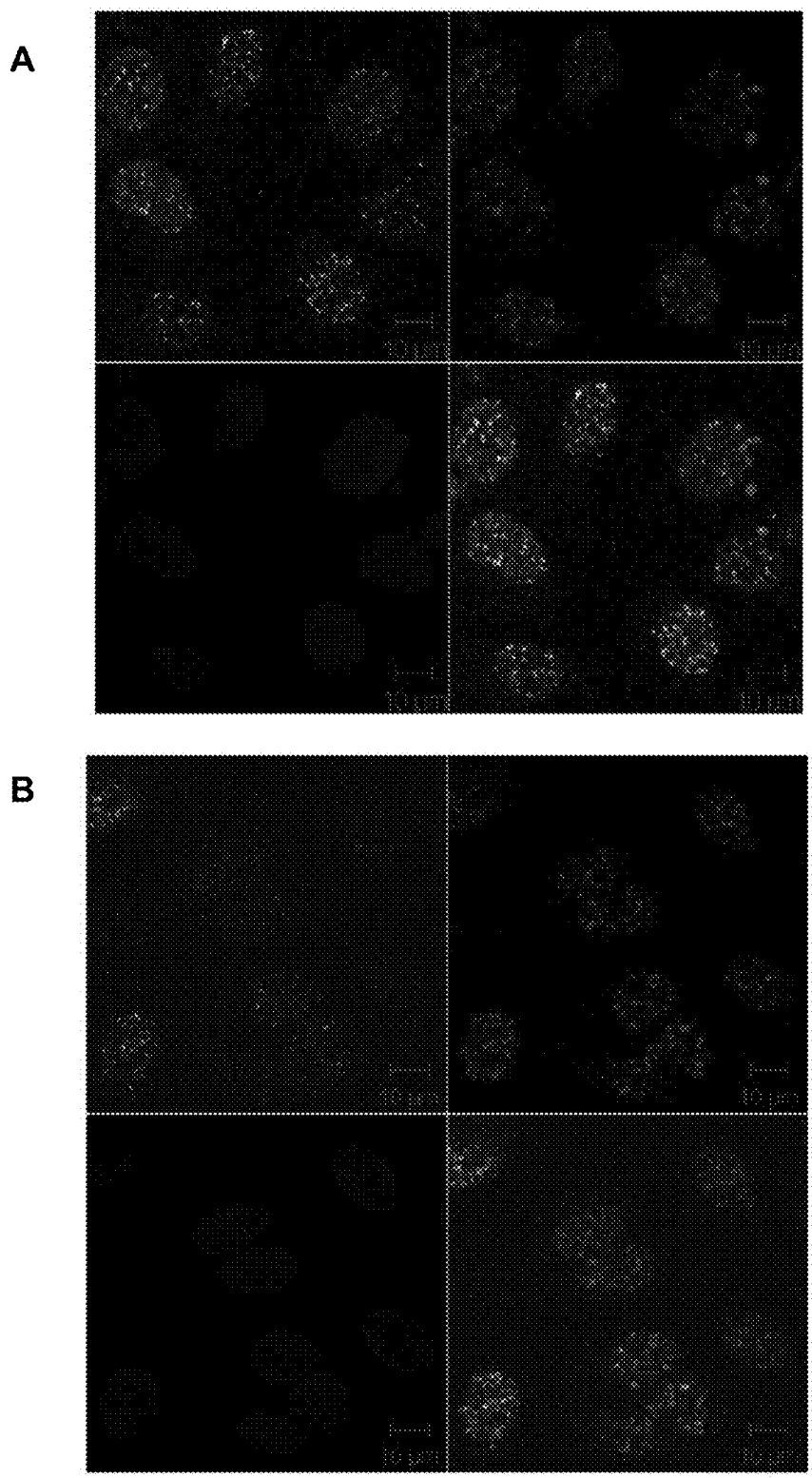
FIG. 19 illustrates that MLS-0207587 inhibits BRCA1 colocalization with γH2AX in IR-treated U20S cells. (A) shows colocalization of BRCA1 and γH2AX (lower left panel) in untreated irradiated U20S cells, while (B) shows a lack of colocalization as illustrated by a lack of foci when the U20S cells are treated with 20 µM MLS-0207587 for 18 hours followed by irradiation (1 Gy; 1 hour). (Green: BRCA1; Red: γH2AX).

VSV-G pseudotyped pNL43LUCR⁻ E⁻, an HIV plasmid which has a luciferase gene inserted in the NEF position and with frameshift mutations in the ENV and VPR genes was used to test infectivity of HIV after treatment with SUMO inhibitors. This virus is competent for a single round of replication, and allows for quantitative measurement of infectivity. HeLa cells were treated with the SUMO E1 inhibitor MLS0207587 for 2 hrs before pNL43LUCR⁻E⁻ was introduced. Luciferase activity was collected after 48 hrs and compared to untreated cells. The lead SUMO inhibitor MLS-0207587 inhibited HIV infection in a dose dependent manner (FIG. 14). This mechanism of this inhibition was due to the SUMO inhibitor preventing integration of the HIV viral genome to the host genome, thereby preventing replication of HIV.

REFERENCES

The references listed below and all referenced cited above are hereby incorporated by reference in their entirety as if fully set forth herein.

al-Khodairy, F., Enoch, T., Hagan, I. M., and Carr, A. M. (1995) *J Cell Sci* 108 (Pt 2), 475-486

Andrews, E. A., Palecek, J., Sergeant, J., Taylor, E., Lehmann, A. R., and Watts, F. Z. (2005) *Mol Cell Biol* 25, 185-196

Bartek, J. and Z. Hodny, SUMO boosts the DNA damage response barrier against cancer. *Cancer Cell*, 2010. 17(1): p. 9-11.

Bartek, J. and Z. Hodny, SUMO boosts the DNA damage response barrier against cancer. *Cancer Cell*, 2010. 17(1): p. 9-11.

Berglink, S, and S. Jentsch, Principles of ubiquitin and SUMO modifications in DNA repair. *Nature*, 2009. 458(7237): p. 461-7.

Boggio, R. and S. Chiocca, Viruses and sumoylation: recent highlights. *Curr Opin Microbiol*, 2006. 9(4): p. 430-6.

Bohnsack, R. N. and A. L. Haas, Conservation in the mechanism of Nedd8 activation by the human AppBp1-Uba3 heterodimer. *J Biol Chem*, 2003. 278(29): p. 26823-30.

Burgess, R. C., Rahman, S., Lisby, M., Rothstein, R., and Zhao, X. (2007) *Molecular and cellular biology* 27, 6153-6162

Burt, C. G., R. R. Cima, W. A. Koltun, C. E. Littlejohn, R. Ricciardi, L. K. Temple, D. A. Rothenberger, and N. N. Baxter, Developing a research agenda for the American Society of Colon and Rectal Surgeons: results of a delphi approach. *Dis Colon Rectum*, 2009. 52(5): p. 898-905.

Cano, K. E., Y. J. Li, and Y. Chen, NMR metabolomic profiling reveals new roles of SUMOylation in DNA damage response. *J Proteome Res*, 2010. 9(10): p. 5382-8.

Cao, X., C. Clavijo, X. Li, H. H. Lin, Y. Chen, H. M. Shih, and D. K. Ann, SUMOylation of HMGA2: selective destabilization of promyelocytic leukemia protein via proteasome. *Mol Cancer Ther*, 2008. 7(4): p. 923-34.

Carter, S., O. Bischof, A. Dejean, and K. H. Vousden, C-terminal modifications regulate MDM2 dissociation and nuclear export of p53. *Nat Cell Biol*, 2007. 9(4): p. 428-35.

Chekmarev, D. S., S. V. Shorshnev, A. E. Stepanov, A. N. Kasatkin, *Highly selective substitutions in 2,3-dichloropyrazine. A novel general approach to aloisines. Tetrahedron,* 2006, 62, 9919-9930.

Chen, Y., The enzymes in ubiquitin-like post-translational modifications. *Biosci Trends,* 2007. 1(1): p. 16-25.

Cheng, J., X. Kang, S. Zhang, and E. T. Yeh, SUMO-specific protease 1 is essential for stabilization of HIF1alpha during hypoxia. *Cell,* 2007. 131(3): p. 584-95.

Chung, V., B. Zhou, X. Liu, L. Zhu, L. M. Boo, H. V. Nguyen, D. K. Ann, J. Song, Y. Chen, and Y. Yen, SUMOylation plays a role in gemcitabine- and bortezomib-induced cytotoxicity in human oropharyngeal carcinoma KB gemcitabine-resistant clone. *Mol Cancer Ther,* 2006. 5(3): p. 533-40.

Comerford, K. M., M. O. Leonard, J. Karhausen, R. Carey, S. P. Colgan, and C. T. Taylor, Small ubiquitin-related modifier-1 modification mediates resolution of CREB-dependent responses to hypoxia. *Proc Natl Acad Sci USA,* 2003. 100(3): p. 986-91.

Cook, C. E., Hochstrasser, M., and Kerscher, O. (2009) *Cell Cycle* 8, 1080-1089

Darzynkiewicz, Z., F. Traganos, and D. Wlodkowic, Impaired DNA damage response—an Achilles' heel sensitizing cancer to chemotherapy and radiotherapy. *Eur J Pharmacol,* 2009. 625(1-3): p. 143-50.

de Vries, S. J., M. van Dijk, and A. M. Bonvin, The HADDOCK web server for data-driven biomolecular docking. *Nat Protoc,* 2010. 5(5): p. 883-97.

Doksani, Y., R. Bermejo, S. Fiorani, J. E. Haber, and M. Foiani, Replicon dynamics, dormant origin firing, and terminal fork integrity after double-strand break formation. *Cell,* 2009. 137(2): p. 247-58.

Doksani, Y., R. Bermejo, S. Fiorani, J. E. Haber, and M. Foiani, Replicon dynamics, dormant origin firing, and terminal fork integrity after double-strand break formation. *Cell,* 2009. 137(2): p. 247-58.

Dominguez, C., R. Boelens, and A. M. Bonvin, HADDOCK: a protein-protein docking approach based on biochemical or biophysical information. *J Am Chem Soc,* 2003. 125(7): p. 1731-7.

Driscoll, J. J. and R. Dechowdhury, Therapeutically targeting the SUMOylation, Ubiquitination and Proteasome pathways as a novel anticancer strategy. *Target Oncol,* 2010. 5(4): p. 281-9.

Fukui, L. and Y. Chen, NvMap: automated analysis of NMR chemical shift perturbation data. *Bioinformatics,* 2007. 23(3): p. 378-80.

Galanty, Y., R. Belotserkovskaya, J. Coates, S. Polo, K. M. Miller, and S. P. Jackson, Mammalian SUMO E3-ligases PIAS1 and PIAS4 promote responses to DNA double-strand breaks. *Nature,* 2009. 462(7275): p. 935-9.

Galanty, Y., R. Belotserkovskaya, J. Coates, S. Polo, K. M. Miller, and S. P. Jackson, Mammalian SUMO E3-ligases PIAS1 and PIAS4 promote responses to DNA double-strand breaks. *Nature,* 2009. 462(7275): p. 935-9.

Garcia-Aguilar, J., E. Hernandez de And a, P. Sirivongs, S. H. Lee, R. D. Madoff, and D. A. Rothenberger, A pathologic complete response to preoperative chemoradiation is associated with lower local recurrence and improved survival in rectal cancer patients treated by mesorectal excision. *Dis Colon Rectum,* 2003. 46(3): p. 298-304.

Genin, E., M. Reboud-Ravaux, and J. Vidal, Proteasome inhibitors: recent advances and new perspectives in medicinal chemistry. *Curr Top Med Chem.* 10(3): p. 232-56.

Genin, E., M. Reboud-Ravaux, and J. Vidal, Proteasome inhibitors: recent advances and new perspectives in medicinal chemistry. *Curr Top Med Chem.* 10(3): p. 232-56.

Gilbreth, R. N., K. Truong, I. Madu, A. Koide, J. Wojcik, N.-S. Li, J. A. Piccirilli, Y. Chen, and S. Koide, Isoform-specific Monobody Inhibitors of SUMO/SIM Interactions Engineered Using Structure-guided Library Design. *Proceedings of the National Academy of Sciences,* 2011. in press.

Gostissa, M., A. Hengstermann, V. Fogal, P. Sandy, S. E. Schwarz, M. Scheffner, and G. Del Sal, Activation of p53 by conjugation to the ubiquitin-like protein SUMO-1. *Embo J,* 1999. 18(22): p. 6462-71.

Haas, A. L. and I. A. Rose, The mechanism of ubiquitin activating enzyme. A kinetic and equilibrium analysis. *J Biol Chem,* 1982. 257(17): p. 10329-37.

Hay, R. T., SUMO: a history of modification. *Mol Cell,* 2005. 18(1): p. 1-12.

Hay, R. T., SUMO: a history of modification. *Mol Cell,* 2005. 18(1): p. 1-12.

Huang, D. T., H. W. Hunt, M. Zhuang, M. D. Ohi, J. M. Holton, and B. A. Schulman, Basis for a ubiquitin-like protein thioester switch toggling E1-E2 affinity. *Nature,* 2007. 445(7126): p. 394-8.

Ii, T., Mullen, J. R., Slagle, C. E., and Brill, S. J. (2007) *DNA Repair (Amst)* 6, 1679-1691

Jaber, T., C. R. Bohl, G. L. Lewis, C. Wood, J. T. West, Jr., and R. A. Weldon, Jr., Human Ubc9 contributes to production of fully infectious human immunodeficiency virus type 1 virions. *J Virol,* 2009. 83(20): p. 10448-59.

Jeggo, P. and M. F. Lavin, Cellular radiosensitivity: how much better do we understand it? *Int J Radiat Biol,* 2009. 85(12): p. 1061-81.

Keshelava, N., T. Frgala, J. Krejsa, O. Kalous, and C. P. Reynolds, DIMSCAN: a microcomputer fluorescence-based cytotoxicity assay for preclinical testing of combination chemotherapy. *Methods Mol Med,* 2005. 110: p. 139-53.

Kho, C., A. Lee, D. Jeong, J. G. Oh, A. H. Chaanine, E. Kizana, W. J. Park, and R. J. Hajjar, SUMO1-dependent modulation of SERCA2a in heart failure. *Nature,* 2011. 477(7366): p. 601-5.

Kim, J. H., H. J. Choi, B. Kim, M. H. Kim, J. M. Lee, I. S. Kim, M. H. Lee, S. J. Choi, K. I. Kim, S. I. Kim, C. H. Chung, and S. H. Baek, Roles of sumoylation of a reptin chromatin-remodelling complex in cancer metastasis. *Nat Cell Biol,* 2006. 8(6): p. 631-9.

Kim, E. T., Y. E. Kim, Y. H. Huh, and J. H. Ahn, Role of noncovalent SUMO binding by the human cytomegalovirus IE2 transactivator in lytic growth. *J. Virol.* 84(16): p. 8111-23.

Kim, K. I. and S. H. Baek, SUMOylation code in cancer development and metastasis. *Mol Cells,* 2006. 22(3): p. 247-53.

Li, Y. J., J. M. Stark, D. J. Chen, D. K. Ann, and Y. Chen, Role of SUMO:SIM-mediated protein-protein interaction in non-homologous end joining. *Oncogene,* 2010. 29(24): p. 3509-18.

Li, Y. J., J. M. Stark, D. J. Chen, D. K. Ann, and Y. Chen, Role of SUMO:SIM-mediated protein-protein interaction in non-homologous end joining. *Oncogene,* 2010. 29(24): p. 3509-18.

Li, T., R. Santockyte, R. F. Shen, E. Tekle, G. Wang, D. C. Yang, and P. B. Chock, Expression of SUMO-2/3 induced senescence through p53- and pRB-mediated pathways. *J Biol Chem,* 2006. 281(47): p. 36221-7.

Lin, D., M. H. Tatham, B. Yu, S. Kim, R. T. Hay, and Y. Chen, Identification of a substrate recognition site on Ubc9. *J Biol Chem*, 2002. 277(24): p. 21740-8.

Liu, Q., C. Jin, X. Liao, Z. Shen, D. J. Chen, and Y. Chen, The binding interface between an E2 (UBC9) and a ubiquitin homologue (UBL1). *J Biol Chem*, 1999. 274(24): p. 16979-87.

Liu, Q., Y. C. Yuan, B. Shen, D. J. Chen, and Y. Chen, Conformational flexibility of a ubiquitin conjugation enzyme (E2). *Biochemistry*, 1999. 38(5): p. 1415-25.

Liu, Q., B. Shen, D. J. Chen, and Y. Chen, Backbone resonance assignments of human UBC9. *J Biomol NMR*, 1999. 13(1): p. 89-90.

Liu, B., S. Tahk, K. M. Yee, G. Fan, and K. Shuai, The ligase PIAS1 restricts natural regulatory T cell differentiation by epigenetic repression. *Science*, 2010. 330(6003): p. 521-5.

Lois, L. M. and C. D. Lima, Structures of the SUMO E1 provide mechanistic insights into SUMO activation and E2 recruitment to E1. *Embo J*, 2005. 24(3): p. 439-51.

Luo, J., M. J. Emanuele, D. Li, C. J. Creighton, M. R. Schlabach, T. F. Westbrook, K. K. Wong, and S. J. Elledge, A genome-wide RNAi screen identifies multiple synthetic lethal interactions with the Ras oncogene. *Cell*, 2009. 137(5): p. 835-48.

Luo, J., M. J. Emanuele, D. Li, C. J. Creighton, M. R. Schlabach, T. F. Westbrook, K. K. Wong, and S. J. Elledge, A genome-wide RNAi screen identifies multiple synthetic lethal interactions with the Ras oncogene. *Cell*, 2009. 137(5): p. 835-48.

Martin, S., K. A. Wilkinson, A. Nishimune, and J. M. Henley, Emerging extranuclear roles of protein SUMOylation in neuronal function and dysfunction. *Nat Rev Neurosci*, 2007. 8(12): p. 948-59.

Mayer, M. and B. Meyer, Group epitope mapping by saturation transfer difference NMR to identify segments of a ligand in direct contact with a protein receptor. *J Am Chem Soc*, 2001. 123(25): p. 6108-17.

Mo, Y. Y. and S. J. Moschos, Targeting Ubc9 for cancer therapy. *Expert Opin Ther Targets*, 2005. 9(6): p. 1203-16.

Mo, Y. Y. and S. J. Moschos, Targeting Ubc9 for cancer therapy. *Expert Opin Ther Targets*, 2005. 9(6): p. 1203-16.

Mo, Y. Y., Y. Yu, E. Theodosiou, P. L. Ee, and W. T. Beck, A role for Ubc9 in tumorigenesis. *Oncogene*, 2005. 24(16): p. 2677-83.

Mohan, R. D., A. Rao, J. Gagliardi, and M. Tini, SUMO-1-dependent allosteric regulation of thymine DNA glycosylase alters subnuclear localization and CBP/p300 recruitment. *Mol Cell Biol*, 2007. 27(1): p. 229-43.

Mohan, R. D., A. Rao, J. Gagliardi, and M. Tini, SUMO-1-dependent allosteric regulation of thymine DNA glycosylase alters subnuclear localization and CBP/p300 recruitment. *Mol Cell Biol*, 2007. 27(1): p. 229-43.

Morris, J. R., C. Boutell, M. Keppler, R. Densham, D. Weekes, A. Alamshah, L. Butler, Y. Galanty, L. Pangon, T. Kiuchi, T. Ng, and E. Solomon, The SUMO modification pathway is involved in the BRCA1 response to genotoxic stress. *Nature*, 2009. 462(7275): p. 886-90.

Morris, J. R., C. Boutell, M. Keppler, R. Densham, D. Weekes, A. Alamshah, L. Butler, Y. Galanty, L. Pangon, T. Kiuchi, T. Ng, and E. Solomon, The SUMO modification pathway is involved in the BRCA1 response to genotoxic stress. *Nature*, 2009. 462(7275): p. 886-90.

Muller, S., M. Berger, F. Lehembre, J. S. Seeler, Y. Haupt, and A. Dejean, c-Jun and p53 activity is modulated by SUMO-1 modification. *J Biol Chem*, 2000. 275(18): p. 13321-9.

Nagai, S., Dubrana, K., Tsai-Pflugfelder, M., Davidson, M. B., Roberts, T. M., Brown, G. W., Varela, E., Hediger, F., Gasser, S. M., and Krogan, N. J. (2008) *Science* (New York, N.Y. 322, 597-602

Nguyen, H. V., J. L. Chen, J. Zhong, K. J. Kim, E. D. Crandall, Z. Borok, Y. Chen, and D. K. Ann, SUMOylation attenuates sensitivity toward hypoxia- or desferroxamine-induced injury by modulating adaptive responses in salivary epithelial cells. *Am J Pathol*, 2006. 168(5): p. 1452-63.

Ohmori, J., M. Shimizu-Sasamata, M. Okada, S. Sakamoto, 8-(1*H*-Imidazol-1-yl-7-nitro-4(5*H*)imidazo[1,2-a]quinoxalinone and Related Compounds: Synthesis and Structure-Activity Relationships for the AMPA-type Non-NMDA Receptor. *J. Med. Chem.* 1997, 40, 2053-2063.

Olsen, S. K., A. D. Capili, X. Lu, D. S. Tan, and C. D. Lima, Active site remodelling accompanies thioester bond formation in the SUMO E1. *Nature*. 463(7283): p. 906-12.

Ouyang, K. J., L. L. Woo, J. Zhu, D. Huo, M. J. Matunis, and N. A. Ellis, SUMO modification regulates BLM and RAD51 interaction at damaged replication forks. *PLoS Biol*, 2009. 7(12): p. e1000252.

Pellecchia, M., D. Meininger, Q. Dong, E. Chang, R. Jack, and D. S. Sem, NMR-based structural characterization of large protein-ligand interactions. *J Biomol NMR*, 2002. 22(2): p. 165-73.

Pfander, B., G. L. Moldovan, M. Sacher, C. Hoege, and S. Jentsch, SUMO-modified PCNA recruits Srs2 to prevent recombination during S phase. *Nature*, 2005. 436(7049): p. 428-33.

Pfander, B., G. L. Moldovan, M. Sacher, C. Hoege, and S. Jentsch, SUMO-modified PCNA recruits Srs2 to prevent recombination during S phase. *Nature*, 2005. 436(7049): p. 428-33.

Prudden, J., Pebernard, S., Raffa, G., Slavin, D. A., Perry, J. J., Tainer, J. A., McGowan, C. H., and Boddy, M. N. (2007) *Embo J* 26, 4089-4101

Prudden, J., J. J. Perry, A. S. Arvai, J. A. Tainer, and M. N. Boddy, Molecular mimicry of SUMO promotes DNA repair. *Nat Struct Mol Biol*, 2009. 16(5): p. 509-16.

Reibarkh, M., T. J. Malia, and G. Wagner, NMR distinction of single- and multiple-mode binding of small-molecule protein ligands. *J Am Chem Soc*, 2006. 128(7): p. 2160-1.

Religa, T. L. and L. E. Kay, Optimal methyl labeling for studies of supra-molecular systems. *J Biomol NMR*. 47(3): p. 163-9.

Ribet, D., M. Hamon, E. Gouin, M. A. Nahori, F. Impens, H. Neyret-Kahn, K. Gevaert, J. Vandekerckhove, A. Dejean, and P. Cossart, *Listeria monocytogenes* impairs SUMOylation for efficient infection. *Nature*, 2010. 464(7292): p. 1192-5.

Ribet, D., M. Hamon, E. Gouin, M. A. Nahori, F. Impens, H. Neyret-Kahn, K. Gevaert, J. Vandekerckhove, A. Dejean, and P. Cossart, *Listeria monocytogenes* impairs SUMOylation for efficient infection. *Nature*, 2010. 464(7292): p. 1192-5.

Rouleau, N., J. Wang, L. Karras, E. Andrews, M. Bielefeld-Sevigny, and Y. Chen, Highly sensitive assays for SUMOylation and small ubiquitin-like modifier-dependent protein-protein interactions. *Anal Biochem*, 2008. 375(2): p. 364-6.

Sarge, K. D. and O. K. Park-Sarge, Sumoylation and human disease pathogenesis. *Trends Biochem Sci*, 2009. 34(4): p. 200-5.

Sarge, K. D. and O. K. Park-Sarge, Sumoylation and human disease pathogenesis. *Trends Biochem Sci*, 2009. 34(4): p. 200-5.

Sarge, K. D. and O. K. Park-Sarge, SUMO and its role in human diseases. *Int Rev Cell Mol Biol*, 2011. 288: p. 167-83.

Seu, C. S, and Y. Chen, Identification of SUMO-binding motifs by NMR. *Methods Mol Biol*, 2009. 497: p. 121-38.

Shayeghi, M., Doe, C. L., Tavassoli, M., and Watts, F. Z. (1997) *Nucleic Acids Res* 25, 1162-1169

Song, J., L. K. Durrin, T. A. Wilkinson, T. G. Krontiris, and Y. Chen, Identification of a SUMO-binding motif that recognizes SUMO-modified proteins. *Proc Natl Acad Sci USA*, 2004. 101(40): p. 14373-8.

Song, J., L. K. Durrin, T. A. Wilkinson, T. G. Krontiris, and Y. Chen, Identification of a SUMO-binding motif that recognizes SUMO-modified proteins. *Proc Natl Acad Sci USA*, 2004. 101(40): p. 14373-8.

Song, J., Z. Zhang, W. Hu, and Y. Chen, Small ubiquitin-like modifier (SUMO) recognition of a SUMO binding motif: a reversal of the bound orientation. *J Biol Chem*, 2005. 280 (48): p. 40122-9.

Song, J., Z. Zhang, W. Hu, and Y. Chen, Small ubiquitin-like modifier (SUMO) recognition of a SUMO binding motif: a reversal of the bound orientation. *J Biol Chem*, 2005. 280 (48): p. 40122-9.

Song, J., J. Wang, A. A. Jozwiak, W. Hu, P. M. Swiderski, and Y. Chen, Stability of thioester intermediates in ubiquitin-like modifications. *Protein Sci*, 2009. 18(12): p. 2492-9.

Sprangers, R., A. Velyvis, and L. E. Kay, Solution NMR of supramolecular complexes: providing new insights into function. *Nat Methods*, 2007. 4(9): p. 697-703.

Spengler, M. L., S. B. Kennett, K. S. Moorefield, S. O, Simmons, M. G. Brattain, and J. M. Horowitz, Sumoylation of internally initiated Sp3 isoforms regulates transcriptional repression via a Trichostatin A-insensitive mechanism. *Cell Signal*, 2005. 17(2): p. 153-66.

Steffan, J. S., N. Agrawal, J. Pallos, E. Rockabrand, L. C. Trotman, N. Slepko, K. Illes, T.
Lukacsovich, Y. Z. Zhu, E. Cattaneo, P. P. Pandolfi, L. M. Thompson, and J. L. Marsh, SUMO modification of Huntingtin and Huntington's disease pathology. *Science*, 2004. 304 (5667): p. 100-4.

Steffan, J. S., N. Agrawal, J. Pallos, E. Rockabrand, L. C. Trotman, N. Slepko, K. Illes, T. Lukacsovich, Y. Z. Zhu, E. Cattaneo, P. P. Pandolfi, L. M. Thompson, and J. L. Marsh, SUMO modification of Huntingtin and Huntington's disease pathology. *Science*, 2004. 304(5667): p. 100-4.

Stehmeier, P. and S. Muller, Regulation of p53 family members by the ubiquitin-like SUMO system. *DNA Repair (Amst)*, 2009. 8(4): p. 491-8.

Steinacher, R. and P. Schar, Functionality of human thymine DNA glycosylase requires SUMO-regulated changes in protein conformation. *Curr Biol*, 2005. 15(7): p. 616-23.

Steinacher, R. and P. Schar, Functionality of human thymine DNA glycosylase requires SUMO-regulated changes in protein conformation. *Curr Biol*, 2005. 15(7): p. 616-23.

Subramaniam, S., K. M. Sixt, R. Barrow, and S. H. Snyder, Rhes, a striatal specific protein, mediates mutant-huntingtin cytotoxicity. *Science*, 2009. 324(5932): p. 1327-30.

Subramaniam, S., K. M. Sixt, R. Barrow, and S. H. Snyder, Rhes, a striatal specific protein, mediates mutant-huntingtin cytotoxicity. *Science*, 2009. 324(5932): p. 1327-30.

Sun, H., Leverson, J. D., and Hunter, T. (2007) *Embo J* 26, 4102-4112

Tan, J. A., J. Song, Y. Chen, and L. K. Durrin, Phosphorylation-dependent interaction of SATB1 and PIAS1 directs SUMO-regulated caspase cleavage of SATB1. *Mol Cell Biol*, 2010. 30(11): p. 2823-36.

Tan, J. A., Y. Sun, J. Song, Y. Chen, T. G. Krontiris, and L. K. Durrin, SUMO conjugation to the matrix attachment region-binding protein, special AT-rich sequence-binding protein-1 (SATB1), targets SATB1 to promyelocytic nuclear bodies where it undergoes caspase cleavage. *J Biol Chem*, 2008. 283(26): p. 18124-34.

Tatham, M. H., S. Kim, E. Jaffray, J. Song, Y. Chen, and R. T. Hay, Unique binding interactions among Ubc9, SUMO and RanBP2 reveal a mechanism for SUMO paralog selection. *Nat Struct Mol Biol*, 2005. 12(1): p. 67-74.

Tatham, M. H., Y. Chen, and R. T. Hay, Role of two residues proximal to the active site of Ubc9 in substrate recognition by the Ubc9.5UMO-1 thiolester complex. *Biochemistry*, 2003. 42(11): p. 3168-79.

Tatham, M. H., S. Kim, B. Yu, E. Jaffray, J. Song, J. Zheng, M. S. Rodriguez, R. T. Hay, and Y. Chen, Role of an N-terminal site of Ubc9 in SUMO-1, -2, and -3 binding and conjugation. *Biochemistry*, 2003. 42(33): p. 9959-69.

Tatham, M. H., S. Kim, B. Yu, E. Jaffray, J. Song, J. Zheng, M. S. Rodriguez, R. T. Hay, and Y. Chen, Role of an N-terminal site of Ubc9 in SUMO-1, -2, and -3 binding and conjugation. *Biochemistry*, 2003. 42(33): p. 9959-69.

Tatham, M. H., B. Yu, S. Kim, E. Jaffray, M. S. Rodriguez, R. T. Hay, and Y. Chen, Identification of the initial docking site of the SUMO-1 moiety of the E1-SUMO-1 thiolester on E2. submitted., 2002.

Tokgoz, Z., R. N. Bohnsack, and A. L. Haas, Pleiotropic effects of ATP.Mg2+ binding in the catalytic cycle of ubiquitin-activating enzyme. *J Biol Chem*, 2006. 281(21): p. 14729-37.

Truong, K., Y. Su, J. Song, and Y. Chen, Entropy-Driven Mechanism of a SUMO Ligase. *Biochemistry*, 2011. in press.

Tugarinov, V., R. Sprangers, and L. E. Kay, Line narrowing in methyl-TROSY using zero-quantum 1H-13C NMR spectroscopy. *J Am Chem Soc*, 2004. 126(15): p. 4921-5.

Ulrich, H. D., Preface. Ubiquitin, SUMO and the maintenance of genome stability. *DNA Repair (Amst)*, 2009. 8(4): p. 429.

Ulrich, H. D., The SUMO system: an overview. *Methods Mol Biol*, 2009.497: p. 3-16.

van Attikum, H. and S. M. Gasser, Crosstalk between histone modifications during the DNA damage response. *Trends Cell Biol*, 2009. 19(5): p. 207-17.

van Dijk, A. D., S. J. de Vries, C. Dominguez, H. Chen, H. X. Zhou, and A. M. Bonvin, Data-driven docking: HADDOCK's adventures in CAPRI. *Proteins*, 2005. 60(2): p. 232-8.

Wang, J., B. Lee, S. Cai, L. Fukui, W. Hu, and Y. Chen, Conformational transition associated with E1-E2 interaction in small ubiquitin-like modifications. *J Biol Chem*, 2009. 284(30): p. 20340-8.

Wang, J., W. Hu, S. Cai, B. Lee, J. Song, and Y. Chen, The intrinsic affinity between E2 and the Cys domain of E1 in ubiquitin-like modifications. *Mol Cell*, 2007. 27(2): p. 228-37.

Wang, J., S. Cai, and Y. Chen, Mechanism of E1-E2 interaction for the inhibition of Ubl adenylation. *J Biol Chem*, 2010. 285(43): p. 33457-62.

Wang, J. and Y. Chen, Role of the Zn(2+) motif of E1 in SUMO adenylation. *J Biol Chem*, 2010. 285(31): p. 23732-8.

Wang, J., S. Cai, and Y. Chen, Mechanism of E1-E2 interaction for the inhibition of Ubl adenylation. *J Biol. Chem*.

Wang, J. and Y. Chen, Role of the Zn($2^+$) motif of E1 in SUMO adenylation. *J Biol Chem*. 285(31): p. 23732-8.

Wang, L. and S. Banerjee, Differential PIAS3 expression in human malignancy. *Oncol Rep,* 2004. 11(6): p. 1319-24.

Watanabe, T., Chemoradiation and adjuvant chemotherapy for rectal cancer. *Int J Clin Oncol,* 2008. 13: p. 488-97.

Wu, F. and Y. Y. Mo, Ubiquitin-like protein modifications in prostate and breast cancer. *Front Biosci,* 2007. 12: p. 700-11.

Yeh, E. T., SUMOylation and De-SUMOylation: wrestling with life's processes. *J Biol Chem,* 2009. 284(13): p. 8223-7.

Yeh, E. T., SUMOylation and De-SUMOylation: wrestling with life's processes. *J Biol Chem,* 2009. 284(13): p. 8223-7.

Zhao, X., and Blobel, G. (2005) *Proc Natl Acad Sci USA*

Zhu, S., M. Sachdeva, F. Wu, Z. Lu, and Y. Y. Mo, Ubc9 promotes breast cell invasion and metastasis in a sumoylation-independent manner. *Oncogene,* 2010. 29(12): p. 1763-72.

What is claimed is:

1. A method for inhibiting a small ubiquitin-like modifier enzyme in a cell, comprising administering to the cell a compound having the structure:

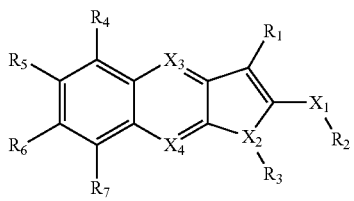

(ii)

and pharmaceutically acceptable salts and stereoisomers thereof;

wherein $R_1$ and $R_2$ are independently selected from the group consisting of H, —S(O)$_2$—$R_8$, —CN and —C(O)—X—$R_9$;

wherein $R_8$ is an alkyl, or aryl;

wherein $R_9$ is an alkyl, aryl, or heteroaryl;

wherein X is selected from the group consisting of CH$_2$, O, NH, and S;

wherein $R_3$ is selected from the group consisting of an alkyl, an alkenyl, and an alkylaryl;

wherein each of $R_4$, $R_5$, $R_6$ and $R_7$ are independently selected from the group consisting of H, a halogen, and an alkyl;

wherein $X_1$ is selected from the group consisting of CH$_2$, NH, O, and S; and wherein $X_2$, $X_3$ and $X_4$ are N; or

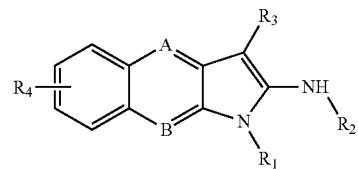

(iii)

and pharmaceutically acceptable salts and stereoisomers thereof, including mixtures thereof in all ratios, wherein:

A and B are N;

$R_1$ is H, alkyl, haloalkyl, alkyl-OR$_1$, aryl, heterocyclyl, benzyl, or alkyl-aryl where $R_1$ is optionally substituted with one to four $R_4$ groups;

$R_2$ is H or L-R$_5$, wherein L is —C(O)— or —S(O)$_2$—, and $R_5$ is alkyl, haloalkyl, cycloalkyl, aryl, heterocyclyl, benzyl, or alkyl-aryl optionally substituted with one to four $R_4$ groups;

$R_3$ is CN, —C(O)—OR$_6$, —C(O)—NHR$_6$, or —S(O)$_2$R$_6$, wherein $R_6$ is H, alkyl, haloalkyl, aryl, or heteroaryl optionally substituted with one to four $R_4$ groups; and $R_4$ is halo, —OR$^7$, —N(R$^7$)$_2$, —S(R$^7$)$_2$, —S(O)$_2$R$^7$, —S(O)$_2$N(R$^7$)$_2$, —S(O)$_2$OR$^7$, —N(R$^7$)S(O)$_2$R$^7$, —OS(O)$_2$R$^7$, —C(O)R$^7$, —C(O)OR$^7$, —C(O)N(R$^7$)$_2$, —OC(O)R$^7$, —OC(O)OR$^7$, —OC(O)N(R$^7$)$_2$, —N(R$^7$)C(O)R$^7$, —N(R$^7$)C(O)OR$^7$, —N(R$^7$)C(O)N(R$^7$)$_2$, —CN, —NO$_2$, alkyl, haloalkyl, alkyl-OR$^7$, or alkyl-N(R$^7$)$_2$, where each R$^7$ is independently H, alkyl, haloalkyl, cycloalkyl, heterocyclyl, or aryl.

2. A method for inhibiting a small ubiquitin-like modifier enzyme in a cell, comprising administering to the cell a compound having the structure:

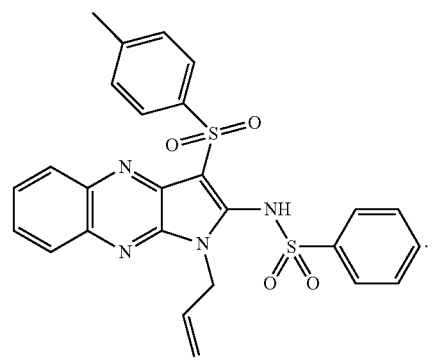 [SMILES: C=CCn1c(NS(=O)(=O)c2ccccc2)c(S(=O)(=O)c2ccc(C)cc2)c2nc3ccccc3nc21]

3. The method of claim 1 or claim 2, wherein the small ubiquitin-like modifier enzyme is small ubiquitin-like modifier enzyme E1 or small ubiquitin-like modifier enzyme E2.

* * * * *